(12) United States Patent
Ciaramella

(10) Patent No.: US 12,318,443 B2
(45) Date of Patent: Jun. 3, 2025

(54) INFLUENZA VACCINE

(71) Applicant: ModernaTX, Inc., Cambridge, MA (US)

(72) Inventor: Giuseppe Ciaramella, Cambridge, MA (US)

(73) Assignee: ModernaTX, Inc., Cambridge, MA (US)

( * ) Notice: Subject to any disclaimer, the term of this patent is extended or adjusted under 35 U.S.C. 154(b) by 0 days.

(21) Appl. No.: 18/322,831

(22) Filed: May 24, 2023

(65) Prior Publication Data

US 2024/0000917 A1 Jan. 4, 2024

Related U.S. Application Data

(60) Continuation of application No. 17/127,949, filed on Dec. 18, 2020, now Pat. No. 11,696,946, which is a division of application No. 16/348,943, filed as application No. PCT/US2017/061182 on Nov. 10, 2017, now Pat. No. 10,925,958.

(60) Provisional application No. 62/421,160, filed on Nov. 11, 2016.

(51) Int. Cl.
| | | |
|---|---|---|
| *C12N 7/00* | (2006.01) | |
| *A61K 9/51* | (2006.01) | |
| *A61K 39/00* | (2006.01) | |
| *A61K 39/12* | (2006.01) | |
| *A61K 39/145* | (2006.01) | |
| *A61P 31/16* | (2006.01) | |
| *C07K 14/005* | (2006.01) | |

(52) U.S. Cl.
CPC .......... *A61K 39/145* (2013.01); *A61K 9/5123* (2013.01); *A61P 31/16* (2018.01); *A61K 2039/53* (2013.01); *A61K 2039/54* (2013.01); *A61K 2039/545* (2013.01); *C12N 2760/16134* (2013.01)

(58) Field of Classification Search
CPC .. A61K 2039/53; A61K 39/12; A61K 39/145; A61K 2039/6018; A61K 31/7115
See application file for complete search history.

(56) References Cited

U.S. PATENT DOCUMENTS

| | | | |
|---|---|---|---|
| 6,040,427 A | 3/2000 | Locht et al. | |
| 6,500,419 B1 | 12/2002 | Hone et al. | |
| 6,514,948 B1 | 2/2003 | Raz et al. | |
| 6,610,044 B2 | 8/2003 | Mathiesen | |
| 7,001,890 B1 | 2/2006 | Wagner et al. | |
| 8,470,771 B2 | 6/2013 | Gao et al. | |
| 8,569,256 B2 | 10/2013 | Heyes et al. | |
| 8,609,142 B2 | 12/2013 | Troiano et al. | |
| 8,613,954 B2 | 12/2013 | Zale et al. | |
| 8,617,608 B2 | 12/2013 | Zale et al. | |
| 8,658,354 B2 | 2/2014 | Kida et al. | |
| 8,692,292 B2 | 4/2014 | Umeda et al. | |
| 8,710,200 B2 | 4/2014 | Schrum et al. | |
| 8,734,832 B2 | 5/2014 | O'Hagan et al. | |
| 8,734,853 B2 | 5/2014 | Sood et al. | |
| 8,754,062 B2 | 6/2014 | De Fougerolles et al. | |
| 8,822,663 B2 | 9/2014 | Schrum et al. | |
| 8,980,864 B2 | 3/2015 | Hoge et al. | |
| 8,999,380 B2 | 4/2015 | Bancel et al. | |
| 9,221,891 B2 | 12/2015 | Bancel et al. | |
| 9,283,287 B2 | 3/2016 | Bancel et al. | |
| 9,303,079 B2 | 4/2016 | Bancel et al. | |
| 9,464,124 B2 | 10/2016 | Bancel et al. | |
| 9,512,456 B2 | 12/2016 | Wang et al. | |
| 9,533,047 B2 | 1/2017 | de Fougerolles et al. | |
| 9,572,896 B2 | 2/2017 | Bancel et al. | |
| 9,597,380 B2 | 3/2017 | Chakraborty et al. | |
| 9,675,668 B2 | 6/2017 | Bancel et al. | |
| 9,803,199 B2 | 10/2017 | Koizumi et al. | |
| 9,868,691 B2 | 1/2018 | Benenato et al. | |
| 9,872,900 B2 | 1/2018 | Ciaramella et al. | |
| 10,023,626 B2 | 7/2018 | Bolen et al. | |
| 10,064,934 B2 | 9/2018 | Ciaramella et al. | |
| 10,064,935 B2 | 9/2018 | Ciaramella et al. | |
| 10,124,055 B2 | 11/2018 | Ciaramella et al. | |
| 10,207,010 B2 | 2/2019 | Besin et al. | |
| 10,232,055 B2 | 3/2019 | Kariko et al. | |
| 10,273,269 B2 | 4/2019 | Ciaramella | |
| 10,286,086 B2 | 5/2019 | Roy et al. | |
| 10,323,076 B2 | 6/2019 | Ellsworth et al. | |
| 10,385,088 B2 | 8/2019 | Fraley et al. | |
| 10,449,244 B2 | 10/2019 | Ciaramella et al. | |
| 10,465,190 B1 | 11/2019 | Chen et al. | |
| 10,493,143 B2 | 12/2019 | Ciaramella et al. | |
| 10,526,629 B2 | 1/2020 | Rabideau et al. | |
| 10,653,712 B2 | 5/2020 | Hoge | |

(Continued)

FOREIGN PATENT DOCUMENTS

| | | |
|---|---|---|
| AU | 652831 B2 | 9/1994 |
| AU | 2015210364 A1 | 3/2017 |

(Continued)

OTHER PUBLICATIONS

U.S. Appl. No. 16/036,318, filed Jul. 16, 2018, Ciaramella et al.
U.S. Appl. No. 16/144,394, filed Sep. 27, 2018, Ciaramella et al.
U.S. Appl. No. 17/204,801, filed Mar. 17, 2021, Ciaramella et al.
U.S. Appl. No. 17/683,171, filed Feb. 28, 2022, Ciaramella et al.
U.S. Appl. No. 18/176,014, filed Feb. 28, 2023, Ciaramella.
U.S. Appl. No. 18/365,948, filed Aug. 4, 2023, Ciaramella.
U.S. Appl. No. 17/819,414, filed Aug. 12, 2022, Ciaramella.
U.S. Appl. No. 15/767,600, filed Apr. 11, 2018, Ciaramella et al.
U.S. Appl. No. 18/306,082, filed Apr. 24, 2023, Ciaramella et al.
U.S. Appl. No. 15/767,609, filed Apr. 11, 2018, Ciaramella et al.
U.S. Appl. No. 15/767,613, filed Apr. 11, 2018, Ciaramella et al.

(Continued)

*Primary Examiner* — Barry A Chestnut
(74) *Attorney, Agent, or Firm* — Courtenay Brinckerhoff; Foley & Lardner LLP

(57) ABSTRACT

The invention relates to compositions and methods for the preparation, manufacture and therapeutic use ribonucleic acid vaccines comprising polynucleotide molecules encoding one or more influenza antigens, such as hemagglutinin antigens.

10 Claims, 6 Drawing Sheets

Specification includes a Sequence Listing.

(56) References Cited

U.S. PATENT DOCUMENTS

| | | |
|---|---|---|
| 10,653,767 B2 | 5/2020 | Ciaramella et al. |
| 10,695,419 B2 | 6/2020 | Ciaramella et al. |
| 10,857,105 B2 | 12/2020 | Benenato et al. |
| 10,925,958 B2 | 2/2021 | Ciaramella |
| 11,027,025 B2 | 6/2021 | Hoge et al. |
| 11,045,540 B2 | 6/2021 | Ciaramella |
| 11,103,578 B2 | 8/2021 | Ciaramella et al. |
| 11,266,735 B2 | 3/2022 | Kallen et al. |
| 11,351,242 B1 | 6/2022 | Lori et al. |
| 11,384,352 B2 | 7/2022 | Miracco |
| 11,406,703 B2 | 8/2022 | Kramarczyk et al. |
| 11,464,848 B2 | 10/2022 | Ciaramella et al. |
| 11,485,960 B2 | 11/2022 | Dousis et al. |
| 11,497,807 B2 | 11/2022 | Ciaramella et al. |
| 11,564,893 B2 | 1/2023 | Smith |
| 11,576,961 B2 | 2/2023 | Ciaramella et al. |
| 11,643,441 B1 | 5/2023 | Ciaramella et al. |
| 11,696,946 B2 | 7/2023 | Ciaramella |
| 11,752,206 B2 | 9/2023 | Ciaramella et al. |
| 11,786,607 B2 | 10/2023 | Hoge et al. |
| 11,851,694 B1 | 12/2023 | Mauger et al. |
| 11,866,696 B2 | 1/2024 | Issa et al. |
| 11,872,278 B2 | 1/2024 | Ciaramella et al. |
| 11,905,525 B2 | 2/2024 | Brito et al. |
| 11,911,453 B2 | 2/2024 | Ciaramella et al. |
| 11,912,982 B2 | 2/2024 | Issa et al. |
| 12,070,495 B2 | 8/2024 | Lusso et al. |
| 12,151,029 B2 | 11/2024 | Hennessy et al. |
| 2001/0001066 A1 | 5/2001 | Cezayirli et al. |
| 2003/0032615 A1 | 2/2003 | Felgner et al. |
| 2005/0032730 A1 | 2/2005 | Von Der Mulbe et al. |
| 2005/0059624 A1 | 3/2005 | Hoerr et al. |
| 2006/0172003 A1 | 8/2006 | Meers et al. |
| 2006/0172966 A1 | 8/2006 | Lipford et al. |
| 2006/0217338 A1 | 9/2006 | Lu et al. |
| 2008/0057080 A1 | 3/2008 | Luke et al. |
| 2008/0171079 A1 | 7/2008 | Hanon et al. |
| 2010/0130588 A1 | 5/2010 | Yaworski et al. |
| 2010/0189729 A1 | 7/2010 | Hoerr et al. |
| 2012/0058153 A1 | 3/2012 | Ilyinskii et al. |
| 2012/0101148 A1 | 4/2012 | Aking et al. |
| 2012/0177701 A1 | 7/2012 | Ilyinski et al. |
| 2012/0189700 A1 | 7/2012 | Aguilar et al. |
| 2012/0276209 A1 | 11/2012 | Cullis et al. |
| 2013/0102034 A1 | 4/2013 | Schrum et al. |
| 2013/0121988 A1 | 5/2013 | Hoerr et al. |
| 2013/0142818 A1 | 6/2013 | Baumhof et al. |
| 2013/0171241 A1 | 7/2013 | Geall |
| 2013/0183355 A1 | 7/2013 | Jain et al. |
| 2013/0189351 A1 | 7/2013 | Geall |
| 2013/0195867 A1 | 8/2013 | Hoerr et al. |
| 2013/0195968 A1 | 8/2013 | Geall et al. |
| 2013/0195969 A1 | 8/2013 | Geall et al. |
| 2013/0236974 A1 | 9/2013 | de Fougerolles et al. |
| 2013/0245103 A1 | 9/2013 | de Fougerolles et al. |
| 2013/0245107 A1 | 9/2013 | de Fougerolles et al. |
| 2013/0259923 A1 | 10/2013 | Bancel et al. |
| 2013/0266640 A1 | 10/2013 | De Fougerolles et al. |
| 2014/0050759 A1 | 2/2014 | Falkner et al. |
| 2014/0065228 A1 | 3/2014 | Yarowoski et al. |
| 2014/0134201 A1 | 5/2014 | Tureci et al. |
| 2014/0147432 A1 | 5/2014 | Bancel et al. |
| 2014/0148502 A1 | 5/2014 | Bancel et al. |
| 2014/0193482 A1 | 7/2014 | Bancel et al. |
| 2014/0206752 A1 | 7/2014 | Afeyan et al. |
| 2014/0255472 A1 | 9/2014 | Geall et al. |
| 2014/0302079 A1 | 10/2014 | Nable et al. |
| 2014/0308304 A1 | 10/2014 | Manoharan et al. |
| 2014/0378538 A1 | 12/2014 | Bancel |
| 2015/0051268 A1 | 2/2015 | Bancel et al. |
| 2015/0056253 A1 | 2/2015 | Bancel et al. |
| 2015/0141499 A1 | 5/2015 | Bancel et al. |
| 2015/0307542 A1 | 10/2015 | Roy et al. |
| 2015/0315541 A1 | 11/2015 | Bancel et al. |
| 2016/0022580 A1 | 1/2016 | Ramsay et al. |
| 2016/0024140 A1 | 1/2016 | Issa et al. |
| 2016/0024141 A1 | 1/2016 | Issa et al. |
| 2016/0032273 A1 | 2/2016 | Shahrokh et al. |
| 2016/0038612 A1 | 2/2016 | Hoge et al. |
| 2016/0194368 A1 | 7/2016 | Hoge et al. |
| 2016/0194625 A1 | 7/2016 | Hoge et al. |
| 2016/0243221 A1 | 8/2016 | Hoge et al. |
| 2016/0317647 A1 | 11/2016 | Ciaramella et al. |
| 2017/0043037 A1 | 2/2017 | Kariko et al. |
| 2017/0202979 A1 | 7/2017 | Chakraborty et al. |
| 2017/0204152 A1 | 7/2017 | Nelson et al. |
| 2017/0130255 A1 | 10/2017 | Wang et al. |
| 2018/0000953 A1 | 1/2018 | Almarsson et al. |
| 2018/0002393 A1 | 1/2018 | Bancel et al. |
| 2018/0021258 A1 | 1/2018 | Graham et al. |
| 2018/0028664 A1 | 2/2018 | Besin et al. |
| 2018/0237849 A1 | 8/2018 | Thompson |
| 2018/0243225 A1 | 8/2018 | Ciaramella |
| 2018/0243230 A1 | 8/2018 | Smith |
| 2018/0256628 A1 | 9/2018 | Hoge et al. |
| 2018/0271795 A1 | 9/2018 | Martini et al. |
| 2018/0271970 A1 | 9/2018 | Ciaramella et al. |
| 2018/0273977 A1 | 9/2018 | Mousavi et al. |
| 2018/0274009 A1 | 9/2018 | Marquardt et al. |
| 2018/0280496 A1 | 10/2018 | Ciaramella et al. |
| 2018/0289792 A1 | 10/2018 | Ciaramella et al. |
| 2018/0296663 A1 | 10/2018 | Hipp et al. |
| 2018/0303929 A1 | 10/2018 | Ciaramella et al. |
| 2018/0311336 A1 | 11/2018 | Ciaramella et al. |
| 2018/0311343 A1 | 11/2018 | Huang et al. |
| 2018/0318409 A1 | 11/2018 | Valiante et al. |
| 2018/0326039 A1 | 11/2018 | Haruta |
| 2018/0363019 A1 | 12/2018 | Hoge |
| 2018/0369374 A1 | 12/2018 | Frederick et al. |
| 2018/0371047 A1 | 12/2018 | Ticho et al. |
| 2019/0002890 A1 | 1/2019 | Martini et al. |
| 2019/0008938 A1 | 1/2019 | Ciaramella et al. |
| 2019/0085368 A1 | 3/2019 | Bancel et al. |
| 2019/0099481 A1 | 4/2019 | Ciaramella et al. |
| 2019/0125839 A1 | 5/2019 | Frederick et al. |
| 2019/0175517 A1 | 6/2019 | Martini et al. |
| 2019/0175727 A1 | 6/2019 | Huang et al. |
| 2019/0192646 A1 | 6/2019 | Cohen et al. |
| 2019/0192653 A1 | 6/2019 | Hoge et al. |
| 2019/0275170 A1 | 9/2019 | Benenato et al. |
| 2019/0298657 A1 | 10/2019 | Martini et al. |
| 2019/0298658 A1 | 10/2019 | Benenato |
| 2019/0300906 A1 | 10/2019 | Martini et al. |
| 2019/0314292 A1 | 10/2019 | Benenato et al. |
| 2019/0314493 A1 | 10/2019 | Ciaramella et al. |
| 2019/0336452 A1 | 11/2019 | Brader |
| 2019/0336595 A1 | 11/2019 | Ciaramella |
| 2019/0351040 A1 | 11/2019 | Valiante et al. |
| 2019/0382774 A1 | 12/2019 | Hoge et al. |
| 2019/0390181 A1 | 12/2019 | Benenato et al. |
| 2020/0030432 A1 | 1/2020 | Ciaramella et al. |
| 2020/0032274 A1 | 1/2020 | Mauger et al. |
| 2020/0038499 A1 | 2/2020 | Narayanan et al. |
| 2020/0054737 A1 | 2/2020 | Ciaramella et al. |
| 2020/0069599 A1 | 3/2020 | Smith et al. |
| 2020/0069793 A1 | 3/2020 | Ciaramella |
| 2020/0069794 A1 | 3/2020 | Ciaramella et al. |
| 2020/0071689 A1 | 3/2020 | Miracco |
| 2020/0085916 A1 | 3/2020 | Martini et al. |
| 2020/0109420 A1 | 4/2020 | Brito et al. |
| 2020/0129445 A1 | 4/2020 | Patel et al. |
| 2020/0129608 A1 | 4/2020 | Ciaramella et al. |
| 2020/0129615 A1 | 4/2020 | Ciaramella et al. |
| 2020/0163878 A1 | 5/2020 | Baumhof et al. |
| 2020/0239869 A1 | 7/2020 | Issa et al. |
| 2020/0254086 A1 | 8/2020 | Hoge et al. |
| 2020/0282047 A1 | 9/2020 | Ciaramella et al. |
| 2020/0297634 A1 | 9/2020 | Karmali et al. |
| 2020/0306191 A1 | 10/2020 | Schariter et al. |
| 2020/0338004 A1 | 10/2020 | Hansson et al. |
| 2020/0368162 A1 | 11/2020 | Martini |
| 2021/0046173 A1 | 2/2021 | Ciaramella et al. |
| 2021/0060175 A1 | 3/2021 | Baumhof et al. |
| 2021/0087135 A1 | 3/2021 | Benenato et al. |

(56) References Cited

U.S. PATENT DOCUMENTS

| | | |
|---|---|---|
| 2021/0162037 A1 | 6/2021 | Jasny et al. |
| 2021/0163919 A1 | 6/2021 | Issa et al. |
| 2021/0187097 A1 | 6/2021 | Ciaramella et al. |
| 2021/0206818 A1 | 7/2021 | Huang et al. |
| 2021/0217484 A1 | 7/2021 | Giessel et al. |
| 2021/0228707 A1 | 7/2021 | Mektar et al. |
| 2021/0268086 A1 | 9/2021 | Zhong et al. |
| 2021/0378980 A1 | 12/2021 | Horhota et al. |
| 2022/0031631 A1 | 2/2022 | Almarsson et al. |
| 2022/0047518 A1 | 2/2022 | Hennessy et al. |
| 2022/0054653 A1 | 2/2022 | Martini et al. |
| 2022/0062175 A1 | 3/2022 | Smith et al. |
| 2022/0125899 A1 | 4/2022 | Ashburn et al. |
| 2022/0145381 A1 | 5/2022 | Elich et al. |
| 2022/0236253 A1 | 7/2022 | Hopson |
| 2022/0241399 A1 | 8/2022 | Lusso et al. |
| 2022/0347292 A1 | 11/2022 | Panther et al. |
| 2022/0348900 A1 | 11/2022 | Shamashkin et al. |
| 2022/0349006 A1 | 11/2022 | Amato et al. |
| 2023/0000970 A1 | 1/2023 | Nachbagauer et al. |
| 2023/0142529 A1 | 5/2023 | White et al. |
| 2023/0181481 A1 | 6/2023 | White et al. |
| 2023/0190761 A1 | 6/2023 | Brader et al. |
| 2023/0212645 A1 | 7/2023 | Marquardt et al. |
| 2023/0287437 A1 | 9/2023 | Smith et al. |
| 2023/0338506 A1 | 10/2023 | Shaw et al. |
| 2023/0346914 A1 | 11/2023 | Stewart-Jones et al. |
| 2023/0355743 A1 | 11/2023 | Stewart-Jones et al. |
| 2024/0100145 A1 | 3/2024 | Bollman et al. |
| 2024/0100151 A1 | 3/2024 | Carfi et al. |
| 2024/0139309 A1 | 5/2024 | Carfi et al. |
| 2024/0173400 A1 | 5/2024 | Ciaramella et al. |
| 2024/0181030 A1 | 6/2024 | Himansu et al. |
| 2024/0207392 A1 | 6/2024 | Chandramouli et al. |
| 2024/0209068 A1 | 6/2024 | Deal et al. |
| 2024/0226028 A1 | 7/2024 | Goldman et al. |
| 2024/0226277 A1 | 7/2024 | Nachbagauer et al. |
| 2024/0229109 A1 | 7/2024 | Rabideau et al. |
| 2024/0238211 A1 | 7/2024 | Brader et al. |
| 2024/0263226 A1 | 8/2024 | Schmitt |
| 2024/0285754 A1 | 8/2024 | Stewart-Jones |
| 2024/0293534 A1 | 9/2024 | Stewart-Jones |
| 2024/0299531 A1 | 9/2024 | Stewart-Jones |
| 2024/0358819 A1 | 10/2024 | Stewart-Jones |
| 2024/0368580 A1 | 11/2024 | Geng et al. |
| 2024/0382581 A1 | 11/2024 | Stewart-Jones et al. |
| 2024/0383940 A1 | 11/2024 | Endo et al. |

FOREIGN PATENT DOCUMENTS

| | | |
|---|---|---|
| CA | 2473135 A1 | 6/2003 |
| CN | 110974954 A | 4/2020 |
| CN | 112546211 A | 3/2021 |
| EP | 1083232 B1 | 2/2005 |
| EP | 1301614 B1 | 11/2006 |
| EP | 1383556 B1 | 10/2007 |
| EP | 1905844 A2 | 4/2008 |
| EP | 1026253 B2 | 12/2012 |
| EP | 2188379 B1 | 1/2013 |
| EP | 2964608 A1 | 1/2016 |
| EP | 3083579 A1 | 10/2016 |
| EP | 3608308 A | 2/2020 |
| WO | WO 1990/011092 A1 | 10/1990 |
| WO | WO 1992/019752 A1 | 11/1992 |
| WO | WO 1999/052503 A2 | 10/1999 |
| WO | WO 2001/021810 A1 | 3/2001 |
| WO | WO 2004/058166 A2 | 7/2004 |
| WO | WO 2005/007689 A1 | 1/2005 |
| WO | 2007/024708 A2 | 3/2007 |
| WO | 2007/051303 A1 | 5/2007 |
| WO | WO 2007/094854 A2 | 8/2007 |
| WO | WO 2008/014979 A3 | 2/2008 |
| WO | WO 2008/052770 A2 | 5/2008 |
| WO | WO 2008/083949 A2 | 7/2008 |
| WO | 2008/143640 A1 | 11/2008 |
| WO | WO 2008/145129 A2 | 12/2008 |
| WO | 2009/127060 A1 | 10/2009 |
| WO | 2010/037539 A1 | 4/2010 |
| WO | WO 2010/037408 A1 | 4/2010 |
| WO | WO 2010/042877 A1 | 4/2010 |
| WO | WO 2010/054406 A1 | 5/2010 |
| WO | WO 2010/060430 A2 | 6/2010 |
| WO | WO 2010/088927 A1 | 8/2010 |
| WO | WO 2010/115046 A2 | 10/2010 |
| WO | 2010/148013 A2 | 12/2010 |
| WO | WO 2011/005799 A2 | 1/2011 |
| WO | 2011/068810 A1 | 6/2011 |
| WO | 2011/071931 A2 | 6/2011 |
| WO | WO 2011/069529 A1 | 6/2011 |
| WO | WO 2011/069586 A1 | 6/2011 |
| WO | WO 2012/024629 A1 | 8/2011 |
| WO | 2011/127255 A1 | 10/2011 |
| WO | WO 2011/140627 A1 | 11/2011 |
| WO | WO 2011/144358 A1 | 11/2011 |
| WO | 2011/150264 A2 | 12/2011 |
| WO | 2012/006372 A1 | 1/2012 |
| WO | 2012/006377 A2 | 1/2012 |
| WO | WO 2012/006369 A2 | 1/2012 |
| WO | WO 2012/006380 A2 | 1/2012 |
| WO | 2012/019168 A2 | 2/2012 |
| WO | WO 2012/019630 A1 | 2/2012 |
| WO | WO 2012/019780 A1 | 2/2012 |
| WO | 2012/030901 A1 | 3/2012 |
| WO | 2012/031046 A2 | 3/2012 |
| WO | 2012/045075 A1 | 4/2012 |
| WO | WO 2012/075040 A2 | 6/2012 |
| WO | 2012/092569 A2 | 7/2012 |
| WO | 2012/099805 A2 | 7/2012 |
| WO | WO 2012/089225 A1 | 7/2012 |
| WO | WO 2012/113513 A1 | 8/2012 |
| WO | WO 2012/116714 A1 | 9/2012 |
| WO | WO 2012/116715 A1 | 9/2012 |
| WO | WO 2012/116810 A1 | 9/2012 |
| WO | WO 2012/116811 A1 | 9/2012 |
| WO | 2012/135805 A2 | 10/2012 |
| WO | 2012/158736 A1 | 11/2012 |
| WO | 2012/170889 A1 | 12/2012 |
| WO | 2012/170930 A1 | 12/2012 |
| WO | WO 2013/006837 A1 | 1/2013 |
| WO | WO 2013/006838 A1 | 1/2013 |
| WO | WO 2013/006842 A2 | 1/2013 |
| WO | WO 2013/030778 A2 | 3/2013 |
| WO | 2013/052523 A1 | 4/2013 |
| WO | WO 2013/052167 A2 | 4/2013 |
| WO | WO 2013/056132 A2 | 4/2013 |
| WO | WO 2013/059496 A1 | 4/2013 |
| WO | 2013/075266 A1 | 5/2013 |
| WO | 2013/090186 A1 | 6/2013 |
| WO | WO 2013/090648 A1 | 6/2013 |
| WO | WO 2013/113502 A1 | 8/2013 |
| WO | 2013/143555 A1 | 10/2013 |
| WO | 2013/151663 A1 | 10/2013 |
| WO | 2013/151664 A1 | 10/2013 |
| WO | 2013/151665 A2 | 10/2013 |
| WO | 2013/151666 A2 | 10/2013 |
| WO | 2013/151667 A1 | 10/2013 |
| WO | 2013/151668 A1 | 10/2013 |
| WO | 2013/151669 A1 | 10/2013 |
| WO | 2013/151670 A2 | 10/2013 |
| WO | 2013/151671 A1 | 10/2013 |
| WO | 2013/151672 A2 | 10/2013 |
| WO | 2013/151736 A1 | 10/2013 |
| WO | WO 2013/174409 A1 | 11/2013 |
| WO | 2013/185069 A1 | 12/2013 |
| WO | 2014/081507 A1 | 5/2014 |
| WO | WO 2014/071963 A1 | 5/2014 |
| WO | WO 2014/072061 A1 | 5/2014 |
| WO | 2014/093574 A1 | 6/2014 |
| WO | WO 2014/089239 A1 | 6/2014 |
| WO | WO 2014/127917 A1 | 8/2014 |
| WO | 2014/152211 A1 | 9/2014 |
| WO | 2014/152540 A1 | 9/2014 |
| WO | WO 2014/144711 A1 | 9/2014 |
| WO | WO 2014/152030 A1 | 9/2014 |

(56) References Cited

FOREIGN PATENT DOCUMENTS

| | | |
|---|---|---|
| WO | WO 2014/159813 A1 | 10/2014 |
| WO | WO 2014/160243 A1 | 10/2014 |
| WO | 2015/006747 A2 | 1/2015 |
| WO | WO 2015/005253 A1 | 1/2015 |
| WO | WO 2015/013551 A1 | 1/2015 |
| WO | 2015/023461 A2 | 2/2015 |
| WO | WO 2015/024667 A1 | 2/2015 |
| WO | WO 2015/024668 A2 | 2/2015 |
| WO | WO 2015/024669 A1 | 2/2015 |
| WO | 2015/048744 A2 | 4/2015 |
| WO | WO 2015/164674 A1 | 4/2015 |
| WO | WO 2015/085318 A2 | 6/2015 |
| WO | WO 2015/095346 A1 | 6/2015 |
| WO | WO 2015/149944 A2 | 10/2015 |
| WO | WO 2015/189425 A1 | 12/2015 |
| WO | WO 2015/199952 A1 | 12/2015 |
| WO | WO 2016/164762 A1 | 10/2016 |
| WO | WO 2020/061367 A1 | 10/2016 |
| WO | WO 2016/176330 A1 | 11/2016 |
| WO | WO 2016/201377 A1 | 12/2016 |
| WO | WO 2016/203025 A1 | 12/2016 |
| WO | WO 2017/011773 A2 | 1/2017 |
| WO | WO 2017/015457 A1 | 1/2017 |
| WO | WO 2017/020026 A1 | 2/2017 |
| WO | WO 2017/062513 A1 | 4/2017 |
| WO | WO 2017/066789 A1 | 4/2017 |
| WO | WO 2017/070601 A1 | 4/2017 |
| WO | WO 2017/070618 A1 | 4/2017 |
| WO | WO 2017/070620 A1 | 4/2017 |
| WO | WO 2017/070623 A1 | 4/2017 |
| WO | WO 2017/075531 A1 | 5/2017 |
| WO | WO 2017/081082 A1 | 5/2017 |
| WO | WO 2017/112865 A1 | 6/2017 |
| WO | WO 2017/127750 A1 | 7/2017 |
| WO | WO 2017/191258 A1 | 11/2017 |
| WO | WO 2017/201333 A1 | 11/2017 |
| WO | WO 2017/201340 A1 | 11/2017 |
| WO | WO 2017/201342 A1 | 11/2017 |
| WO | WO 2017/201347 A1 | 11/2017 |
| WO | WO 2018/053209 A1 | 3/2018 |
| WO | WO 2018/075592 A1 | 4/2018 |
| WO | WO 2018/075980 A1 | 4/2018 |
| WO | WO 2018/081459 A1 | 5/2018 |
| WO | WO 2018/089851 A1 | 5/2018 |
| WO | WO 2018/107088 A1 | 6/2018 |
| WO | WO 2018/111967 A1 | 6/2018 |
| WO | WO 2018/144082 A1 | 8/2018 |
| WO | WO 2018/144778 A1 | 8/2018 |
| WO | WO 2018/151816 A1 | 8/2018 |
| WO | WO 2018/157009 A1 | 8/2018 |
| WO | WO 2018/170245 A1 | 9/2018 |
| WO | WO 2018/170256 A1 | 9/2018 |
| WO | WO 2018/170260 A1 | 9/2018 |
| WO | WO 2018/170270 A1 | 9/2018 |
| WO | WO 2018/170347 A1 | 9/2018 |
| WO | WO 2018/175783 A1 | 9/2018 |
| WO | WO 2018/187590 A2 | 10/2018 |
| WO | WO 2018/200737 A1 | 11/2018 |
| WO | WO 2018/232355 A1 | 12/2018 |
| WO | WO 2018/232357 A1 | 12/2018 |
| WO | WO 2019/018765 A1 | 1/2019 |
| WO | WO 2019/036670 A1 | 2/2019 |
| WO | WO 2019/036682 A1 | 2/2019 |
| WO | WO 2019/036683 A1 | 2/2019 |
| WO | WO 2019/036685 A1 | 2/2019 |
| WO | WO 2019/103993 A1 | 5/2019 |
| WO | WO 2019/148101 A1 | 8/2019 |
| WO | WO 2020/006242 A1 | 1/2020 |
| WO | WO 2020/056370 A1 | 3/2020 |
| WO | WO 2020/061284 A1 | 3/2020 |
| WO | WO 2020/061295 A1 | 3/2020 |
| WO | WO 2020/097291 A1 | 5/2020 |
| WO | WO 2020/163719 A2 | 8/2020 |
| WO | WO 2020/172239 A1 | 8/2020 |
| WO | WO 2020/185811 A1 | 9/2020 |
| WO | WO 2020/190750 A1 | 9/2020 |
| WO | WO 2020/243561 A1 | 12/2020 |
| WO | WO 2021/016430 A1 | 1/2021 |
| WO | WO 2021/030533 A1 | 2/2021 |
| WO | 2021/055849 A1 | 3/2021 |
| WO | WO 2021/050864 A1 | 3/2021 |
| WO | WO 2021/155243 A1 | 8/2021 |
| WO | WO 2021/155274 A1 | 8/2021 |
| WO | WO 2021/159040 A2 | 8/2021 |
| WO | WO 2021/159130 A2 | 8/2021 |
| WO | WO 2021/204175 A1 | 10/2021 |
| WO | WO 2021/211343 A1 | 10/2021 |
| WO | WO 2021/222304 A1 | 11/2021 |
| WO | WO 2021/231929 A1 | 11/2021 |
| WO | WO 2021/231963 A1 | 11/2021 |
| WO | WO 2021/237084 A1 | 11/2021 |
| WO | WO 2021/239880 A1 | 12/2021 |
| WO | WO 2021/247817 A1 | 12/2021 |
| WO | WO 2022/009121 A1 | 1/2022 |
| WO | WO 2022/032154 A2 | 2/2022 |
| WO | WO 2022/067010 A1 | 3/2022 |
| WO | WO 2022/076562 A1 | 4/2022 |
| WO | WO 2022/099003 A1 | 5/2022 |
| WO | WO 2022/101469 A1 | 5/2022 |
| WO | WO 2022/155524 A1 | 7/2022 |
| WO | WO 2022/155530 A1 | 7/2022 |
| WO | 2022/200575 | 9/2022 |
| WO | WO 2022/187698 A1 | 9/2022 |
| WO | WO 2022/197624 A1 | 9/2022 |
| WO | WO 2022/204491 A1 | 9/2022 |
| WO | WO 2022/212191 A1 | 10/2022 |
| WO | WO 2022/212442 A1 | 10/2022 |
| WO | WO 2022/212711 A2 | 10/2022 |
| WO | WO 2022/221335 A1 | 10/2022 |
| WO | WO 2022/221336 A1 | 10/2022 |
| WO | WO 2022/221359 A1 | 10/2022 |
| WO | WO 2022/221440 A1 | 10/2022 |
| WO | WO 2022/226277 A1 | 10/2022 |
| WO | WO 2022/226318 A1 | 10/2022 |
| WO | 2022/234417 | 11/2022 |
| WO | WO 2022/232585 A1 | 11/2022 |
| WO | WO 2022/241103 A1 | 11/2022 |
| WO | WO 2022/245888 A1 | 11/2022 |
| WO | WO 2022/266010 A1 | 12/2022 |
| WO | WO 2022/266012 A1 | 12/2022 |
| WO | WO 2022/266389 A1 | 12/2022 |
| WO | WO 2023/274860 A1 | 1/2023 |
| WO | WO 2023/283642 A2 | 1/2023 |
| WO | WO 2023/283645 A1 | 1/2023 |
| WO | WO 2023/283651 A1 | 1/2023 |
| WO | WO 2023/014649 A1 | 2/2023 |
| WO | WO 2023/018773 A1 | 2/2023 |
| WO | WO 2023/018923 A1 | 2/2023 |
| WO | WO 2023/019181 A1 | 2/2023 |
| WO | WO 2023/056401 A1 | 4/2023 |
| WO | WO 2023/069625 A1 | 4/2023 |
| WO | WO 2023/069895 A1 | 4/2023 |
| WO | WO 2023/069900 A1 | 4/2023 |
| WO | WO 2023/076358 A1 | 5/2023 |
| WO | WO 2023/076658 A1 | 5/2023 |
| WO | WO 2023/081311 A1 | 5/2023 |
| WO | WO 2023/092069 A1 | 5/2023 |
| WO | WO 2023/107999 A2 | 6/2023 |
| WO | WO 2023/114307 A1 | 6/2023 |
| WO | WO2023/132885 A1 | 7/2023 |
| WO | WO2023/137149 A1 | 7/2023 |
| WO | WO 2023/150256 A1 | 8/2023 |
| WO | WO 2023/154818 A1 | 8/2023 |
| WO | WO 2023/196914 A1 | 10/2023 |
| WO | WO 2023/201204 A1 | 10/2023 |
| WO | WO 2023/201294 A1 | 10/2023 |
| WO | WO 2023/201296 A1 | 10/2023 |
| WO | WO 2023/212696 A1 | 11/2023 |
| WO | WO 2023/225524 A1 | 11/2023 |
| WO | WO 2023/250119 A1 | 12/2023 |
| WO | WO 2024/010993 A1 | 1/2024 |
| WO | WO 2024/015890 A1 | 1/2024 |
| WO | WO 2024/026005 A1 | 2/2024 |
| WO | WO 2024/030369 A1 | 2/2024 |

(56) References Cited

FOREIGN PATENT DOCUMENTS

| WO | WO 2024/050483 A1 | 3/2024 |
|---|---|---|
| WO | WO 2024/097874 A1 | 5/2024 |
| WO | WO 2024/123978 A1 | 6/2024 |
| WO | WO 2024/151811 A1 | 7/2024 |
| WO | WO 2024/163465 A1 | 8/2024 |
| WO | 2024/191860 | 9/2024 |
| WO | 2024/206835 | 10/2024 |
| WO | 2024/215721 | 10/2024 |

OTHER PUBLICATIONS

U.S. Appl. No. 18/314,980, filed May 10, 2023, Ciaramella et al.
U.S. Appl. No. 15/767,618, filed Apr. 11, 2018, Ciaramella et al.
U.S. Appl. No. 17/590,479, filed Feb. 1, 2022, Ciaramella et al.
U.S. Appl. No. 16/897,859, filed Jun. 10, 2020, Ciaramella et al.
U.S. Appl. No. 17/737,532, filed May 5, 2022, Ciaramella et al.
U.S. Appl. No. 17/839,401, filed Jun. 13, 2022, Ciaramella et al.
U.S. Appl. No. 16/897,734, filed Jun. 10, 2020, Ciaramella et al.
U.S. Appl. No. 18/189,512, filed Mar. 24, 2023, Ciaramella et al.
U.S. Appl. No. 18/055,193, filed Nov. 14, 2022, Ciaramella et al.
U.S. Appl. No. 16/494,130, filed Sep. 13, 2019, Ciaramella et al.
U.S. Appl. No. 18/354,574, filed Jul. 18, 2023, Ciaramella et al.
U.S. Appl. No. 17/823,255, filed Aug. 30, 2022, Ciaramella et al.
U.S. Appl. No. 17/245,973, filed Apr. 30, 2021, Ciaramella.
U.S. Appl. No. 17/938,823, filed Oct. 7, 2022, Ciaramella et al.
U.S. Appl. No. 16/765,285, filed May 19, 2020, Ciaramella et al.
U.S. Appl. No. 17/531,211, filed Nov. 19, 2021, Ciaramella et al.
U.S. Appl. No. 16/965,589, filed Jul. 28, 2020, Ciaramella et al.
U.S. Appl. No. 17/439,198, filed Sep. 14, 2021, Lusso et al.
U.S. Appl. No. 17/737,581, filed May 5, 2022, Panther et al.
U.S. Appl. No. 17/641,967, filed Mar. 10, 2022, John et al.
U.S. Appl. No. 17/840,478, filed Jun. 14, 2022, Kramarczyk et al.
U.S. Appl. No. 17/796,401, filed Jul. 29, 2022, Shaw et al.
U.S. Appl. No. 17/797,784, filed Aug. 5, 2022, Stewart-Jones et al.
U.S. Appl. No. 18/028,126, filed Mar. 23, 2023, Stewart-Jones et al.
U.S. Appl. No. 17/572,465, filed Jan. 10, 2022, Nachbagauer et al.
U.S. Appl. No. 18/272,512, filed Jul. 14, 2023, Carfi et al.
U.S. Appl. No. 18/272,496, filed Jul. 14, 2023, Carfi et al.
U.S. Appl. No. 18/351,843, filed Jul. 13, 2023, Bollman et al.
U.S. Appl. No. 18/351,057, filed Jul. 12, 2023, Bollman et al.
U.S. Appl. No. 18/335,949, filed Jun. 15, 2023, Nasir et al.
PCT/US2017/061182, May 15, 2018, International Search Report and Written Opinion.
International Search Report and Written Opinion for Application No. PCT/US2017/061182, mailed May 15, 2018.
[No Author Listed], "Moderna's (MRNA) Flu Vaccine Data Fails to Impress Investors", Dec. 13, 2021 (Dec. 13, 2021), pp. 1-6. Retrieved from the Internet: URL:https://finance.yahoo.com/news/moderna s-mrna-flu-vaccine-data-153303228.html?guccounter= 1&guce_referrer=aHR0cHM6Ly93d3cuZ29vZ2xlLmNvbS8&guce_referrer_sig=AQAAAJpn3p7IiHi5Gppdr9ckD_ a8FxRTr2MtUAQeqDz37PFJp8H_ QTbC2SKOslbb28wvm7kJTQJcRAdYVNfcXSBAeWKrKR Y4HMdkSZGaWdx2fMpYlwKaeGuc4iW6N8k- 60f8R7YTHZilNunaCU.
URL:https://finance.yahoo.com/news/moderna s-mrna-flu-vaccine-data-153303228.html?guccounter=1&guce_referrer= aHR0cHM6Ly93d3cuZ29vZ2xlLmNvbS8&guce_referrer_sig= AQAAAJpn3p7IiHi5Gppdr9ckD_a8FxRTr2MtUAQeqDz37PFJp8H_ QTbC2SKOslbb28wvm7kJTQJcRAdYVNfcXSBAeWKrKR Y4HMdkSZGaWdx2fMpYlwKaeGuc4iW6N8k- 60f8R7YTHZilNunaCU.
Andries et al., N(1)-methylpseudouridine-incorporated mRNA outperforms pseudouridine-incorporated mRNA by providing enhanced protein expression and reduced immunogenicity in mammalian cell lines and mice. J Control Release. Nov. 10, 2015;217:337-44. doi: 10.1016/j.jconrel.2015.08.051. Epub Sep. 3, 2015.

[No Author Listed], Influenza A virus A/Jiangxi/LPB13/ 2013(H10N8) hemagglutinin protein. UniProtKB Accession: A0A059T4A1. Sep. 3, 2014. 1 page.
Bahl et al., Preclinical and Clinical Demonstration of Immunogenicity by mRNA Vaccines against H10N8 and H7N9 Influenza Viruses. Mol Ther. Jun. 7, 2017;25(6):1316-1327. doi: 10.1016/j.ymthe.2017. 03.035. Epub Apr. 27, 2017.
Bentebibel et al., ICOS(+)PD-1(+)CXCR3(+) T follicular helper cells contribute to the generation of high-avidity antibodies following influenza vaccination. Sci Rep. May 27, 2016;6:26494. doi: 10.1038/srep26494.
Bommakanti et al., Design of an HA2-based *Escherichia coli* expressed influenza immunogen that protects mice from pathogenic challenge. Proc Natl Acad Sci U S A. Aug. 3, 2010;107(31):13701- 6. doi: 10.1073/pnas.1007465107. Epub Jul. 6, 2010.
Bowie et al., Deciphering the message in protein sequences: tolerance to amino acid substitutions. Science. Mar. 16, 1990;247(4948):1306-10.
Brito et al., A cationic nanoemulsion for the delivery of next-generation RNA vaccines. Mol Ther. Dec. 2014;22(12):2118-29. doi: 10.1038/mt.2014.133. Epub Jul. 16, 2014.
[No Author Listed], World Health Organization: "Recommended composition of influenza virus vaccines for use in the 2021 southern hemisphere influenza season", Sep. 25, 2020 (Sep. 25, 2020), pp. 1-9, Retrieved from the Internet: https://iris.who.int/bitstream/handle/ 10665/336145/WER9542-497-508-eng-fre.pdf.
Buschmann et al., Nanomaterial Delivery Systems for mRNA Vaccines. Vaccines (Basel). Jan. 19, 2021;9(1):65. doi: 10.3390/ vaccines9010065.
Chen et al., Clinical and epidemiological characteristics of a fatal case of avian influenza A H10N8 virus infection: a descriptive study. Lancet. Feb. 22, 2014;383(9918):714-21. doi: 10.1016/S0140- 6736(14)60111-2. Epub Feb. 5, 2014.
Chaudhary et al., mRNA vaccines for infectious diseases: principles, delivery and clinical translation. Nature Reviews Drug Discovery vol. 20, pp. 817-838 (2021).
Cheng et al., Multifunctional triblock copolymers for intracellular messenger RNA delivery. Biomaterials. Oct. 2012; 33(28): 6868- 6876.
Chen et al., Vaccine design of hemagglutinin glycoprotein against influenza. Trends Biotechnol. Sep. 2011;29(9):426-34. doi: 10.1016/ j.tibtech.2011.04.007.
Cu et al., Enhanced Delivery and Potency of Self-Amplifying mRNA Vaccines by Electroporation in Situ, Vaccines, 2013, 1, 367-383. Abstract Only.
Cullis et al., Lipid Nanoparticle Systems for Enabling Gene Therapies. Mol Ther. Jul. 5, 2017;25(7):1467-1475. doi: 10.1016/j.ymthe. 2017.03.013. Epub Apr. 13, 2017.
Deering et al., Nucleic acid vaccines: prospects for non-viral delivery of mRNA vaccines.Expert Opin Drug Deliv. Jun. 2014; 11(6):885-99. doi: 10.1517/17425247.2014.901308. Epub Mar. 26, 2014.
Dicaro et al., In Vivo Delivery of Nucleic Acid-Formulated Microparticles as a Potential Tolerogenic Vaccine for Type 1 Diabetes. Rev Diabet Stud. 2012 Winter;9(4):348-56.
Diken et al., Current Developments in Actively Personalized Cancer Vaccination with a Focus on RNA as the Drug Format. Prog Tumor Res. 2015;42:44-54. doi: 10.1159/000437184. Epub Sep. 4, 2015. Review.
Cox et al., FluBlok, a recombinant hemagglutinin influenza vaccine. Influenza Other Respir Viruses. Nov. 2008; 2(6): 211-219.
Dolgin, mRNA flu shots move into trials. Nature Reviews Drug Discovery 20, 801-803 (2021).
Ernsting et al., Factors controlling the pharmacokinetics, biodistribution and intratumoral penetration of nanoparticles. J Control Release. Dec. 28, 2013;172(3):782-94. doi: 10.1016/j.jconrel.2013.09.013. Epub Sep. 25, 2013.
Fleeton et al., Self-replicative RNA vaccines elicit protection against influenza A virus, respiratory syncytial virus, and a tickborne encephalitis virus. J Infect Dis. May 1, 2001;183(9):1395-8. Epub Mar. 30, 2001.
Ellebedy et al., Influenza Vaccines. Vaccine. Nov. 5, 2009; 27(Suppl 4): D65-D68.

(56) References Cited

OTHER PUBLICATIONS

Gao et al., Human infection with a novel avian-origin influenza A (H7N9) virus. N Engl J Med. May 16, 2013;368(20):1888-97. doi: 10.1056/NEJMoa1304459. Epub Apr. 11, 2013.

Geall et al., Nonviral delivery of self-amplifying RNA vaccines. Proc Natl Acad Sci U S A. Sep. 4, 2012;109(36):14604-9. doi: 10.1073/pnas.1209367109. Epub Aug. 20, 2012.

Freyn et al., A Multi-Targeting, Nucleoside-Modified mRNA Influenza Virus Vaccine Provides Broad Protection in Mice. Mol Ther. Jul. 8, 2020;28(7):1569-1584. doi: 10.1016/j.ymthe.2020.04.018. Epub Apr. 19, 2020.

Hadinoto et al., Lipid-polymer Hybrid Nanoparticles as a New Generation Therapeutic Delivery Platform: A Review. Eur J Pharm Biopharm. Nov. 2013;85(3 Pt A):427-43. doi: 10.1016/j.ejpb.2013.07.002. Epub Jul. 17, 2013.

Hekele et al., Rapidly produced SAM(®) vaccine against H7N9 influenza is immunogenic in mice. Emerg Microbes Infect. Aug. 2013;2(8):e52. doi: 10.1038/emi.2013.54. Epub Aug. 14, 2013.

Holtkamp et al., Modification of antigen-encoding RNA increases stability, translational efficacy, and T-cell stimulatory capacity of dendritic cells. Blood. Dec. 15, 2006;108(13):4009-17.

Hörr, RNA vaccine for the induction of specific cytotoxic T lymphocytes (CTL) and antibodies. Eberhard Karls University of Tübingen. Dissertation. English-Language Translation. 1999. 138 Pages.

Geall et al., RNA: the new revolution in nucleic acid vaccines. Semin Immunol. Apr. 2013;25(2):152-9. doi: 10.1016/j.smim.2013.05.001. Epub Jun. 2, 2013.

Hou et al., Lipid nanoparticles for mRNA delivery. Nature Reviews Materials vol. 6, pp. 1078-1094 (2021).

Kallen et al., A development that may evolve into a revolution in medicine: mRNA as the basis for novel, nucleotide-based vaccines and drugs. Ther Adv Vaccines. Jan. 2014;2(1):10-31. doi: 10.1177/2051013613508729.

Kauffman et al., Efficacy and immunogenicity of unmodified and pseudouridine-modified mRNA delivered systemically with lipid nanoparticles in vivo. Biomaterials. Dec. 2016;109:78-87. doi: 10.1016/j.biomaterials.2016.09.006. Epub Sep. 25, 2016.

Kauffman et al., Materials for non-viral intracellular delivery of messenger RNA therapeutics. J Control Release. Oct. 28, 2016;240:227-234. doi: 10.1016/j.jconrel.2015.12.032. Epub Dec. 21, 2015.

Khurana et al., Recombinant HA1 produced in E. coli forms functional oligomers and generates strain-specific SRID potency antibodies for pandemic influenza vaccines. Vaccine. Aug. 5, 2011;29(34):5657-65. doi: 10.1016/j.vaccine.2011.06.014. Epub Jun. 23, 2011.

Knepper et al., The novel human influenza A(H7N9) virus is naturally adapted to efficient growth in human lung tissue. MBio. Oct. 8, 2013;4(5):e00601-13. doi: 10.1128/mBio.00601-13.

Kopera et al., Expression, purification and characterization of glycosylated influenza H5N1 hemagglutinin produced in Pichia pastoris. Acta Biochim Pol. 2014;61(3):597-602. Epub Sep. 12, 2014.

Houser et al., Influenza Vaccines: Challenges and Solutions. Cell Host Microbe. Mar. 11, 2015; 17(3): 295-300. doi: 10.1016/j.chom.2015.02.012.

Krammer et al., Chimeric hemagglutinin influenza virus vaccine constructs elicit broadly protective stalk-specific antibodies. J Virol. Jun. 2013;87(12):6542-50. doi: 10.1128/JVI.00641-13. Epub Apr. 10, 2013.

Kuhn et al., mRNA as a versatile tool for exogenous protein expression. Current Gene Therapy. Oct. 2012; 12 (5): 347-361.

Kurimoto et al., PEG-OligoRNA Hybridization of mRNA for Developing Sterically Stable Lipid Nanoparticles toward In Vivo Administration. Molecules. Apr. 3, 2019;24(7):1303. doi: 10.3390/molecules24071303.

Leitner et al., DNA and RNA-based vaccines: principles, progress and prospects. Vaccine. Dec. 10, 1999;18 (9-10):765-77.

Leroueil et al., Wide varieties of cationic nanoparticles induce defects in supported lipid bilayers. Nano Lett. Feb. 2008;8(2):420-4. doi: 10.1021/nl0722929. Epub Jan. 25, 2008.

Kramps et al., Messenger RNA-based vaccines: progress, challenges, applications. Wiley Interdiscip Rev RNA. Nov.-Dec. 2013;4(6):737-49. doi: 10.1002/wrna.1189. Epub Jul. 25, 2013.

Li et al., Prophylactic, therapeutic and immune enhancement effect of liposome-encapsulated PolyICLC on highly pathogenic H5N1 influenza infection. J Gene Med. Jan. 2011;13(1):60-72. doi: 10.1002/jgm.1536.

Lian et al., Trends and developments in liposome drug delivery systems. J Pharm Sci. Jun. 2001;90(6):667-80.

Liang et al., Efficient Targeting and Activation of Antigen-Presenting Cells In Vivo after Modified mRNA Vaccine Administration in Rhesus Macaques. Mol Ther. Dec. 6, 2017;25(12):2635-2647. doi: 10.1016/j.ymthe.2017.08.006. Epub Aug. 12, 2017.

Lindgren et al., Induction of Robust B Cell Responses after Influenza mRNA Vaccination Is Accompanied by Circulating Hemagglutinin-Specific ICOS+ PD-1+ CXCR3+ T Follicular Helper Cells. Front Immunol. Nov. 13, 2017;8:1539. doi: 10.3389/fimmu.2017.01539. eCollection 2017.

Lorenzi et al., Intranasal vaccination with messenger RNA as a new approach in gene therapy: Use against tuberculosis. BMC Biotechnol. Oct. 2010; 10(77): 1-11.

MacLachlan, Lipid Nanoparticle-mediated delivery of messenger RNA. Presentation. 1st International mRNA Health Conference. Tubingen, Germany. Oct. 24, 2013. http://files.shareholder.com/downloads/ABEA-50QJTB/2628241206x0x699789/47543d12-db34-4e6e-88a9-f3ae5d97b1d2/MacLachlan_mRNA_Conf_2013.pdf. Last accessed Dec. 22, 2016.

Madden et al., Systemic delivery of mRNA therapeutics using lipid nanoparticles (LNP): improved potency for novel LNP and influence of route of administration on protein expression. 2nd International mRNA Health Conference. Nov. 12, 2014. https://acuitastx.com/wp-content/uploads/2015/01/Poster-Second-International-mRNA-Health-Conference.pdf. 1 page.

Magini et al., Self-Amplifying mRNA Vaccines Expressing Multiple Conserved Influenza Antigens Confer Protection against Homologous and Heterosubtypic Viral Challenge. PLoS One. Aug. 15, 2016;11(8):e0161193. doi: 10.1371/journal.pone.0161193. eCollection 2016.

Martinon et al., Induction of virus-specific cytotoxic T lymphocytes in vivo by liposome-entrapped mRNA. Eur J Immunol. Jul. 1993;23(7):1719-22.

Li et al., Lipid-based nanoparticles for nucleic acid delivery. Pharm Res. Mar. 2007;24(3):438-49. doi: 10.1007/s11095-006-9180-5.

McKenzie et al., Nucleic acid vaccines: tasks and tactics. Immunol Res. 2001 ;24(3):225-44.

Midoux et al., Lipid-based mRNA vaccine delivery systems. Expert Rev Vaccines. Feb. 2015;14(2):221-34. doi: 10.1586/14760584.2015.986104. Epub Dec. 26, 2014. Review.

Mitchell et al., RNA transfected dendritic cells as cancer vaccines. Curr Opin Mol Ther. Apr. 2000;2(2):176-81.

Mockey et al., mRNA-based cancer vaccine: prevention of B16 melanoma progression and metastasis by systemic injection of MART1 mRNA histidylated lipopolyplexes. Cancer Gene Ther. Sep. 2007;14(9):802-14. Epub Jun. 22, 2007.

Munster et al., Hemagglutinin [Influenza A virus (A/mallard/Sweden/91/2002(H7N9))]. GenBank: AAY46211.1. Dep. Sep. 30, 2005.

Pardi et al., Developing an influenza vaccine using lipid nanoparticle-encapsulated nucleoside-modified mRNA. Eur. J. Immunol. Aug. 2016; 46(S1):1232-1233. Abstract 1349.

Pardi et al., mRNA vaccines—a new era in vaccinology. Nat Rev Drug Discov. Apr. 2018;17(4):261-279. doi: 10.1038/nrd.2017.243. Epub Jan. 12, 2018.

Maruggi et al., mRNA as a Transformative Technology for Vaccine Development to Control Infectious Diseases. Mol Ther. Apr. 10, 20190;27(4):757-772. doi: 10.1016/j.ymthe.2019.01.020. Epub Feb. 7, 2019.

Petsch et al., Protective efficacy of in vitro synthesized, specific mRNA vaccines against influenza A virus infection. Nat Biotechnol. Dec. 2012;30(12):1210-6. doi: 10.1038/nbt.2436. Epub Nov. 25, 2012.

Pollard et al., Type I IFN counteracts the induction of antigen-specific immune responses by lipid-based delivery of mRNA vaccines. Mol Ther. Jan. 2013; 21 (1): 251-259.

(56) References Cited

OTHER PUBLICATIONS

Poveda et al., Establishing Preferred Product Characterization for the Evaluation of RNA Vaccine Antigens. Vaccines (Basel). Sep. 27, 2019;7(4):131. doi: 10.3390/vaccines7040131.
Reichmuth et al., mRNA Vaccine Delivery Using Lipid Nanoparticles. Ther Deliv. 2016;7(5):319-34. doi: 10.4155/tde-2016-0006.
Patel et al., Naturally-occurring cholesterol analogues in lipid nanoparticles induce polymorphic shape and enhance intracellular delivery of mRNA. Nat Commun. Feb. 20, 2020;11(1):983. doi: 10.1038/s41467-020-14527-2.
Schirrmacher et al., Intra-pinna anti-tumor vaccination with self-replicating infectious RNA or with DNA encoding a model tumor antigen and a cytokine. Gene Ther. Jul. 2000;7(13):1137-47.
Schlake et al., Developing mRNA-vaccine technologies. RNA Biol. Nov. 2012;9(11):1319-30. doi: 10.4161/rna.22269. Epub Oct. 12, 2012.
Schott et al., Viral and non-viral approaches for transient delivery of mRNA and proteins. Current Gene Ther. 2011; 11 (5): 382-398.
Rodriguez-Gascon et al., Development of nucleic acid vaccines: use of self-amplifying RNA in lipid nanoparticles. Int J Nanomedicine. 2014; 9: 1833-1843.
Sirin et al. AB-Bind: Antibody binding mutational database for computational affinity predictions. Protein Sci. Feb. 2016;25(2):393-409. doi: 10.1002/pro.2829. Epub Nov. 6, 2015.
Stab et al., Protective efficacy and immunogenicity of a combinatory DNA vaccine against Influenza A Virus and the Respiratory Syncytial Virus. PLoS One. Aug. 14, 2013;8(8):e72217. doi: 10.1371/journal.pone.0072217. eCollection 2013.
Szebeni et al., Activation of complement by therapeutic liposomes and other lipid excipient-based therapeutic products: prediction and prevention. Adv Drug Deliv Rev. Sep. 16, 2011;63(12):1020-30. doi: 10.1016/j.addr.2011.06.017. Epub Jul. 14, 2011.
Szebeni et al., Complement activation as a bioequivalence issue relevant to the development of generic liposomes and other nanoparticulate drugs. Biochem Biophys Res Commun. Dec. 18, 2015;468(3):490-7. doi: 10.1016/j.bbrc.2015.06.177. Epub Jul. 14, 2015.
Szebeni, Complement activation-related pseudoallergy: a stress reaction in blood triggered by nanomedicines and biologicals. Mol Immunol. Oct. 2014;61(2):163-73. doi: 10.1016/j.molimm.2014.06.038. Epub Aug. 12, 2014.
Shin et al., Recent Advances in RNA Therapeutics and RNA Delivery Systems Based on Nanoparticles. Adv. Therap., Nov. 2018;1(7):1800065. Review.
Thess et al., Sequence-engineered mRNA Without Chemical Nucleoside Modifications Enables an Effective Protein Therapy in Large Animals. Mol Ther. Sep. 2015;23(9):1456-64.doi: 10.1038/mt.2015.103. Epub Jun. 8, 2015.
Terada et al., Characterization of Lipid Nanoparticles Containing Ionizable Cationic Lipids Using Design-of-Experiments Approach. Langmuir. Jan. 26, 2021;37(3):1120-1128. doi: 10.1021/acs.langmuir.0c03039. Epub Jan. 13, 2021.
Torrecilla et al., Lipid Nanoparticles as Carriers for RNAi Against Viral Infections: Current Status and Future Perspectives. Biomed Res Int. 2014;2014:161794. doi: 10.1155/2014/161794. Epub Aug. 12, 2014.
To et al., An overview of rational design of mRNA-based therapeutics and vaccines. Expert Opin Drug Discov. Nov. 2021;16(11):1307-1317. doi: 10.1080/17460441.2021.1935859. Epub Jul. 19, 2021.
Vassilev et al., Microparticle-mediated RNA immunization against bovine viral diarrhea virus. Vaccine. Feb. 28, 2001;19(15-16):2012-9.
Wang et al., Hemagglutinin (HA) proteins from H1 and H3 serotypes of influenza A viruses require different antigen designs for the induction of optimal protective antibody responses as studied by codon-optimized HA DNA vaccines. J Virol. Dec. 2006;80(23):11628-37. Epub Sep. 20, 2006.
Wang et al., Systemic delivery of modified mRNA encoding herpes simplex virus 1 thymidine kinase for targeted cancer gene therapy. Mol Ther. Feb. 2013;21(2):358-67. doi: 10.1038/mt.2012.250. Epub Dec. 11, 2012.
Weilhammer et al., The use of nanolipoprotein particles to enhance the immunostimulatory properties of innate immune agonists against lethal influenza challenge. Biomaterials. Dec. 2013;34(38):10305-18. doi: 10.1016/j.biomaterials.2013.09.038. Epub Sep. 27, 2013.
Ulmer et al., RNA-based vaccines. Vaccine. Jun. 22, 2012;30(30):4414-8. doi: 10.1016/j.vaccine.2012.04.060. Epub Apr. 28, 2012.
Wentworth et al., Hemagglutinin [Influenza A virus (A/Anhui/DEWH72-01/2013(H7N9))]. Gen Bank: AHZ39686.1. Dep. May 9, 2014.
Winkler et al., Changing the antigen binding specificity by single point mutations of an anti-p24 (HIV-1) antibody. J Immunol. Oct. 15, 2000;165(8):4505-14.
Wong et al., An mRNA vaccine for influenza. Nat Biotechnol. Dec. 2012;30(12):1202-4. doi: 10.1038/nbt.2439.
Weissman, mRNA transcript therapy. Expert Rev Vaccines. Feb. 2015;14(2):265-81. doi: 10.1586/14760584.2015.973859. Epub Oct. 31, 2014.
Woodle et al., Sterically stabilized liposomes. Biochim Biophys Acta. Aug. 14, 1992;1113(2):171-99. doi: 10.1016/0304-4157(92)90038-c.
URL:https://www.who.int/publications/m/item/recommended-composition-of-influenza-virus-vaccines-for-use-in-the-2022-southern-hemisphere-influenza-season.
Yamamoto et al., Current prospects for mRNA gene delivery. Eur J Pharm Biopharm. Mar. 2009;71(3):484-9. doi: 10.1016/j.ejpb.2008.09.016. Epub Oct. 10, 2008.
Ye et al., Rational development of a combined mRNA vaccine against COVID-19 and influenza. NPJ Vaccines. Jul. 26, 2022;7(1):84. doi: 10.1038/s41541-022-00478-w.
Ying et al., Cancer therapy using a self-replicating RNA vaccine. Nat Med. Jul. 1999;5(7):823-7.
Ze et al., Identification of effective constituents of influenza vaccine by immunization with plasmid DNAs encoding viral proteins. Jpn J Infect Dis. Dec. 2000;53(6):219-28.
Zeng et al., Formulation and Delivery Technologies for mRNA Vaccines. Curr Top Microbiol Immunol. Jun. 2, 2020;10.1007/82_2020_217. doi: 10.1007/82_2020_217.
Zhang et al., Construction of eukaryotic expressing plasmids encoding HA and HA1 of influenza A virus and their transient expression in HEK293 cells. J Huazhong Univ Sci Technolog Med Sci. 2006;26(2):225-7, 230.
Zhao et al., Nanoparticle vaccines. Vaccine. Jan. 9, 2014;32(3):327-37. doi: 10.1016/j.vaccine.2013.11.069. Epub Dec. 2, 2013.
[No Author Listed], An Audience with Moncef Slaoui. Nat Rev Drug Discov Jul. 1, 2015;14:452-453. https://doi.org/10.1038/nrd4669.
[No Author Listed], Center for Drug Evaluation and Research Approval Package for New Drug Application No. 50-718/S-50 for Doxil®. Approved Dec. 28, 2015. 97 pages.
[No Author Listed], Katalin Karikó and Drew Weissman awarded Horwitz Prize for pioneering research on COVID-19 vaccines, Columbia University Irving Medical Center, Aug. 16, 2021, https://www.cuimc.columbia.edu/news/horwitz-prize-2021 (last accessed Aug. 24, 2023). 12 pages.
[No Author Listed], List of past and pending litigations. Prepared Oct. 24, 2023. 1 page.
Aartse et al., Influenza A Virus Hemagglutinin Trimer, Head and Stem Proteins Identify and Quantify Different Hemagglutinin-Specific B Cell Subsets in Humans. Vaccines (Basel). Jul. 2, 2021;9(7):717. doi: 10.3390/vaccines9070717.
Ahmad et al., New multivalent cationic lipids reveal bell curve for transfection efficiency versus membrane charge density: lipid-DNA complexes for gene delivery. J Gene Med. Jun. 2005;7(6):739-48. doi: 10.1002/jgm.717.
Ahmed et al., Biochemistry, Lipids, Statpearls Publishing (May 1, 2023) (https://www.ncbi.nlm.nih.gov/books/NBK525952/ (last accessed Aug. 24, 2023)). 5 pages.
Alberts et al., Chapters 1, 3, 5-7, 24, and 25 in Molecular Biology of the Cell, 4th Ed. (2002), 470 pages.

(56) References Cited

OTHER PUBLICATIONS

*Alnylam Pharmaceuticals, Inc. v. Moderna, Inc.* (Fed. Circ. 2023-2357) D.I. 8—Docketing Statement, Sep. 21, 2023. 2 pages.
*Alnylam Pharmaceuticals, Inc. v. Moderna, Inc. et al* (D. Del. 23-cv-580-CFC) D.I. 1—Complaint for Patent Infringement, May 26, 2023. 28 pages.
*Alnylam Pharmaceuticals, Inc. v. Moderna, Inc. et al* (D. Del. 23-cv-580-CFC) D.I. 12—Answer to the Complaint, Jul. 17, 2023. 37 pages.
*Alnylam Pharmaceuticals, Inc. v. Moderna, Inc. et al.* (D. Del. 22-cv-335-CFC) D.I. 1—Complaint for Patent Infringement, Mar. 17, 2022. 14 pages.
*Alnylam Pharmaceuticals, Inc. v. Moderna, Inc. et al.* (D. Del. 22-cv-335-CFC) D.I. 128—Final Judgement, Aug. 30, 2023. 2 pages.
*Alnylam Pharmaceuticals, Inc. v. Moderna, Inc. et al.* (D. Del. 22-cv-335-CFC) D.I. 130—Notice of Appeal to the U.S. Court of Appeals for the Federal Circuit, Aug. 31, 2023. 3 pages.
*Alnylam Pharmaceuticals, Inc. v. Moderna, Inc. et al.* (D. Del. 22-cv-335-CFC) D.I. 87—Answer to the Complaint, May 10, 2023. 44 pages.
*Arbutus BioPharma Corp et al. v. Moderna, Inc. et al.* (D. Del. 22-cv-252-MSG) D.I. 1—Complaint for Patent Infringement, Feb. 28, 2022. 51 pages.
*Arbutus BioPharma Corp et al. v. Moderna, Inc. et al.* (D. Del. 22-cv-252-MSG) D.I. 31—District Court Memorandum, Nov. 2, 2022. 16 pages.
*Arbutus BioPharma Corp et al. v. Moderna, Inc. et al.* (D. Del. 22-cv-252-MSG) D.I. 35—Answer to the Complaint, Nov. 30, 2022. 83 pages.
*Arbutus BioPharma Corp et al. v. Moderna, Inc. et al.* (D. Del. 22-cv-252-MSG) D.I. 64—District Court Memorandum, Mar. 10, 2023. 4 pages.
Atsmon et al., Safety and immunogenicity of multimeric-001—a novel universal influenza vaccine. J Clin Immunol. Jun. 2012;32(3):595-603. doi: 10.1007/s10875-011-9632-5. Epub Feb. 9, 2012.
Bangham et al., Diffusion of univalent ions across the lamellae of swollen phospholipids. J Mol Biol. Aug. 1965;13(1):238-52. doi: 10.1016/s0022-2836(65)80093-6.
Bennett et al., Cholesterol enhances cationic liposome-mediated DNA transfection of human respiratory epithelial cells. Biosci Rep. Feb. 1995;15(1):47-53. doi: 10.1007/BF01200214.
Bharali et al., Nanoparticles and cancer therapy: a concise review with emphasis on dendrimers. Int J Nanomedicine. 2009;4:1-7. Epub Apr. 1, 2009.
Clancy et al., Translation: DNA to mRNA to Protein. Nature Education 2008;1(1):101.
Cobb et al., Who discovered messenger RNA? Curr Biol. Jun. 29, 2015;25(13):R526-32. doi:10.1016/j.cub.2015.05.032.
Cooper et al., Chapters 1, 7, and 8 in The Cell: A Molecular Approach, 5th Ed. (2009), 163 pages.
Degroot et al., Part II—The Positive Sense Single Stranded RNA Viruses, Family Coronaviridae, in Virus Taxonomy: Ninth Report of the International Committee on Taxonomy of Viruses 806 (2012). 25 pages.
Del Pozo-Rodriguez et al., Lipid nanoparticles as vehicles for macromolecules: nucleic acids and peptides. Recent Pat Drug Deliv Formul. Sep. 2011;5(3):214-26. doi: 10.2174/187221111797200515.
Dimitriadis et al., Translation of rabbit globin mRNA introduced by liposomes into mouse lymphocytes. Nature. Aug. 3, 19781;274(5674):923-4. doi: 10.1038/274923a0.
Dormitzer, Synthetic Vaccinology at Novartis, Presentation at The National Academy of Sciences Forum on Synthetic Biology. Oct. 21, 2013, The Keck Center, Washington, DC. 12 pages.
Dufourc, Sterols and membrane dynamics. J Chem Biol. Nov. 2008; 1(1-4):63-77. doi: 10.1007/s12154-008-0010-6. Epub Sep. 23, 2008.
Engler et al., Half- vs full-dose trivalent inactivated influenza vaccine (2004-2005): age, dose, and sex effects on immune responses. Arch Intern Med. Dec. 8, 2008;168(22):2405-14. doi: 10.1001/archinternmed.2008.513.

Geall et al., Using self-amplifying mRNA vaccines to facilitate a rapid response to pandemic influenza. Eur Pharm Rev. Jul. 3, 2014; 3. 8 pages.
Guo et al., Nanoparticles escaping RES and endosome: Challenges for siRNA delivery for cancer therapy. J Nanomat. Jan. 2011;742895:1-12.
Hanson et al., Identification of Stabilizing Mutations in an H5 Hemagglutinin Influenza Virus Protein. J Virol. Dec. 30, 2015;90(6):2981-92. doi: 10.1128/JVI.02790-15.
He et al., Low molecular weight protamine (LMWP): a nontoxic protamine substitute and an effective cell-penetrating peptide. J Control Release. Nov. 10, 2014;193:63-73. doi: 10.1016/j.jconrel.2014.05.056. Epub Jun. 3, 2014.
Hemmer et al., Minimal peptide length requirements for CD4(+) T cell clones—implications for molecular mimicry and T cell survival. Int Immunol. Mar. 2000;12(3):375-83. doi: 10.1093/intimm/12.3.375.
Huang et al., Asymmetric 1-alkyl-2-acyl phosphatidylcholine: a helper lipid for enhanced non-viral gene delivery. Int J Pharm. May 1, 2012;427(1):64-70. doi: 10.1016/j.ijpharm.2011.06.022. Epub Jun. 21, 2011.
Huang et al., Construction and biological characterisation of recombinant porcine circovirus type 2 expressing the V5 epitope tag. Virus Res. Nov. 2011;161(2):115-23. doi: 10.1016/j.virusres.2011.05.015. Epub May 27, 2011.
Impagliazzo et al., A stable trimeric influenza hemagglutinin stem as a broadly protective immunogen. Science. Sep. 18, 2015;349(6254):1301-6. doi: 10.1126/science.aac7263. Epub Aug. 24, 2015.
Johanning et al., A Sindbis virus mRNA polynucleotide vector achieves prolonged and high level heterologous gene expression in vivo. Nucleic Acids Res. May 11, 1995; 23(9): 1495-1501.
Kanasty et al., Delivery materials for siRNA therapeutics. Nat Mater. Nov. 2013;12(11):967-77. doi: 10.1038/nmat3765.
Kresge, The messenger RNA pioneers everyone ignored. Bloomberg, Nov. 23, 2021, https://www.bloomberg.com/news/newsletters/2021-11-23/themessenger-rna-pioneers-everyone-ignored (last accessed Aug. 24, 2023). 8 pages.
Lee et al., Design and Structure of an Engineered Disulfide-Stabilized Influenza Virus Hemagglutinin Trimer. J Virol. Jul. 2015;89(14):7417-20. doi: 10.1128/JVI.00808-15. Epub Apr. 29, 2015.
Leuschner et al., Therapeutic siRNA silencing in inflammatory monocytes in mice. Nat Biotechnol. Oct. 9, 2011;29(11):1005-10. doi: 10.1038/nbt.1989.
Li et al., Application of ultra-high performace liquid chromatography for chemical characterization of liposome-based therapeutic small-interfering RNA, 13 American Pharmaceutical Review 102 (2010). 13 pages.
Li et al., Cell Attachment Domains of the Porcine Epidemic Diarrhea Virus Spike Protein Are Key Targets of Neutralizing Antibodies. J Virol. May 26, 2017;91(12):e00273-17. doi: 10.1128/JVI.00273-17. Print Jun. 15, 2017.
Li, Receptor recognition mechanisms of coronaviruses: a decade of structural studies. J Virol. Feb. 2015;89(4):1954-64. doi: 10.1128/JVI.02615-14. Epub Nov. 26, 2014.
Lin et al., Three-dimensional imaging of lipid gene-carriers: membrane charge density controls universal transfection behavior in lamellar cationic liposome-DNA complexes. Biophys J. May 2003;84(5):3307-16. doi: 10.1016/S0006-3495(03)70055-1.
Liu et al., Influence of polyethylene glycol density and surface lipid on pharmacokinetics and biodistribution of lipid-calcium-phosphate nanoparticles. Biomaterials. Mar. 2014;35(9):3027-34. doi: 10.1016/j.biomaterials.2013.12.022. Epub Jan. 2, 2014.
Lu et al., Production and stabilization of the trimeric influenza hemagglutinin stem domain for potentially broadly protective influenza vaccines. Proc Natl Acad Sci U S A. Jan. 7, 2014;111(1):125-30. doi: 10.1073/pnas.1308701110. Epub Dec. 1, 2013.
Lugovtsev et al., Generation of the influenza B viruses with improved growth phenotype by substitution of specific amino acids of hemagglutinin. Virology. Sep. 1, 2007;365(2):315-23. doi: 10.1016/j.virol.2007.04.006. Epub May 8, 2007.

(56) References Cited

OTHER PUBLICATIONS

McDonnell et al. DNA vaccines. N Engl J Med. Jan. 4, 1996;334(1):42-5. doi: 10.1056/NEJM199601043340110.

McLellan et al., Structure and function of respiratory syncytial virus surface glycoproteins. Curr Top Microbiol Immunol. 2013;372:83-104. doi: 10.1007/978-3-642-38919-1_4.

Mendonca et al., Design of lipid-based nanoparticles for delivery of therapeutic nucleic acids. Drug Discov Today. Mar. 2023;28(3):103505. doi: 10.1016/j.drudis.2023.103505. Epub Jan. 25, 2023.

Milder et al., Universal stabilization of the influenza hemagglutinin by structure-based redesign of the pH switch regions. Proc Natl Acad Sci U S A. Feb. 8, 2022;119(6):e2115379119. doi: 10.1073/pnas.2115379119.

*ModernaTX, Inc. et al v. Pfizer Inc.et al*. (D. Mass. 22-11378-RGS) D.I. 105—District Court Memorandum and Order on Claim Construction, Aug. 1, 2023. 15 pages.

*ModernaTX, Inc. et al.v. Pfizer Inc.et al*. (D. Mass. 22-11378-RGS) D.I. 1—Complaint for Patent Infringement, Aug. 26, 2022. 39 pages.

*ModernaTX, Inc. et al.v. Pfizer Inc.et al*. (D. Mass. 22-11378-RGS) D.I. 45—Answer to the Complaint, Dec. 5, 2022. 81 pages.

Murphy, Excerpts from Janeway's Immunobiology, 8th Ed. (2012). 250 pages.

Opposition against European Patent No. 3324979 B1, filed by BioNTech SE (Opponent) against ModernaTX, Inc. (Patentee) on Jul. 10, 2023. 83 pages.

Ostro et al., Evidence for translation of rabbit globin mRNA after liposome-mediated insertion into a human cell line. Nature. Aug. 31, 1978;274(5674):921-3. doi: 10.1038/274921a0.

Pascolo., Messenger RNA-based vaccines. Expert Opin Biol Ther. Aug. 2004;4(8):1285-94. doi: 10.1517/14712598.4.8.1285.

Peabody et al., Termination-reinitiation occurs in the translation of mammalian cell mRNAs. Mol Cell Biol. Jul. 1986;6(7):2695-703. doi: 10.1128/mcb.6.7.2695-2703.1986.

Peek et al., Nanotechnology in vaccine delivery. Adv Drug Deliv Rev. May 22, 2008;60(8):915-28. doi: 10.1016/j.addr.2007.05.017. Epub Feb. 7, 2008.

Petition for Inter Partes Review of U.S. Pat. No. 10,702,600. *BioNTech SE and Pfizer Inc*. (Petitioners) v. *ModernaTX, Inc*. (Patent Owner). Filed Aug. 28, 2023. 87 pages.

Petition for Inter Partes Review of U.S. Pat. No. 10,933,127. *BioNTech SE and Pfizer Inc*. (Petitioners) v. *ModernaTX, Inc*. (Patent Owner). Filed Aug. 28, 2023. 89 pages.

Petition for Inter Partes Review of U.S. Pat. No. 8,058,069 (IPR2019-00554). *Moderna Therapeutics, Inc*. (Petitioner) v. *Arbutus Biopharma Corporation* (Patent Owner). Filed Nov. 15, 2011. 81 pages.

Probst et al., Characterization of the ribonuclease activity on the skin surface. Genet Vaccines Ther. May 29, 2006;4:4. doi: 10.1186/1479-0556-4-4.

*Promosome, LLC v. Moderna, Inc*. (S.D. Cal. 23-cv-1047-JES-DDL) D.I. 1—Complaint for Patent Infringement, Jun. 6, 2023. 51 pages.

*Promosome, LLC v. Moderna, Inc*. (S.D. Cal. 23-cv-1047-JES-DDL) D.I. 30—Notice of Dismissal, Sep. 19, 2023. 4 pages.

Rossi et al., IRES-based Venezuelan equine encephalitis vaccine candidate elicits protective immunity in mice. Virology. Mar. 15, 2013;437(2):81-8. doi: 10.1016/j.virol.2012.11.013. Epub Jan. 22, 2013.

Schuurhuis et al., Ins and outs of dendritic cells. Int Arch Allergy Immunol. 2006;140(1):53-72. doi: 10.1159/000092002. Epub Mar. 13, 2006.

Shidhadye et al., Solid lipid nanoparticles and nanostructured lipid carriers—innovative generations of solid lipid carriers. Curr Drug Deliv. Oct. 2008;5(4):324-31. doi: 10.2174/156720108785915087.

Staneková et al., Conserved epitopes of influenza A virus inducing protective immunity and their prospects for universal vaccine development. Virol J. Nov. 30, 2010;7:351. doi: 10.1186/1743-422X-7-351.

Tenchov et al., Lipid Nanoparticles—From Liposomes to mRNA Vaccine Delivery, a Landscape of Research Diversity and Advancement. ACS Nano. Nov. 23, 2021;15(11):16982-17015. doi: 10.1021/acsnano.1c04996. Epub Jun. 28, 2021.

Tews et al., Chapter 2: Self-Replicating RNA. RNA Vaccines. 2017; 1499: 15-35. Published online Jun. 11, 2016. doi: 10.1007/978-1-4939-6481-9_2.

Thery et al., The cell biology of antigen presentation in dendritic cells. Curr Opin Immunol. Feb. 2001;13(1):45-51. doi: 10.1016/s0952-7915(00)00180-1.

Van Boheemen et al., Genomic characterization of a newly discovered coronavirus associated with acute respiratory distress syndrome in humans. mBio. Nov. 20, 2012;3(6):e00473-12. doi: 10.1128/mBio.00473-12.

Verma et al., Double-headed nucleosides: Synthesis and applications. Beilstein J Org Chem. Jun. 8, 2021;17:1392-1439. doi: 10.3762/bjoc.17.98. eCollection 2021.

Walls et al., Crucial steps in the structure determination of a coronavirus spike glycoprotein using cryo-electron microscopy. Protein Sci. Jan. 2017;26(1):113-121. doi: 10.1002/pro.3048. Epub Oct. 18, 2016.

Walls et al., Tectonic conformational changes of a coronavirus spike glycoprotein promote membrane fusion. Proc Natl Acad Sci U S A. Oct. 17, 2017;114(42):11157-11162. doi: 10.1073/pnas.1708727114. Epub Oct. 3, 2017.

Whitehead et al., Knocking down barriers: advances in siRNA delivery. Nat Rev Drug Discov. Feb. 2009;8(2):129-38. doi: 10.1038/nrd2742.

Yildiz et al., Trans-Amplifying RNA: A Journey from Alphavirus Research to Future Vaccines. Viruses. Mar. 25, 2024;16(4):503. doi: 10.3390/v16040503.

Zhao et al., Key Aspects of Coronavirus Avian Infectious Bronchitis Virus. Pathogens. May 11, 2023;12(5):698. doi: 10.3390/pathogens12050698.

Zhukovsky et al., Heterogeneity of early intermediates in cell-liposome fusion mediated by influenza hemagglutinin. Biophys J. Nov. 1, 2006;91(9):3349-58. doi: 10.1529/biophysj.106.088005. Epub Aug. 11, 2006.

Ziganshina et al., Antibody-Dependent Enhancement with a Focus on SARS-CoV-2 and Anti-Glycan Antibodies. Viruses. Jul. 20, 2023;15(7):1584. doi: 10.3390/v15071584.

Zumla et al., Middle East respiratory syndrome. Lancet. Sep. 5, 2015;386(9997):995-1007. doi: 10.1016/S0140-6736(15)60454-8. Epub Jun. 3, 2015.

[No. Author Listed], Moderna Announces Positive Interim Phase 1 Data for mRNA Flu Vaccine and Provides Program Update. Press Release. Dec. 10, 2021. 5 pages.

[No. Author Listed], "Measles morbillivirus" Wikipedia. 6 pages.

[No Author Listed], Influenza A virus A/Jiangxi/IPB13/2013(H10N8) segment 4 hemagglutinin (HA) gene, complete CDS. Genbank Accession No. KJ406543.1. Jun. 12, 2014. 2 pages.

[No. Author Listed], Peptide search in human proteome. Moderna. Presentation. 2023. 3 pages.

[No. Author Listed], Pfizer Second Quarter 2022 Earnings Teleconference. Jul. 28, 2022. Powerpoint. 50 pages.

Altieri et al., The influence of 4-thiouridine labeling on pre-mRNA splicing outcomes. PLoS One. Dec. 13, 2021;16(12):e0257503. doi: 10.1371/journal.pone.0257503.eCollection 2021.

Anderson, B.R., et al., Incorporation of pseudouridine into mRNA enhances translation by diminishing PKR activation. Nucleic Acids Res. Sep. 2010;38(17):5884-92. doi: 10.1093/nar/gkq347. Epub May 10, 2010.

Anderson, B.R., et al., Nucleoside modifications in RNA limit activation of 2'-5'—oligoadenylate synthetase and increase resistance to cleavage by Rnase L. Nucleic Acids Res. Nov. 2011;39(21):9329-38. doi: 10.1093/nar/gkr586. Epub Aug. 3, 2011.

Berg et al., Chapter 4: DNA, RNA, and the flow of genetic information. In: Biochemistry. 6th ed. New York: W.H. Freeman; 2007. p. 107, 119, 126.

Cheng et al., Selective organ targeting (SORT) nanoparticles for tissue-specific mRNA delivery and CRISPR-Cas gene editing. Nat Nanotechnol. Apr. 2020; 15(4):313-320. doi: 10.1038/s41565-020-0669-6. Epub Apr. 6, 2020.

(56) References Cited

OTHER PUBLICATIONS

Choi et al., 2'-O-methylation in mRNA disrupts tRNA decoding during translation elongation. Nat Struct Mol Biol. Mar. 2018;25(3):208-216. doi: 10.1038/s41594-018-0030-z. Epub Feb. 19, 2018.
Communication from Examining Division for European Application No. EP15783606.5, dated Sep. 27, 2019. 3 pages.
Cross, Without these lipid shells, there would be No. mRNA vaccines for COVID-19. C&EN. Mar. 6, 2021;99(8):1-8.
Declaration of Andrew S. Janoff, Ph.D., in support of petition for Inter Partes Review of U.S. Pat. No. 9,364,435. 69 pages.
Excerpt of sequence listing of WO2013/151664A1: Seq Id Nos. 9536 and 11305. 1 page.
Excerpt of sequence listing of WO2013/151665A2: Seq Id Nos. 36664, 9113, 45126, 46239, 48832, 56491, 57415, 61169, 63754, 63756, and 69168. 4 pages.
Excerpt of sequence listing of WO2013/151667A1: Seq Id Nos. 158 and 160. 2 pages.
Excerpt of sequence listing of WO2013/151672A2: Seq Id No. 5787. 1 page.
Excerpt of sequence listing of WO 2013/ 151663 A1: Seq Id Nos. 12907, 13731, 13903, 14383, 14485, and 15605.
Guevara et al., Advances in Lipid Nanoparticles for mRNA-Based Cancer Immunotherapy. Front Chem. 2020; 8: 589959.
Hashiba et al., The use of design of experiments with multiple responses to determine optimal formulations for in vivo hepatic mRNA delivery. J Control Release. Nov. 10, 2020;327:467-476. doi: 10.1016/j.jconrel.2020.08.031. Epub Aug. 25, 2020.
Hess et al., Vaccination with mRNAs encoding tumor-associated antigens and granulocyte-macrophage colony-stimulating factor efficiently primes CTL responses, but is insufficient to overcome tolerance to a model tumor/self antigen. Cancer Immunol Immunother. Jun. 2006;55(6):672-83. Epub Aug. 20, 2005.
Hoernes et al., Nucleotide modifications within bacterial messenger RNAs regulate their translation and are able to rewire the genetic code. Nucleic Acids Res. Jan. 29, 2016; 44(2): 852-862.
Jayaraman et al., Maximizing the potency of siRNA lipid nanoparticles for hepatic gene silencing in vivo. Angew Chem Int Ed Engl. Aug. 20, 2012;51(34):8529-33. doi: 10.1002/anie.201203263.
Kallen et al., A novel, disruptive vaccination technology: self-adjuvanted RNActive(®) vaccines. Hum Vaccin Immunother. Oct. 2013;9(10):2263-76. doi: 10.4161/hv.25181. Epub Jun. 4, 2013. Review.
Karikó et al. Naturally occurring nucleoside modifications suppress the immunostimulatory activity of RNA: Implication for therapeutic RNA development. Current Opinion in Drug Discovery & Development 2007 10(5) 523-532; The Thomson Corporation ISSN 1367-6733.
Karikó et al., Generating the optimal mRNA for therapy: HPLC purification eliminates immune activation and improves translation of nucleoside-modified, protein-encoding mRNA, Nucleic Acids Research, Oxford University Press, GB, vol. 39, No. 21, Sep. 2, 2011 (Sep, 2, 2011), e142. doi: 10.1093/nar/gkr695. Epub Sep. 2, 2011.
Karikó et al., Incorporation of pseudouridine into mRNA yields superior nonimmunogenic vector with increased translational capacity and biological stability. Mol Ther. Nov. 2008; 16(11):1833-40. Epub Sep. 16, 2008.
Karikó et al., Increased erythropoiesis in mice injected with submicrogram quantities of pseudouridine-containing mRNA encoding erythropoietin. Mol Ther. May 2012; 20(5): 948-953.
Karikó et al., Suppression of RNA recognition by Toll-like receptors: the impact of nucleoside modification and the evolutionary origin of RNA. Immunity. Aug. 2005;23(2):165-75.
Karikó, Modified uridines are the key to a successful message. Nat Rev Immunol. Oct. 2021;21(10):619. doi: 10.1038/s41577-021-00608-w.
Kauffman et al., Optimization of Lipid Nanoparticle Formulations for mRNA Delivery in Vivo with Fractional Factorial and Definitive Screening Designs. Nano Lett. Nov. 11, 2015;15(11):7300-6. doi: 10.1021/acs.nanolett.5b02497. Epub Oct. 20, 2015.
Kormann, M. et al. Expression of therapeutic proteins after delivery of chemically modified mRNA in mice. Nat Biotechnol. Feb. 2011;29(2):154-7.
Li et al., Peptide Vaccine: Progress and Challenges. Vaccines (Basel). Jul. 2, 2014;2(3):515-36. doi: 10.3390/vaccines2030515.
Miao et al., Delivery of mRNA vaccines with heterocyclic lipids increases anti-tumor efficacy by STING-mediated immune cell activation. Nat Biotechnol 37, 1174-1185 (2019). https://doi.org/10.1038/s41587-019-0247-3.
Pardi et al., Nucleoside-modified mRNA immunization elicits influenza virus hemagglutinin stalk-specific antibodies. Nat Commun. Aug. 22, 2018;9(1):3361. doi: 10.1038/s41467-018-05482-0.
Proprietor's Response for European Application No. EP15783606.5, dated Feb. 7, 2020. 7 pages.
Proprietor's Response for European Application No. EP15783606.5, dated Apr. 8, 2021. 4 pages.
Sahin et al., mRNA-based therapeutics—developing a new class of drugs. Nat Rev Drug Discov. Oct. 2014; 13(10):759-80. doi: 10.1038/nrd4278. Epub Sep. 19, 2014.
Schumann et al., Multiple links between 5-methylcytosine content of mRNA and translation. BMC Biol. Apr. 15, 2020;18(1):40. doi: 10.1186/s12915-020-00769-5.
Semple, S.C., et al., Rational design of cationic lipids for siRNA delivery. Nat Biotechnol. Feb. 2010; 28(2): 172-176.
Stephenson et al., Cross-reactivity to highly pathogenic avian influenza H5N1 viruses after vaccination with nonadjuvanted and MF59-adjuvanted influenza A/Duck/Singapore/97 (H5N3) vaccine: a potential priming strategy. J Infect Dis. Apr. 15, 2005;191(8):1210-5. doi: 10.1086/428948. Epub Mar. 14, 2005.
Summons to Attend Oral Proceedings for European Application No. EP15783606.5, dated Oct. 14, 2020. 10 pages.
Wong et al., Traditional and new influenza vaccines. Clin Microbiol Rev. Jul. 2013;26(3):476-92. doi: 10.1128/CMR.00097-12.
Yin et al., Non-viral vectors for gene-based therapy. Nat Rev Genet. Aug. 2014;15(8):541-55. doi: 10.1038/nrg3763. Epub Jul. 15, 2014.

INFLUENZA VACCINE

RELATED APPLICATIONS

This application is a continuation of U.S. application Ser. No. 17/127,949, filed Dec. 18, 2020, which is a division of U.S. application Ser. No. 16/348,943, filed May 10, 2019, which is a national stage filing under 35 U.S.C. § 371 of International Application No. PCT/US2017/061182, filed Nov. 10, 2017, which was published under PCT Article 21(2) in English, and claims the benefit under 35 U.S.C. 119(e) of the filing date of U.S. Provisional Application Serial Number No. 62/421,160, filed Nov. 11, 2016, each of which is incorporated herein by reference in its entirety.

REFERENCE TO AN ELECTRONIC SEQUENCE LISTING

The contents of the electronic sequence listing (M137870059US03-SEQ-HCL.xml; Size: 42,582 bytes; and Date of Creation: May 22, 2023) is herein incorporated by reference in its entirety.

BACKGROUND

Influenza A virus subtype H7N9 is a form of influenza with a high potential to become pandemic. Over 600 cases of H7N9 influenza have been documented in China to date, with a mortality rate of approximately 1 in 3 people. This may have resulted from sporadic, non-sustained human-to-human transmission. Although several vaccines are in development, immunogenicity has been reportedly low without the addition of adjuvants.

Influenza A virus subtype H10N8 has also shown a potential to become pandemic, but is at lower risk than influenza A virus subtype H7N9. In 2013, only 3 cases of H10N8 influenza infection were reported in China, resulting in 2 deaths. To date, no vaccine is available.

SUMMARY

RNA Influenza vaccines and methods of vaccinating a subject against influenza are provided according to the invention. In some aspects the invention is a method of inducing an antigen specific immune response in a human subject, comprising administering a dose of 10-100 ug of a nucleic acid vaccine comprising an RNA polynucleotide having an open reading frame encoding a hemagglutinin antigen formulated within a cationic lipid nanoparticle to the human subject, wherein a protective HA antigen specific immune response is induced.

A method of inducing an antigen specific immune response in a human subject, comprising administering a dose of 10-100 ug of a nucleic acid vaccine comprising an RNA polynucleotide having an open reading frame encoding an HA7 hemagglutinin antigen formulated within a cationic lipid nanoparticle to the human subject, wherein a protective HA7 antigen specific immune response is induced is provided in some aspects of the invention.

In some embodiments the protective HA7 antigen specific immune response is determined by production of a neutralizing antibody titer of at least 2, 3, 4, or 5 times greater than baseline in the human subject. In some embodiments the protective HA7 antigen specific immune response is determined by production of a neutralizing antibody titer of 2-10 times greater than baseline in the human subject. In other embodiments the protective HA7 antigen specific immune response is determined by production of a microneutralization value of greater than 1:20 in the human subject. In some embodiments the protective HA7 antigen specific immune response is determined by production of an HAI titer of at least 1:40, at least 1:60, at least 1:80 or at least 1:90 in the human subject. In some embodiments the protective HA7 antigen specific immune response is determined by production of an HAI titer of 1:40-1:200 in the human subject. In other embodiments the protective HA7 antigen specific immune response is determined by production of an increase in HAI level of at least 4 times, at least 5 times or at least 6 times relative to a baseline HAI level in the human subject.

In some embodiments the HA7 hemagglutinin antigen is an H7N9 antigen. In other embodiments the RNA polynucleotide comprises a polynucleotide encoding an amino acid sequence having at least 80% sequence identity to SEQ ID NO 1. In other embodiments the RNA polynucleotide comprises a polynucleotide encoding the amino acid sequence of SEQ ID NO 1. In other embodiments the RNA polynucleotide has at least 80% sequence identity to SEQ ID NO 5, 6, 7, or 9.

In other aspects the invention is a method of inducing an antigen specific immune response in a human subject, comprising administering a dose of 10-100 ug of a nucleic acid vaccine comprising an RNA polynucleotide having an open reading frame encoding an HA10 hemagglutinin antigen formulated within a cationic lipid nanoparticle to the human subject, wherein a protective HA10 antigen specific immune response is induced.

In some embodiments the protective HA10 antigen specific immune response is determined by production of a neutralizing antibody titer of at least 2, 3, 4, or 5 times greater than baseline in the human subject. In some embodiments the protective HA10 antigen specific immune response is determined by production of a neutralizing antibody titer of 2-10 times greater than baseline in the human subject. In other embodiments the protective HA10 antigen specific immune response is determined by production of a microneutralization value of greater than 1:20 in the human subject. In some embodiments the protective HA10 antigen specific immune response is determined by production of an HAI titer of at least 1:40, at least 1:60, at least 1:80 or at least 1:90 in the human subject. In some embodiments the protective HA10 antigen specific immune response is determined by production of an HAI titer of 1:40-1:200 in the human subject. In other embodiments the protective HA10 antigen specific immune response is determined by production of an increase in HAI level of at least 4 times, at least 5 times or at least 6 times relative to a baseline HAI level in the human subject.

In some embodiments the HA10 hemagglutinin antigen is an H10N8 antigen. In some embodiment the RNA polynucleotide comprises a polynucleotide encoding an amino acid sequence having at least 80% sequence identity to SEQ ID NO 4. In some embodiments the RNA polynucleotide comprises a polynucleotide encoding the amino acid sequence of SEQ ID NO 4. In other embodiments the RNA polynucleotide has at least 80% sequence identity to SEQ ID NO 2, 3, or 8.

The method of producing an antigen specific immune response in some embodiments involves a single administration of the vaccine, and wherein the protective immune response is produced with the single administration. In other embodiments a booster dose of the vaccine is administered, and wherein the protective immune response is produced with the booster administration.

In some aspects the invention is a method of inducing an antigen specific immune response in a subject, comprising administering a nucleic acid vaccine comprising an RNA polynucleotide having an open reading frame encoding an influenza virus antigen formulated within a cationic lipid nanoparticle to the subject, wherein a protective influenza virus antigen specific immune response is maintained in the subject for more than 2 years. In some embodiments the protective influenza virus antigen specific immune response is maintained in the subject for more than 4 years. In other embodiments the protective influenza virus antigen specific immune response is maintained in the subject for more than 8 years. In yet other embodiments the protective influenza virus antigen specific immune response is maintained in the subject for more than 10 years.

In other aspects the invention is a vaccine comprising an mRNA encoding an influenza virus antigen formulated in a lipid nanoparticle comprising compounds of Formula (I):

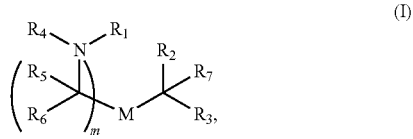
(I)

or a salt or isomer thereof, wherein:

$R_1$ is selected from the group consisting of $C_{5-30}$ alkyl, $C_{5-20}$ alkenyl, —R*YR″, —YR″, and —R″M′R′;

$R_2$ and $R_3$ are independently selected from the group consisting of H, $C_{1-14}$ alkyl, $C_{2-14}$ alkenyl, —R*YR″, —YR″, and —R*OR″, or $R_2$ and $R_3$, together with the atom to which they are attached, form a heterocycle or carbocycle;

$R_4$ is selected from the group consisting of a $C_{3-6}$ carbocycle, —(CH$_2$)$_n$Q, —(CH$_2$)$_n$CHQR, —CHQR, —CQ(R)$_2$, and unsubstituted $C_{1-6}$ alkyl, where Q is selected from a carbocycle, heterocycle, —OR, —O(CH$_2$)$_n$N(R)$_2$, —C(O)OR, —OC(O)R, —CX$_3$, —CX$_2$H, —CXH$_2$, —CN, —N(R)$_2$, —C(O)N(R)$_2$, —N(R)C(O)R, —N(R)S(O)$_2$R, —N(R)C(O)N(R)$_2$, —N(R)C(S)N(R)$_2$, —N(R)R$_8$, —O(CH$_2$)$_n$OR, —N(R)C(=NR$_9$)N(R)$_2$, —N(R)C(=CHR$_9$)N(R)$_2$, —OC(O)N(R)$_2$, —N(R)C(O)OR, —N(OR)C(O)R, —N(OR)S(O)$_2$R, —N(OR)C(O)OR, —N(OR)C(O)N(R)$_2$, —N(OR)C(S)N(R)$_2$, —N(OR)C(=NR$_9$)N(R)$_2$, —N(OR)C(=CHR$_9$)N(R)$_2$, —C(=NR$_9$)N(R)$_2$, —C(=NR$_9$)R, —C(O)N(R)OR, and —C(R)N(R)$_2$C(O)OR, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M′ are independently selected from —C(O)O—, —OC(O)—, —C(O)N(R′)—, —N(R′)C(O)—, —C(O)—, —C(S)—, —C(S)S—, —SC(S)—, —CH(OH)—, —P(O)(OR′)O—, —S(O)$_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, NO$_2$, $C_{1-6}$ alkyl, —OR, —S(O)$_2$R, —S(O)$_2$N(R)$_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R′ is independently selected from the group consisting of $C_{1-18}$ alkyl, $C_{2-18}$ alkenyl, —R*YR″, —YR″, and H;

each R″ is independently selected from the group consisting of $C_{3-14}$ alkyl and $C_{3-14}$ alkenyl;

each R* is independently selected from the group consisting of $C_1$-12 alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13.

In some embodiments a subset of compounds of Formula (I) includes those in which when $R_4$ is —(CH$_2$)$_n$Q, —(CH$_2$)$_n$CHQR, —CHQR, or —CQ(R)$_2$, then (i) Q is not —N(R)$_2$ when n is 1, 2, 3, 4 or 5, or (ii) Q is not 5, 6, or 7-membered heterocycloalkyl when n is 1 or 2.

In some embodiments a subset of compounds of Formula (I) includes those in which $R_1$ is selected from the group consisting of $C_{5-30}$ alkyl, $C_{5-20}$ alkenyl, —R*YR″, —YR″, and —R″M′R′;

$R_2$ and $R_3$ are independently selected from the group consisting of H, $C_{1-14}$ alkyl, $C_{2-14}$ alkenyl, —R*YR″, —YR″, and —R*OR″, or $R_2$ and $R_3$, together with the atom to which they are attached, form a heterocycle or carbocycle;

$R_4$ is selected from the group consisting of a $C_{3-6}$ carbocycle, —(CH$_2$)$_n$Q, —(CH$_2$)$_n$CHQR, —CHQR, —CQ(R)$_2$, and unsubstituted $C_{1-6}$ alkyl, where Q is selected from a $C_{3-6}$ carbocycle, a 5- to 14-membered heteroaryl having one or more heteroatoms selected from N, O, and S, —OR, —O(CH$_2$)$_n$N(R)$_2$, —C(O)OR, —OC(O)R, —CX$_3$, —CX$_2$H, —CXH$_2$, —CN, —C(O)N(R)$_2$, —N(R)C(O)R, —N(R)S(O)$_2$R, —N(R)C(O)N(R)$_2$, —N(R)C(S)N(R)$_2$, —CRN(R)$_2$C(O)OR, —N(R)R$_8$, —O(CH$_2$)$_n$OR, —N(R)C(=NR$_9$)N(R)$_2$, —N(R)C(=CHR$_9$)N(R)$_2$, —OC(O)N(R)$_2$, —N(R)C(O)OR, —N(OR)C(O)R, —N(OR)S(O)$_2$R, —N(OR)C(O)OR, —N(OR)C(O)N(R)$_2$, —N(OR)C(S)N(R)$_2$, —N(OR)C(=NR$_9$)N(R)$_2$, —N(OR)C(=CHR$_9$)N(R)$_2$, —C(=NR$_9$)N(R)$_2$, —C(=NR$_9$)R, —C(O)N(R)OR, and a 5- to 14-membered heterocycloalkyl having one or more heteroatoms selected from N, O, and S which is substituted with one or more substituents selected from oxo (=O), OH, amino, mono- or di-alkylamino, and $C_{1-3}$ alkyl, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M′ are independently selected from —C(O)O—, —OC(O)—, —C(O)N(R′)—, —N(R′)C(O)—, —C(O)—, —C(S)—, —C(S)S—, —SC(S)—, —CH(OH)—, —P(O)(OR′)O—, —S(O)$_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, NO$_2$, $C_{1-6}$ alkyl, —OR, —S(O)$_2$R, —S(O)$_2$N(R)$_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments a subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —$(CH_2)_nQ$, —$(CH_2)_n$CHQR, —CHQR, —CQ$(R)_2$, and unsubstituted $C_{1-6}$ alkyl, where Q is selected from a $C_{3-6}$ carbocycle, a 5- to 14-membered heterocycle having one or more heteroatoms selected from N, O, and S, —OR, —O$(CH_2)_nN(R)_2$, —C(O)OR, —OC(O)R, —$CX_3$, —$CX_2H$, —$CXH_2$, —CN, —C(O)N$(R)_2$, —N(R)C(O)R, —N(R)S(O)$_2$R, —N(R)C(O)N$(R)_2$, —N(R)C(S)N$(R)_2$, —CRN$(R)_2$C(O)OR, —N(R)$R_8$, —O$(CH_2)_n$OR, —N(R)C(=$NR_9$)N$(R)_2$, —N(R)C(=$CHR_9$)N$(R)_2$, —OC(O)N$(R)_2$, —N(R)C(O)OR, —N(OR)C(O)R, —N(OR)S(O)$_2$R, —N(OR)C(O)OR, —N(OR)C(O)N$(R)_2$, —N(OR)C(S)N$(R)_2$, —N(OR)C(=$NR_9$)N$(R)_2$, —N(OR)C(=$CHR_9$)N$(R)_2$, —C(=$NR_9$)R, —C(O)N(R)OR, and —C(=$NR_9$)N$(R)_2$, and each n is independently selected from 1, 2, 3, 4, and 5; and when Q is a 5- to 14-membered heterocycle and (i) $R_4$ is —$(CH_2)_nQ$ in which n is 1 or 2, or (ii) $R_4$ is —$(CH_2)_n$CHQR in which n is 1, or (iii) $R_4$ is —CHQR, and —CQ$(R)_2$, then Q is either a 5- to 14-membered heteroaryl or 8- to 14-membered heterocycloalkyl;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, $NO_2$, $C_{1-6}$ alkyl, —OR, —S(O)$_2$R, —S(O)$_2$N$(R)_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments a subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —$(CH_2)_nQ$, —$(CH_2)_n$CHQR, —CHQR, —CQ$(R)_2$, and unsubstituted $C_{1-6}$ alkyl, where Q is selected from a $C_{3-6}$ carbocycle, a 5- to 14-membered heteroaryl having one or more heteroatoms selected from N, O, and S, —OR, —O$(CH_2)_nN(R)_2$, —C(O)OR, —OC(O)R, —$CX_3$, —$CX_2H$, —$CXH_2$, —CN, —C(O)N$(R)_2$, —N(R)C(O)R, —N(R)S(O)$_2$R, —N(R)C(O)N$(R)_2$, —N(R)C(S)N$(R)_2$, —CRN$(R)_2$C(O)OR, —N(R)$R_8$, —O$(CH_2)_n$OR, —N(R)C(=$NR_9$)N$(R)_2$, —N(R)C(=$CHR_9$)N$(R)_2$, —OC(O)N$(R)_2$, —N(R)C(O)OR, —N(OR)C(O)R, —N(OR)S(O)$_2$R, —N(OR)C(O)OR, —N(OR)C(O)N$(R)_2$, —N(OR)C(S)N$(R)_2$, —N(OR)C(=$NR_9$)N$(R)_2$, —N(OR)C(=$CHR_9$)N$(R)_2$, —C(=$NR_9$)R, —C(O)N(R)OR, and —C(=$NR_9$)N$(R)_2$, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, $NO_2$, $C_{1-6}$ alkyl, —OR, —S(O)$_2$R, —S(O)$_2$N$(R)_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments subset of compounds of Formula (I) includes those in which $R_1$ is selected from the group consisting of $C_{5-30}$ alkyl, $C_{5-20}$ alkenyl, —R*YR", —YR", and —R"M'R';

R$_2$ and R$_3$ are independently selected from the group consisting of H, C$_{2-14}$ alkyl, C$_{2-14}$ alkenyl, —R*YR", —YR", and —R*OR", or R$_2$ and R$_3$, together with the atom to which they are attached, form a heterocycle or carbocycle;

R$_4$ is —(CH$_2$)$_n$Q or —(CH$_2$)$_n$CHQR, where Q is —N(R)$_2$, and n is selected from 3, 4, and 5;

each R$_5$ is independently selected from the group consisting of C$_{1-3}$ alkyl, C$_{2-3}$ alkenyl, and H;

each R$_6$ is independently selected from the group consisting of C$_{1-3}$ alkyl, C$_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group;

R$_7$ is selected from the group consisting of C$_{1-3}$ alkyl, C$_{2-3}$ alkenyl, and H;

each R is independently selected from the group consisting of C$_{1-3}$ alkyl, C$_{2-3}$ alkenyl, and H;

each R' is independently selected from the group consisting of C$_{1-18}$ alkyl, C$_{2-18}$ alkenyl, —R*YR", —YR", and H;

each R" is independently selected from the group consisting of C$_{3-14}$ alkyl and C$_{3-14}$ alkenyl;

each R* is independently selected from the group consisting of C$_{1-12}$ alkyl and C$_{1-12}$ alkenyl;

each Y is independently a C$_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments a subset of compounds of Formula (I) includes those in which R$_1$ is selected from the group consisting of C$_{5-30}$ alkyl, C$_{5-20}$ alkenyl, —R*YR", —YR", and —R"M'R';

R$_2$ and R$_3$ are independently selected from the group consisting of C$_{1-14}$ alkyl, C$_{2-14}$ alkenyl, —R*YR", —YR", and —R*OR", or R$_2$ and R$_3$, together with the atom to which they are attached, form a heterocycle or carbocycle;

R$_4$ is selected from the group consisting of —(CH$_2$)$_n$Q, —(CH$_2$)$_n$CHQR, —CHQR, and —CQ(R)$_2$, where Q is —N(R)$_2$, and n is selected from 1, 2, 3, 4, and 5;

each R$_5$ is independently selected from the group consisting of C$_{1-3}$ alkyl, C$_{2-3}$ alkenyl, and H;

each R$_6$ is independently selected from the group consisting of C$_{1-3}$ alkyl, C$_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group;

R$_7$ is selected from the group consisting of C$_{1-3}$ alkyl, C$_{2-3}$ alkenyl, and H;

each R is independently selected from the group consisting of C$_{1-3}$ alkyl, C$_{2-3}$ alkenyl, and H;

each R' is independently selected from the group consisting of C$_{1-18}$ alkyl, C$_{2-18}$ alkenyl, —R*YR", —YR", and H;

each R" is independently selected from the group consisting of C$_{3-14}$ alkyl and C$_{3-14}$ alkenyl;

each R* is independently selected from the group consisting of C$_{1-12}$ alkyl and C$_{1-12}$ alkenyl;

each Y is independently a C$_{3-6}$ carbocycle;

each X is independently selected from the group consisting of F, Cl, Br, and I; and m is selected from 5, 6, 7, 8, 9, 10, 11, 12, and 13, or salts or isomers thereof.

In other embodiments a subset of compounds of Formula (I) includes those of Formula (IA):

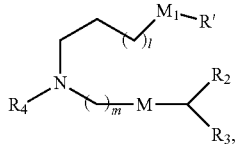

(IA)

or a salt or isomer thereof, wherein l is selected from 1, 2, 3, 4, and 5; m is selected from 5, 6, 7, 8, and 9; M$_1$ is a bond or M'; R$_4$ is unsubstituted C$_{1-3}$ alkyl, or —(CH$_2$)$_n$Q, in which Q is OH, —NHC(S)N(R)$_2$, —NHC(O)N(R)$_2$, —N(R)C(O)R, —N(R)S(O)$_2$R, —N(R)R$_8$, —NHC(=NR$_9$)N(R)$_2$, —NHC(=CHR$_9$)N(R)$_2$, —OC(O)N(R)$_2$, —N(R)C(O)OR, heteroaryl or heterocycloalkyl; M and M' are independently selected from —C(O)O—, —OC(O)—, —C(O)N(R')—, —P(O)(OR')O—, —S—S—, an aryl group, and a heteroaryl group; and R$_2$ and R$_3$ are independently selected from the group consisting of H, C$_{1-14}$ alkyl, and C$_{2-14}$ alkenyl.

In some embodiments the mRNA encoding the influenza virus antigen is present in the lipid nanoparticle in a dosage of 50 micrograms. In some embodiments the mRNA encoding the influenza virus antigen is present in the lipid nanoparticle in a dosage of 75 micrograms. In some embodiments the mRNA encoding the influenza virus antigen is present in the lipid nanoparticle in a dosage of 100 micrograms.

In other aspects the vaccine comprising an mRNA encoding an influenza virus antigen formulated in a lipid nanoparticle, wherein the mRNA encoding the influenza virus antigen is in a dosage of 50 to 100 micrograms and wherein the vaccine produces a protective antigen specific immune response wherein the protective antigen specific immune response is determined by production of a neutralizing antibody titer of at least 2, 3, or 4 times greater than baseline in the human subject.

In other aspects the invention is a method of inducing an antigen specific immune response in a human subject, comprising administering a dose of 10-100 ug of a nucleic acid vaccine comprising an RNA polynucleotide having an open reading frame encoding a hemagglutinin antigen formulated within a cationic lipid nanoparticle to the human subject, wherein a protective antigen specific immune response is induced. In some embodiments the nucleic acid vaccine is a vaccine as described herein.

In some embodiments the protective antigen specific immune response is determined by production of a microneutralization value of greater than 1:20 in the human subject. In other embodiments the protective antigen specific immune response is determined by production of a neutralizing antibody titer of at least 2, 3, or 4 times greater than baseline in the human subject. In other embodiments the protective antigen specific immune response is determined by production of a neutralizing antibody titer of 2-10 times greater than baseline in the human subject. In yet other embodiments the protective antigen specific immune response is determined by production of an HAI titer of at least 1:40, 1:60, 1:80 or 1:90 or is between 1:40 and 1:200 in the human subject.

The protective antigen specific immune response is determined by production of an increase in HAI level of at least 4, 5, or 6 times relative to a baseline HAI level in the human subject in some embodiments.

In other embodiments the method of producing an antigen specific immune response involves a single administration of the vaccine, and wherein the protective immune response is produced with the single administration.

In some embodiments, the RNA polynucleotide is encoded by a nucleic acid sequence selected from any of SEQ ID NOs: 3 and 5 and homologs having at least 80% (e.g., 85%, 90%, 95%, 98%, 99%) identity with such a nucleic acid sequence.

In some embodiments, the RNA polynucleotide is a nucleic acid sequence selected from any of SEQ ID NOs: 2, 6, 7, and 8 and homologs having at least 80% (e.g., 85%, 90%, 95%, 98%, 99%) identity with such a nucleic acid sequence.

In some embodiments, at least one RNA polynucleotide encodes an antigenic polypeptide having at least 80% identity to the amino acid sequence of any of SEQ ID NOs: 1 and 4. In some embodiments, at least one RNA polynucleotide encodes an antigenic polypeptide having at least 85%, 90%, 95%, 96%, 97%, 98%, or 99% identity to the amino acid sequence of any of SEQ ID Nos: 1 and 4.

In any of the herein-described embodiments, the RNA polynucleotides and antigens they encode may further comprise additional sequences, for example, 5' and 3' untranslated regions, one or more linker sequences or one or more sequence tags, such as FLAG-tag and histidine tag.

In some embodiments, the open reading from which the influenza polypeptide is encoded is codon-optimized Some embodiments of the present disclosure provide use of an influenza vaccine that includes at least one ribonucleic acid (RNA) polynucleotide having an open reading frame encoding at least one influenza antigenic polypeptide or an immunogenic fragment thereof, wherein at least 80% (e.g., 85%, 90%, 95%, 98%, 99%, 100%) of the uracil in the open reading frame have a chemical modification, optionally wherein the vaccine is formulated in a lipid nanoparticle. In some embodiments, 100% of the uracil in the open reading frame have a chemical modification. In some embodiments, a chemical modification is in the 5-position of the uracil. In some embodiments, a chemical modification is a N1-methyl pseudouridine. In some embodiments, a chemical modification is a N1-ethyl pseudouridine.

Some embodiments of the present disclosure provide methods of use of an influenzavaccine that is formulated within a cationic lipid nanoparticle. In some embodiments, the cationic lipid nanoparticle comprises a cationic lipid, a PEG-modified lipid, a sterol and a non-cationic lipid.

In some embodiments, the cationic lipid nanoparticle has a molar ratio of about 20-60% cationic lipid, about 5-25% non-cationic lipid, about 25-55% sterol, and about 0.5-15% PEG-modified lipid. In some embodiments, the nanoparticle has a polydiversity value of less than 0.4. In some embodiments, the nanoparticle has a net neutral charge at a neutral pH. In some embodiments, the nanoparticle has a mean diameter of 50-200 nm.

Some embodiments of the present disclosure provide methods of inducing an antigen specific immune response in a subject, comprising administering to the subject an influenza RNA vaccine in an amount effective to produce an antigen specific immune response. In some embodiments, an antigen specific immune response comprises a T cell response or a B cell response. In some embodiments, an antigen specific immune response comprises a T cell response and a B cell response. In some embodiments, a method of producing an antigen specific immune response involves a single administration of the vaccine. In some embodiments, a method further includes administering to the subject a booster dose of the vaccine. In some embodiments, a vaccine is administered to the subject by intradermal or intramuscular injection.

Also provided herein are influenza RNA vaccines for use in a method of inducing an antigen specific immune response in a subject, the method comprising administering the vaccine to the subject in an amount effective to produce an antigen specific immune response.

Further provided herein are uses of influenza RNA vaccines in the manufacture of a medicament for use in a method of inducing an antigen specific immune response in a subject, the method comprising administering the vaccine to the subject in an amount effective to produce an antigen specific immune response.

Further provided herein are methods of preventing or treating influenza infection comprising administering to a subject the vaccine of the present disclosure.

The influenza vaccine disclosed herein may be formulated in an effective amount to produce an antigen specific immune response in a subject.

In some embodiments, an anti-influenza antigenic polypeptide antibody titer produced in the subject is increased by at least 1 log relative to a control. In some embodiments, the anti-influenza antigenic polypeptide antibody titer produced in the subject is increased by 1-3 log relative to a control. In some embodiments, an anti-influenza antigenic polypeptide antibody titer produced in the subject is increased at least 2 times relative to a control. In some embodiments, the anti-influenza antigenic polypeptide antibody titer produced in the subject is increased at least 5 times relative to a control. In some embodiments, the anti-influenza antigenic polypeptide antibody titer produced in the subject is increased at least 10 times relative to a control. In some embodiments, the anti-influenza antigenic polypeptide antibody titer produced in the subject is increased 2-10 times relative to a control.

In some embodiments, the control is an anti-influenza antigenic polypeptide antibody titer produced in a subject who has not been administered influenza vaccine.

In some embodiments, the control is an anti-influenza antigenic polypeptide antibody titer produced in a subject who has been administered a live attenuated or inactivated influenza vaccine.

In some embodiments, the control is an anti-influenza antigenic polypeptide antibody titer produced in a subject who has been administered a recombinant or purified influenza protein vaccine.

In some embodiments, the effective amount is a dose equivalent to an at least 2-fold reduction in the standard of care dose of a recombinant influenza protein vaccine, and wherein an anti-influenza antigenic polypeptide antibody titer produced in the subject is equivalent to an anti-influenza antigenic polypeptide antibody titer produced in a control subject administered the standard of care dose of a recombinant or purified influenza protein vaccine or a live attenuated or inactivated influenza vaccine.

In some embodiments, the effective amount is a dose equivalent to an at least 4-fold reduction in the standard of care dose of a recombinant influenza protein vaccine, and wherein an anti-influenza antigenic polypeptide antibody titer produced in the subject is equivalent to an anti-influenza antigenic polypeptide antibody titer produced in a control subject administered the standard of care dose of a recombinant or purified influenza protein vaccine or a live attenuated or inactivated influenza vaccine.

In some embodiments, the effective amount is a dose equivalent to an at least 10-fold reduction in the standard of care dose of a recombinant influenza protein vaccine, and wherein an anti-influenza antigenic polypeptide antibody titer produced in the subject is equivalent to an anti-influenza antigenic polypeptide antibody titer produced in a control subject administered the standard of care dose of a recombinant or purified influenza protein vaccine or a live attenuated or inactivated influenza vaccine.

In some embodiments, the effective amount is a dose equivalent to an at least 100-fold reduction in the standard of care dose of a recombinant influenza protein vaccine, and wherein an anti-influenza antigenic polypeptide antibody titer produced in the subject is equivalent to an anti-influenza antigenic polypeptide antibody titer produced in a control subject administered the standard of care dose of a recombinant or purified influenza protein vaccine or a live attenuated or inactivated influenza vaccine.

In some embodiments, the effective amount is a dose equivalent to an at least 1000-fold reduction in the standard of care dose of a recombinant influenza protein vaccine, and wherein an anti-influenza antigenic polypeptide antibody titer produced in the subject is equivalent to an anti-influenza antigenic polypeptide antibody titer produced in a control subject administered the standard of care dose of a recombinant or purified influenza protein vaccine or a live attenuated or inactivated influenza vaccine.

In some embodiments, the effective amount is a dose equivalent to a 2-1000-fold reduction in the standard of care dose of a recombinant influenza protein vaccine, and wherein an anti-influenza antigenic polypeptide antibody titer produced in the subject is equivalent to an anti-influenza antigenic polypeptide antibody titer produced in a control subject administered the standard of care dose of a recombinant or purified influenza protein vaccine or a live attenuated or inactivated influenza vaccine.

In some embodiments, the effective amount is a total dose of 50-1000 µg. In some embodiments, the effective amount is a total dose of 100 µg. In some embodiments, the effective amount is a dose of 25 µg administered to the subject a total of two times. In some embodiments, the effective amount is a dose of 100 µg administered to the subject a total of two times. In some embodiments, the effective amount is a dose of 400 µg administered to the subject a total of two times. In some embodiments, the effective amount is a dose of 500 µg administered to the subject a total of two times.

In some embodiments, the effective amount is a total dose of 1-100 µg. In some embodiments, the effective amount is a total dose of 100 µg. In some embodiments, the effective amount is a dose of 25 µg administered to the subject a total of one or two times. In some embodiments, the effective amount is a dose of 100 µg administered to the subject a total of two times. In some embodiments, the effective amount is a dose of 1 µg-10 µg, 1 µg-20 µg, 1 µg-30 µg, 5 µg-10 µg, 5 µg-20 µg, 5 µg-30 µg, 5 µg-40 µg, 5 µg-50 µg, 10 µg-15 µg, 10 µg-20 µg, 10 µg-25 µg, 10 µg-30 µg, 10 µg-40 µg, 10 µg-50 µg, 10 µg-60 µg, 15 µg-20 µg, 15 µg-25 µg, 15 µg-30 µg, 15 µg-40 µg, 15 µg-50 µg, 20 µg-25 µg, 20 µg-30 µg, 20 µg-40 µg 20 µg-50 µg, 20 µg-60 µg, 20 µg-70 µg, 20 µg-75 µg, 30 µg-35 µg, 30 µg-40 µg, 30 µg-45 µg 30 µg-50 µg, 30 µg-60 µg, 30 µg-70 µg, 30 µg-75 µg which may be administered to the subject a total of one or two times or more.

Aspects of the invention provide nucleic acid vaccines comprising one or more RNA polynucleotides having an open reading frame encoding a first antigenic polypeptide, wherein the RNA polynucleotide is present in the formulation for in vivo administration to a host, which confers an antibody titer superior to the criterion for seroprotection for the first antigen for an acceptable percentage of human subjects. In some embodiments, the antibody titer produced by the mRNA vaccines of the invention is a neutralizing antibody titer. In some embodiments the neutralizing antibody titer is greater than a protein vaccine. In other embodiments the neutralizing antibody titer produced by the mRNA vaccines of the invention is greater than an adjuvanted protein vaccine. In yet other embodiments the neutralizing antibody titer produced by the mRNA vaccines of the invention is 1,000-10,000, 1,200-10,000, 1,400-10,000, 1,500-10,000, 1,000-5,000, 1,000-4,000, 1,800-10,000, 2000-10,000, 2,000-5,000, 2,000-3,000, 2,000-4,000, 3,000-5,000, 3,000-4,000, or 2,000-2,500. A neutralization titer is typically expressed as the highest serum dilution required to achieve a 50% reduction in the number of plaques.

In preferred aspects, vaccines of the invention (e.g., LNP-encapsulated mRNA vaccines) produce prophylactically- and/or therapeutically-efficacious levels, concentrations and/or titers of antigen-specific antibodies in the blood or serum of a vaccinated subject. As defined herein, the term antibody titer refers to the amount of antigen-specific antibody produces in a subject, e.g., a human subject. In exemplary embodiments, antibody titer is expressed as the inverse of the greatest dilution (in a serial dilution) that still gives a positive result. In exemplary embodiments, antibody titer is determined or measured by enzyme-linked immunosorbent assay (ELISA). In exemplary embodiments, antibody titer is determined or measured by neutralization assay, e.g., by microneutralization assay. In certain aspects, antibody titer measurement is expressed as a ratio, such as 1:40, 1:100, etc.

In exemplary embodiments of the invention, an efficacious vaccine produces an antibody titer of greater than 1:40, greater that 1:100, greater than 1:400, greater than 1:1000, greater than 1:2000, greater than 1:3000, greater than 1:4000, greater than 1:500, greater than 1:6000, greater than 1:7500, greater than 1:10000. In exemplary embodiments, the antibody titer is produced or reached by 10 days following vaccination, by 20 days following vaccination, by 30 days following vaccination, by 40 days following vaccination, or by 50 or more days following vaccination. In exemplary embodiments, the titer is produced or reached following a single dose of vaccine administered to the subject. In other embodiments, the titer is produced or reached following multiple doses, e.g., following a first and a second dose (e.g., a booster dose.) In exemplary aspects of the invention, antigen-specific antibodies are measured in units of µg/ml or are measured in units of IU/L (International Units per liter) or mIU/ml (milli International Units per ml). In exemplary embodiments of the invention, an efficacious vaccine produces >0.5 µg/ml, >0.1 µg/ml, >0.2 µg/ml, >0.35 µg/ml, >0.5 µg/ml, >1 µg/ml, >2 µg/ml, >5 µg/ml or >10 µg/ml. In exemplary embodiments of the invention, an efficacious vaccine produces >10 mIU/ml, >20 mIU/ml, >50 mIU/ml, >100 mIU/ml, >200 mIU/ml, >500 mIU/ml or >1000 mIU/ml. In exemplary embodiments, the antibody level or concentration is produced or reached by 10 days following vaccination, by 20 days following vaccination, by 30 days following vaccination, by 40 days following vaccination, or by 50 or more days following vaccination. In exemplary embodiments, the level or concentration is produced or reached following a single dose of vaccine administered to the subject. In other embodiments, the level or concentration is produced or reached following multiple doses, e.g., following a first and a second dose (e.g., a booster dose.) In exemplary embodiments, antibody level or concentration is determined or measured by enzyme-linked immunosorbent assay (ELISA). In exemplary embodiments, antibody level or concentration is determined or measured by neutralization assay, e.g., by microneutralization assay.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways. These and other embodiments and aspects will be discussed in greater detail herein.

DETAILED DESCRIPTION

Figure 1:
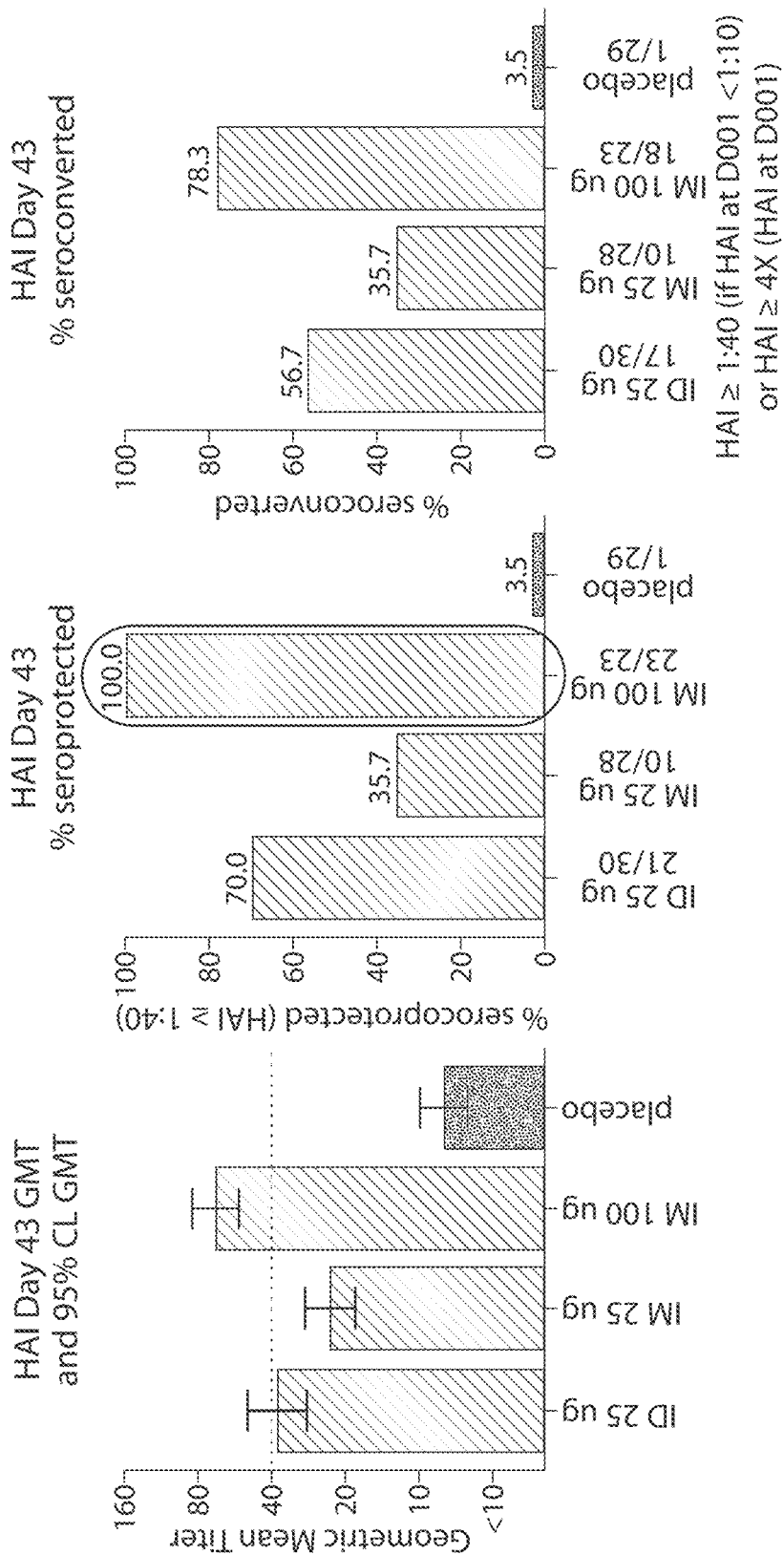
FIG. 1: Graphs show the results of the phase 1 trial in the 100 μg intramuscular (IM) cohort.

Although attempts have been made to produce functional RNA vaccines, including mRNA vaccines and self-replicating RNA vaccines, RNA vaccines which produce effective protective immune responses at safe therapeutic doses in humans have not yet been developed. Quite surprisingly, the inventors have discovered therapeutically effective mRNA vaccines that produce established protective immune responses at unexpectedly low doses. The vaccines produce significantly enhanced, and in many respects synergistic, immune responses including enhanced hemagglutinin antigen generation and functional antibody production with neutralization capability. These results are achieved even when significantly lower doses of the mRNA are administered in comparison with mRNA doses used in other classes of lipid based formulations. The formulations of the invention have demonstrated significant unexpected in vivo immune responses sufficient to establish the efficacy of functional mRNA vaccines as prophylactic and therapeutic agents.

The invention involves, in some aspects, the surprising finding that RNA encoding H7 or H10 antigens and formulated in lipid nanoparticles (LNP) formulations produced protective immune responses at unexpectedly low doses. The efficacy of H7 or H10 antigen mRNA vaccines formulated in LNP was examined in human subjects using several different doses. The results presented herein demonstrate the unexpected superior efficacy of the mRNA vaccines formulated in LNP over other mRNA vaccines even at extremely low doses such as 25 micrograms, which are used to study vaccine efficacy in rodents. The level of protective immune responses produced at these doses and higher doses was higher than that observed with commercially available vaccines under comparable studies.

The data shown in the Examples, demonstrates that significant strong immune responses were observed (anti-viral activity via virus neutralization assay and HA inhibition (HAI)) in human subjects, even following a single low dose of antigen. At several doses with a single or double administration an HAI titer of greater than 40, a dose that is deemed to be sufficient to protect from a lethal challenge of influenza, was obtained. In the H7N9 phase I trial up to 96% of the subjects of the IM arm receiving 2 doses of 25 micrograms showed an increase in protection.

An exemplary RNA sequence for H7N9 is, the sequence of SEQ ID NO: 7: AUGAAUACCCAGAUUCUCGU-GUUCGCCCUCAUCGCUAUCAUCCCAACCAAUGC CGACAAGAUCUGCUUGGGUCAUCAUGCGGUGU-CGAACGGAACCAAGGUCAACA CCCUGACCGAGCGGGGAGUGGAAGUGGU-CAACGCUACUGAAACGGUGGAAAG GAC-UAAUAUCCCACGCAUCUGCUCAAAGG-GAAAGAAAACUGUGGAUCUCGGAC AGUGUGGACUUCUGGGGACCAUCACGGGUC-CACCGCAAUGCGAUCAGUUUCUG GAGUUCAGCGCAGAUCUGAU-CAUCGAGCGCAGAGAAGGGUCCGACGUUUGUU ACCCUGGAAAGUUCGUGAACGAAGAGGCA-CUGCGCCAAAUCUUGCGGGAGAGC GGCGG-CAUUGACAAAGAGGCCAUGGGAUUCACCUA-CUCGGGUAUUCGCACUAA CGGUGCCACUUCUGCGUGCCGGCGUUCCGGGUC-CUCCUUCUAUGCCGAGAUGA AGUGGCUCCUGU-CGAACACCGACAACGCAGC-UUUUCCGCAAAUGACUAAGUCC UACAAAAACACUAGAAAGUCGCCGGCACUGAUC-GUCUGGGGAAUCCAUCACUC CGUGUCUACUGCG-GAGCAAACUAAGCUGUACGGCAGCGGAAACAAG-CUCGUGA CCGUCGGUUCAUCGAACUACCAGCAGAGCUUU-GUGCCAAGCCCCGGAGCGAGG CCCCAGGU-CAACGGGCAGAGCGGACGCAUCGACUUCCA-CUGGCUGAUGCUCAA UCCGAAUGACACCGUGACCUUCUCGUU-CAAUGGCGCCUUCAUCGCACCUGACC GCGCCAGCUUCCUGAGAGGAAAGUCAAUGGG-CAUACAGUCGGGCGUCCAAGUG GAUGC-CAACUGCGAGGGAGACUGCUAUCACUCCGGCG-GAACCAUCAUCUCCAA UUUGCCGUUUCAAAACAUCGA-CUCGCGCGCAGUGGGAAAGUGUCCGCGAUACG UGAAGCAGAGAUCACUGCUGCUGCCACUGG-GAUGAAGAACGUGCCUGAAAUC CCGAAAGGAAGGGGGUUGUUCGGCGC-UAUUGCGGGCUUCAUCGAAAACGGAU GGGAGGGGCUCAUCGAUGGUUGGUACG-GAUUCAGGCACCAGAACGCGCAGGG GGAAGGAACGGCCGCUGAUUACAAGUCAACU-
CAAUCGGCCAUUGACCAAAUCA
CUGGCAAACUGAAUCGCCUGAUCGAAAAGAC-
CAAUCAGCAGUUUGAGUUGAUC
GACAACGAAUUCAACGAAGUG-
GAGAAACAGAUUGGCAAUGUCAUCAAUUGGA
CCAGAGAUAGCAUCACGGAAGUCUGGUCGUA-
CAACGCCGAACUCCUGGUUGCG AUGGAAAAU-
CAACACACCAUCGACCUGGCCGA-
CUCCGAAAUGGACAAACUCUA
CGAGCGGGU-
CAAACGCCAGCUGCGCGAAAACGCAGAAGA
AGAUGGAACCGGAU GCUUCGAGAUCUUU-
CAUAAGUGCGACGACGAUUGCAUGGCCAG-
CAUCCGGAAC AAUACCUACGAUCACUCCA-
AGUACCGGGAGGAAGCGAUGCAAAAUCGGA
UCCA GAUUGACCCGGUCAAACUGUCGUCAGGC-
UACAAGGAUGUGAUCCUUUGGUUCU CAUUCG-
GAGCGUCCUGUUUUAUCCUUCUGGCUAUU-
GUGAUGGGCCUGGUGUUC
AUCUGCGUGAAGAACGGAAACAUGCGCUGCAC-
UAUCUGCAUC. In addition to providing an enhanced immune response, the formulations of the invention generate a rapid immune response following a single dose of antigen. Additionally, the formulations have been shown in an animal model to produce a long lasting protective response. Animals maintained the protective response over most of the their life span, as shown in the Examples provided herein.

The studies described herein use serological methods such as virus neutralization and hemagglutination inhibition (HAI) to evaluate vaccine immunogenicity. Both assays are based on the binding of antibodies to hemagglutinin (HA), the major surface glycoprotein of influenza, and are considered to be reliable methods for predicting vaccine efficacy. Neutralizing antibodies directed against HA are the major mediator of protective immunity against influenza. Virus neutralization gives the most precise answer to the question of whether or not an individual has antibodies that can neutralize the infectivity of a given virus strain. The assay has several additional advantages in detecting antibodies to influenza virus. First, it primarily detects antibodies to the influenza viral HA protein and thus can identify functional strain-specific antibodies in human and animal sera.

Thus, in some embodiments the invention is a method for treating influenza (prophylactically or therapeutically) by administering an mRNA vaccine encoding an influenza antigen. Symptoms of the influenza infection include dry cough, fever, chills, myalgias progressing to respiratory failure and the risk of secondary bacterial infections (e.g., MRSA). Seasonal influenza is ubiquitous and consists of three principal strains (A [HIN1], A [H3N2], and B), which are covered by the annual vaccine. Pandemic flu occurs because the viruses' unique reassortment ability allowing antigenic shift as well as transfer between avian and swine flu strains. One emerging concern in Southeast Asia is the pandemic potential of several new strains. Such pandemic outbreaks have a high mortality rate with few available treatments. Anti-virals only provide symptomatic relief and must be given in the first 48 hours.

In some embodiments, the mRNA vaccines may be used to prevent pandemic influenza by reacting to emerging new strains with the very rapid mRNA vaccine production process. In some embodiments, new mRNA vaccine for treating or prophylactically preventing influenza outbreaks, including for emerging strains (e.g., H7N9 and H10N8), may be produced in less than six weeks, from the time of antigen identification to available vaccine.

In some embodiments a single injection of a single antigen encoding polynucleotide vaccine may provide protection for an entire flu season. In other embodiments the vaccination may protect the individual for several years or longer. In other embodiments the mRNA vaccines may also be used to maintain or restore antigenic memory in a subject or population as part of a vaccination plan.

Influenza vaccine programs against the strains with pandemic potential, H10N8 and H7N9, use influenza targets from naïve patient populations and hemagglutination inhibition (HAI) titers of 1:40 are used by the FDA and WHO to approve seasonal flu vaccines.

In some embodiments, the virus is a strain of Influenza A or Influenza B or combinations thereof. In some embodiments, the strain of Influenza A or Influenza B is associated with birds, pigs, horses, dogs, humans or non-human primates. In some embodiments, the antigenic polypeptide encodes a hemagglutinin protein or fragment thereof. In some embodiments, the hemagglutinin protein is H7 or H10 or a fragment thereof. In some embodiments, the hemagglutinin protein comprises a portion of the head domain (HA1). In some embodiments, the hemagglutinin protein comprises a portion of the cytoplasmic domain. In some embodiments, the truncated hemagglutinin protein. In some embodiments, the protein is a truncated hemagglutinin protein comprises a portion of the transmembrane domain. In some embodiments, the amino acid sequence of the hemagglutinin protein or fragment thereof comprises at least 90%, 91%, 92%, 93%, 94%, 95%, 96%, 97% 98%, or 99% identify with any of the amino acid sequences of SEQ ID NO. 1 or 4. In some embodiments, the virus is selected from the group consisting of H7N9 and H10N8.

The term "polypeptide variant" refers to molecules which differ in their amino acid sequence from a native or reference sequence. The amino acid sequence variants may possess substitutions, deletions, and/or insertions at certain positions within the amino acid sequence, as compared to a native or reference sequence. Ordinarily, variants possess at least 50% identity to a native or reference sequence. In some embodiments, variants share at least 80%, or at least 90% identity with a native or reference sequence.

In some embodiments "variant mimics" are provided. As used herein, the term "variant mimic" is one which contains at least one amino acid that would mimic an activated sequence. For example, glutamate may serve as a mimic for phosphoro-threonine and/or phosphoro-serine. Alternatively, variant mimics may result in deactivation or in an inactivated product containing the mimic, for example, phenylalanine may act as an inactivating substitution for tyrosine; or alanine may act as an inactivating substitution for serine.

"Orthologs" refers to genes in different species that evolved from a common ancestral gene by speciation. Normally, orthologs retain the same function in the course of evolution. Identification of orthologs is critical for reliable prediction of gene function in newly sequenced genomes.

"Analogs" is meant to include polypeptide variants which differ by one or more amino acid alterations, for example, substitutions, additions or deletions of amino acid residues that still maintain one or more of the properties of the parent or starting polypeptide.

The present disclosure provides several types of compositions that are polynucleotide or polypeptide based, including variants and derivatives. These include, for example, substitutional, insertional, deletion and covalent variants and derivatives. The term "derivative" is used synonymously with the term "variant" but generally refers to a molecule that has been modified and/or changed in any way relative to a reference molecule or starting molecule.

As such, polynucleotides encoding peptides or polypeptides containing substitutions, insertions and/or additions, deletions and covalent modifications with respect to reference sequences, in particular the polypeptide sequences disclosed herein, are included within the scope of this disclosure. For example, sequence tags or amino acids, such as one or more lysines, can be added to peptide sequences (e.g., at the N-terminal or C-terminal ends). Sequence tags can be used for peptide detection, purification or localization. Lysines can be used to increase peptide solubility or to allow for biotinylation. Alternatively, amino acid residues located at the carboxy and amino terminal regions of the amino acid sequence of a peptide or protein may optionally be deleted providing for truncated sequences. Certain amino acids (e.g., C-terminal or N-terminal residues) may alternatively be deleted depending on the use of the sequence, as for example, expression of the sequence as part of a larger sequence which is soluble, or linked to a solid support.

"Substitutional variants" when referring to polypeptides are those that have at least one amino acid residue in a native or starting sequence removed and a different amino acid inserted in its place at the same position. Substitutions may be single, where only one amino acid in the molecule has been substituted, or they may be multiple, where two or more amino acids have been substituted in the same molecule.

As used herein the term "conservative amino acid substitution" refers to the substitution of an amino acid that is normally present in the sequence with a different amino acid of similar size, charge, or polarity. Examples of conservative substitutions include the substitution of a non-polar (hydrophobic) residue such as isoleucine, valine and leucine for another non-polar residue. Likewise, examples of conservative substitutions include the substitution of one polar (hydrophilic) residue for another such as between arginine and lysine, between glutamine and asparagine, and between glycine and serine. Additionally, the substitution of a basic residue such as lysine, arginine or histidine for another, or the substitution of one acidic residue such as aspartic acid or glutamic acid for another acidic residue are additional examples of conservative substitutions. Examples of non-conservative substitutions include the substitution of a non-polar (hydrophobic) amino acid residue such as isoleucine, valine, leucine, alanine, methionine for a polar (hydrophilic) residue such as cysteine, glutamine, glutamic acid or lysine and/or a polar residue for a non-polar residue.

"Features" when referring to polypeptide or polynucleotide are defined as distinct amino acid sequence-based or nucleotide-based components of a molecule respectively. Features of the polypeptides encoded by the polynucleotides include surface manifestations, local conformational shape, folds, loops, half-loops, domains, half-domains, sites, termini or any combination thereof.

As used herein when referring to polypeptides the term "domain" refers to a motif of a polypeptide having one or more identifiable structural or functional characteristics or properties (e.g., binding capacity, serving as a site for protein-protein interactions).

As used herein when referring to polypeptides the terms "site" as it pertains to amino acid based embodiments is used synonymously with "amino acid residue" and "amino acid side chain." As used herein when referring to polynucleotides the terms "site" as it pertains to nucleotide based embodiments is used synonymously with "nucleotide." A site represents a position within a peptide or polypeptide or polynucleotide that may be modified, manipulated, altered, derivatized or varied within the polypeptide or polynucleotide based molecules.

As used herein the terms "termini" or "terminus" when referring to polypeptides or polynucleotides refers to an extremity of a polypeptide or polynucleotide respectively. Such extremity is not limited only to the first or final site of the polypeptide or polynucleotide but may include additional amino acids or nucleotides in the terminal regions. Polypeptide-based molecules may be characterized as having both an N-terminus (terminated by an amino acid with a free amino group (NH2)) and a C-terminus (terminated by an amino acid with a free carboxyl group (COOH)). Proteins are in some cases made up of multiple polypeptide chains brought together by disulfide bonds or by non-covalent forces (multimers, oligomers). These proteins have multiple N- and C-termini. Alternatively, the termini of the polypeptides may be modified such that they begin or end, as the case may be, with a non-polypeptide based moiety such as an organic conjugate.

As recognized by those skilled in the art, protein fragments, functional protein domains, and homologous proteins are also considered to be within the scope of polypeptides of interest. For example, provided herein is any protein fragment (meaning a polypeptide sequence at least one amino acid residue shorter than a reference polypeptide sequence but otherwise identical) of a reference protein 10, 20, 30, 40, 50, 60, 70, 80, 90, 100 or greater than 100 amino acids in length. In another example, any protein that includes a stretch of 20, 30, 40, 50, or 100 amino acids which are 40%, 50%, 60%, 70%, 80%, 90%, 95%, or 100% identical to any of the sequences described herein can be utilized in accordance with the disclosure. In some embodiments, a polypeptide includes 2, 3, 4, 5, 6, 7, 8, 9, 10, or more mutations as shown in any of the sequences provided or referenced herein.

In some embodiments, an influenza vaccine comprises an mRNA ORF having a nucleotide sequence identified by any one of the nucleic acid sequences provided herein (see e.g., Sequence Listing), or having a nucleotide sequence at least 80%, at least 85%, at least 90%, at least 95%, at least 96%, at least 97%, at least 98%, or at least 99% identical to a nucleotide sequence identified by any one of the sequence provided herein.

In some embodiments, an influenza vaccine comprises an mRNA ORF having a nucleotide sequence encoding any one of the amino acid sequences provided herein (see e.g., Sequence Listing), or having a nucleotide sequence at least 80%, at least 85%, at least 90%, at least 95%, at least 96%, at least 97%, at least 98%, or at least 99% identical to a nucleotide sequence encoding any one of the amino acid sequences provided herein, or having a nucleotide sequence identical to a nucleotide sequence encoding any one of the amino acid sequences or having at least 80%, at least 85%, at least 90%, at least 95%, at least 96%, at least 97%, at least 98%, or at least 99% identity thereto.

Polypeptide or polynucleotide molecules of the present disclosure may share a certain degree of sequence similarity or identity with the reference molecules (e.g., reference polypeptides or reference polynucleotides), for example, with art-described molecules (e.g., engineered or designed molecules or wild-type molecules). The term "identity" as known in the art, refers to a relationship between the sequences of two or more polypeptides or polynucleotides, as determined by comparing the sequences. In the art, identity also means the degree of sequence relatedness between them as determined by the number of matches between strings of two or more amino acid residues or nucleic acid residues. Identity measures the percent of identical matches between the smaller of two or more sequences with gap alignments (if any) addressed by a particular mathematical model or computer program (e.g., "algorithms"). Identity of related peptides can be readily calculated by known methods. "% identity" as it applies to polypeptide or polynucleotide sequences is defined as the percentage of residues (amino acid residues or nucleic acid residues) in the candidate amino acid or nucleic acid sequence that are identical with the residues in the amino acid sequence or nucleic acid sequence of a second sequence after aligning the sequences and introducing gaps, if necessary, to achieve the maximum percent identity. Methods and computer programs for the alignment are well known in the art. It is understood that identity depends on a calculation of percent identity but may differ in value due to gaps and penalties introduced in the calculation. Generally, variants of a particular polynucleotide or polypeptide have at least 40%, 45%, 50%, 55%, 60%, 65%, 70%, 75%, 80%, 85%, 90%, 91%, 92%, 93%, 94%, 95%, 96%, 97%, 98%, 99% but less than 100% sequence identity to that particular reference polynucleotide or polypeptide as determined by sequence alignment programs and parameters described herein and known to those skilled in the art. Such tools for alignment include those of the BLAST suite (Stephen F. Altschul, et al (1997), "Gapped BLAST and PSI-BLAST: a new generation of protein database search programs", Nucleic Acids Res. 25:3389-3402). Another popular local alignment technique is based on the Smith-Waterman algorithm (Smith, T. F. & Waterman, M. S. (1981) "Identification of common molecular subsequences." J. Mol. Biol. 147:195-197.) A general global alignment technique based on dynamic programming is the Needleman-Wunsch algorithm (Needleman, S. B. & Wunsch, C. D. (1970) "A general method applicable to the search for similarities in the amino acid sequences of two proteins." J. Mol. Biol. 48:443-453). More recently a Fast Optimal Global Sequence Alignment Algorithm (FOGSAA) has been developed that purportedly produces global alignment of nucleotide and protein sequences faster than other optimal global alignment methods, including the Needleman-Wunsch algorithm. Other tools are described herein, specifically in the definition of "identity" below.

As used herein, the term "homology" refers to the overall relatedness between polymeric molecules, e.g. between nucleic acid molecules (e.g. DNA molecules and/or RNA molecules) and/or between polypeptide molecules. Polymeric molecules (e.g. nucleic acid molecules (e.g. DNA molecules and/or RNA molecules) and/or polypeptide molecules) that share a threshold level of similarity or identity determined by alignment of matching residues are termed homologous. Homology is a qualitative term that describes a relationship between molecules and can be based upon the quantitative similarity or identity. Similarity or identity is a quantitative term that defines the degree of sequence match between two compared sequences. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% identical or similar. The term "homologous" necessarily refers to a comparison between at least two sequences (polynucleotide or polypeptide sequences). Two polynucleotide sequences are considered homologous if the polypeptides they encode are at least 50%, 60%, 70%, 80%, 90%, 95%, or even 99% for at least one stretch of at least 20 amino acids. In some embodiments, homologous polynucleotide sequences are characterized by the ability to encode a stretch of at least 4-5 uniquely specified amino acids. For polynucleotide sequences less than 60 nucleotides in length, homology is determined by the ability to encode a stretch of at least 4-5 uniquely specified amino acids. Two protein sequences are considered homologous if the proteins are at least 50%, 60%, 70%, 80%, or 90% identical for at least one stretch of at least 20 amino acids.

Homology implies that the compared sequences diverged in evolution from a common origin. The term "homolog" refers to a first amino acid sequence or nucleic acid sequence (e.g., gene (DNA or RNA) or protein sequence) that is related to a second amino acid sequence or nucleic acid sequence by descent from a common ancestral sequence. The term "homolog" may apply to the relationship between genes and/or proteins separated by the event of speciation or to the relationship between genes and/or proteins separated by the event of genetic duplication. "Orthologs" are genes (or proteins) in different species that evolved from a common ancestral gene (or protein) by speciation. Typically, orthologs retain the same function in the course of evolution. "Paralogs" are genes (or proteins) related by duplication within a genome. Orthologs retain the same function in the course of evolution, whereas paralogs evolve new functions, even if these are related to the original one.

The term "identity" refers to the overall relatedness between polymeric molecules, for example, between polynucleotide molecules (e.g. DNA molecules and/or RNA molecules) and/or between polypeptide molecules. Calculation of the percent identity of two polynucleic acid sequences, for example, can be performed by aligning the two sequences for optimal comparison purposes (e.g., gaps can be introduced in one or both of a first and a second nucleic acid sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. For example, the percent identity between two nucleic acid sequences can be determined using methods such as those described in Computational Molecular Biology, Lesk, A. M., ed., Oxford University Press, New York, 1988; Biocomputing: Informatics and Genome Projects, Smith, D. W., ed., Academic Press, New York, 1993; Sequence Analysis in Molecular Biology, von Heinje, G., Academic Press, 1987; Computer Analysis of Sequence Data, Part I, Griffin, A. M., and Griffin, H. G., eds., Humana Press, New Jersey, 1994; and Sequence Analysis Primer, Gribskov, M. and Devereux, J., eds., M Stockton Press, New York, 1991; each of which is incorporated herein by reference. For example, the percent identity between two nucleic acid sequences can be determined using the algorithm of Meyers and Miller (CABIOS, 1989, 4:11-17), which has been incorporated into the ALIGN program (version 2.0) using a PAM120 weight residue table, a gap length penalty of 12 and a gap penalty of 4. The percent identity between two nucleic acid sequences can, alternatively, be determined using the GAP program in the GCG software package using an NWSgapdna.CMP matrix. Methods commonly employed to determine percent identity between sequences include, but are not limited to those disclosed in Carillo, H., and Lipman, D., SIAM J Applied Math., 48:1073 (1988); incorporated herein by reference. Techniques for determining identity are codified in publicly available computer programs. Exemplary computer software to determine homology between two sequences include, but are not limited to, GCG program package, Devereux, J., et al., Nucleic Acids Research, 12(1), 387 (1984)), BLASTP, BLASTN, and FASTA Altschul, S. F. et al., J. Molec. Biol., 215, 403 (1990)).

In some embodiments, the polypeptides further comprise additional sequences or functional domains. For example, the influenza polypeptides of the present disclosure may comprise one or more linker sequences. In some embodiments, the influenza of the present invention may comprise a polypeptide tag, such as an affinity tag (chitin binding protein (CBP), maltose binding protein (MBP), glutathione-S-transferase (GST), SBP-tag, Strep-tag, AviTag, Calmodulin-tag); solubilization tag; chromatography tag (polyanionic amino acid tag, such as FLAG-tag); epitope tag (short peptide sequences that bind to high-affinity antibodies, such as V5-tag, Myc-tag, VSV-tag, Xpress tag, E-tag, S-tag, and HA-tag); fluorescence tag (e.g., GFP). In some embodiments, the influenza of the present invention may comprise an amino acid tag, such as one or more lysines, histidines, or glutamates, which can be added to the polypeptide sequences (e.g., at the N-terminal or C-terminal ends). Lysines can be used to increase peptide solubility or to allow for biotinylation. Protein and amino acid tags are peptide sequences genetically grafted onto a recombinant protein. Sequence tags are attached to proteins for various purposes, such as peptide purification, identification, or localization, for use in various applications including, for example, affinity purification, protein array, western blotting, immunofluorescence, and immunoprecipitation. Such tags are subsequently removable by chemical agents or by enzymatic means, such as by specific proteolysis or intein splicing.

Alternatively, amino acid residues located at the carboxy and amino terminal regions of the amino acid sequence of a peptide or protein may optionally be deleted providing for truncated sequences. Certain amino acids (e.g., C-terminal or N-terminal residues) may alternatively be deleted depending on the use of the sequence, as for example, expression of the sequence as part of a larger sequence which is soluble, or linked to a solid support.

Signal Peptides

In some embodiments, antigenic polypeptides encoded by influenza nucleic acids comprise a signal peptide. Signal peptides, comprising the N-terminal 15-60 amino acids of proteins, are typically needed for the translocation across the membrane on the secretory pathway and thus universally control the entry of most proteins both in eukaryotes and prokaryotes to the secretory pathway. Signal peptides generally include three regions: an N-terminal region of differing length, which usually comprises positively charged amino acids, a hydrophobic region, and a short carboxy-terminal peptide region. In eukaryotes, the signal peptide of a nascent precursor protein (pre-protein) directs the ribosome to the rough endoplasmic reticulum (ER) membrane and initiates the transport of the growing peptide chain across it. The signal peptide is not responsible for the final destination of the mature protein, however. Secretory proteins devoid of further address tags in their sequence are by default secreted to the external environment. Signal peptides are cleaved from precursor proteins by an endoplasmic reticulum (ER)-resident signal peptidase or they remain uncleaved and function as a membrane anchor. During recent years, a more advanced view of signal peptides has evolved, showing that the functions and immunodorminance of certain signal peptides are much more versatile than previously anticipated.

Influenza vaccines of the present disclosure may comprise, for example, RNA polynucleotides encoding an artificial signal peptide, wherein the signal peptide coding sequence is operably linked to and is in frame with the coding sequence of the influenza antigenic polypeptide. Thus, influenza vaccines of the present disclosure, in some embodiments, produce an antigenic polypeptide comprising an influenza antigenic polypeptide fused to a signal peptide. In some embodiments, a signal peptide is fused to the N-terminus of the influenza antigenic polypeptide. In some embodiments, a signal peptide is fused to the C-terminus of the influenza antigenic polypeptide.

In some embodiments, the signal peptide fused to the influenza antigenic polypeptide is an artificial signal peptide. In some embodiments, an artificial signal peptide fused to the influenza antigenic polypeptide encoded by the influenza RNA vaccine is obtained from an immunoglobulin protein, e.g., an IgE signal peptide or an IgG signal peptide. In some embodiments, a signal peptide fused to the influenza antigenic polypeptide encoded by an influenza mRNA vaccine is an Ig heavy chain epsilon-1 signal peptide (IgE HC SP) having the sequence of: MDWTWILFLVAAATRVHS (SEQ ID NO: 18). In some embodiments, a signal peptide fused to an influenza antigenic polypeptide encoded by the influenza RNA vaccine is an IgGk chain V-III region HAH signal peptide (IgGk SP) having the sequence of METPAQLL-FLLLLWLPDTTG (SEQ ID NO: 19). In some embodiments, a signal peptide fused to the influenza antigenic polypeptide encoded by an influenza RNA vaccine has an amino acid sequence set forth in SEQ ID NO: 18 or SEQ ID NO: 19. The examples disclosed herein are not meant to be limiting and any signal peptide that is known in the art to facilitate targeting of a protein to ER for processing and/or targeting of a protein to the cell membrane may be used in accordance with the present disclosure.

A signal peptide may have a length of 15-60 amino acids. For example, a signal peptide may have a length of 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 amino acids. In some embodiments, a signal peptide may have a length of 20-60, 25-60, 30-60, 35-60, 40-60, 45-60, 50-60, 55-60, 15-55, 20-55, 25-55, 30-55, 35-55, 40-55, 45-55, 50-55, 15-50, 20-50, 25-50, 30-50, 35-50, 40-50, 45-50, 15-45, 20-45, 25-45, 30-45, 35-45, 40-45, 15-40, 20-40, 25-40, 30-40, 35-40, 15-35, 20-35, 25-35, 30-35, 15-30, 20-30, 25-30, 15-25, 20-25, or 15-20 amino acids.

A signal peptide is typically cleaved from the nascent polypeptide at the cleavage junction during ER processing. The mature influenza antigenic polypeptide produce by influenza RNA vaccine of the present disclosure typically does not comprise a signal peptide.

Fusion Proteins

In some embodiments, an Influenza RNA vaccine of the present disclosure includes an RNA encoding an antigenic fusion protein. Thus, the encoded antigen or antigens may include two or more proteins (e.g., protein and/or protein fragment) joined together. Alternatively, the protein to which a protein antigen is fused does not promote a strong immune response to itself, but rather to the influenza antigen. Antigenic fusion proteins, in some embodiments, retain the functional property from each original protein.

Scaffold Moieties

The RNA (e.g., mRNA) vaccines as provided herein, in some embodiments, encode fusion proteins which comprise influenza antigens linked to scaffold moieties. In some embodiments, such scaffold moieties impart desired properties to an antigen encoded by a nucleic acid of the disclosure. For example scaffold proteins may improve the immunogenicity of an antigen, e.g., by altering the structure of the antigen, altering the uptake and processing of the antigen, and/or causing the antigen to bind to a binding partner.

In some embodiments, the scaffold moiety is protein that can self-assemble into protein nanoparticles that are highly symmetric, stable, and structurally organized, with diameters of 10-150 nm, a highly suitable size range for optimal interactions with various cells of the immune system. In one embodiment, viral proteins or virus-like particles can be used to form stable nanoparticle structures. Examples of such viral proteins are known in the art. For example, in some embodiments, the scaffold moiety is a hepatitis B surface antigen (HBsAg). HBsAg forms spherical particles with an average diameter of ~22 nm and which lacked nucleic acid and hence are non-infectious (Lopez-Sagaseta, J. et al. *Computational and Structural Biotechnology Journal* 14 (2016) 58-68). In some embodiments, the scaffold moiety is a hepatitis B core antigen (HBcAg) self-assembles into particles of 24-31 nm diameter, which resembled the viral cores obtained from HBV-infected human liver. HBcAg produced in self-assembles into two classes of differently sized nanoparticles of 300 Å and 360 Å diameter, corresponding to 180 or 240 protomers. In some embodiments an influenza antigen is fused to HBsAG or HBcAG to facilitate self-assembly of nanoparticles displaying the influenza antigen.

In another embodiment, bacterial protein platforms may be used. Non-limiting examples of these self-assembling proteins include ferritin, lumazine and encapsulin.

Ferritin is a protein whose main function is intracellular iron storage. Ferritin is made of 24 subunits, each composed of a four-alpha-helix bundle, that self-assemble in a quaternary structure with octahedral symmetry (Cho K. J. et al. *J Mol Biol.* 2009; 390:83-98). Several high-resolution structures of ferritin have been determined, confirming that *Helicobacter pylori* ferritin is made of 24 identical protomers, whereas in animals, there are ferritin light and heavy chains that can assemble alone or combine with different ratios into particles of 24 subunits (Granier T. et al. *J Biol Inorg Chem.* 2003; 8:105-111; Lawson D. M. et al. *Nature.* 1991; 349:541-544). Ferritin self-assembles into nanoparticles with robust thermal and chemical stability. Thus, the ferritin nanoparticle is well-suited to carry and expose antigens.

Lumazine synthase (LS) is also well-suited as a nanoparticle platform for antigen display. LS, which is responsible for the penultimate catalytic step in the biosynthesis of riboflavin, is an enzyme present in a broad variety of organisms, including archaea, bacteria, fungi, plants, and eubacteria (Weber S. E. *Flavins and Flavoproteins*. Methods and Protocols, Series: Methods in Molecular Biology. 2014). The LS monomer is 150 amino acids long, and consists of beta-sheets along with tandem alpha-helices flanking its sides. A number of different quaternary structures have been reported for LS, illustrating its morphological versatility: from homopentamers up to symmetrical assemblies of 12 pentamers forming capsids of 150 Å diameter. Even LS cages of more than 100 subunits have been described (Zhang X. et al. *J Mol Biol.* 2006; 362:753-770).

Encapsulin, a novel protein cage nanoparticle isolated from thermophile *Thermotoga maritima*, may also be used as a platform to present antigens on the surface of self-assembling nanoparticles. Encapsulin is assembled from 60 copies of identical 31 kDa monomers having a thin and icosahedral T=1 symmetric cage structure with interior and exterior diameters of 20 and 24 nm, respectively (Sutter M. et al. *Nat Struct Mol Biol.* 2008, 15: 939-947). Although the exact function of encapsulin in *T. maritima* is not clearly understood yet, its crystal structure has been recently solved and its function was postulated as a cellular compartment that encapsulates proteins such as DyP (Dye decolorizing peroxidase) and Flp (Ferritin like protein), which are involved in oxidative stress responses (Rahmanpour R. et al. *FEBS J.* 2013, 280: 2097-2104).

Linkers and Cleavable Peptides

In some embodiments, the mRNAs of the disclosure encode more than one polypeptide, referred to herein as fusion proteins. In some embodiments, the mRNA further encodes a linker located between at least one or each domain of the fusion protein. The linker can be, for example, a cleavable linker or protease-sensitive linker. In some embodiments, the linker is selected from the group consisting of F2A linker, P2A linker, T2A linker, E2A linker, and combinations thereof. This family of self-cleaving peptide linkers, referred to as 2A peptides, has been described in the art (see for example, Kim, J. H. et al. (2011) *PLoS ONE* 6:e18556). In some embodiments, the linker is an F2A linker. In some embodiments, the linker is a GGGS linker (SEQ ID NO: 23). In some embodiments, the fusion protein contains three domains with intervening linkers, having the structure: domain-linker-domain-linker-domain.

Cleavable linkers known in the art may be used in connection with the disclosure. Exemplary such linkers include: F2A linkers, T2A linkers, P2A linkers, E2A linkers (See, e.g., WO2017127750). The skilled artisan will appreciate that other art-recognized linkers may be suitable for use in the constructs of the disclosure (e.g., encoded by the nucleic acids of the disclosure). The skilled artisan will likewise appreciate that other polycistronic constructs (mRNA encoding more than one antigen/polypeptide separately within the same molecule) may be suitable for use as provided herein.

Sequence Optimization

In one embodiment, an ORF encoding an antigen of the disclosure is codon optimized. Codon optimization methods are known in the art. For example, an ORF of any one or more of the sequences provided herein may be codon optimized. Codon optimization, in some embodiments, may be used to match codon frequencies in target and host organisms to ensure proper folding; bias GC content to increase mRNA stability or reduce secondary structures; minimize tandem repeat codons or base runs that may impair gene construction or expression; customize transcriptional and translational control regions; insert or remove protein trafficking sequences; remove/add post translation modification sites in encoded protein (e.g., glycosylation sites); add, remove or shuffle protein domains; insert or delete restriction sites; modify ribosome binding sites and mRNA degradation sites; adjust translational rates to allow the various domains of the protein to fold properly; or reduce or eliminate problem secondary structures within the polynucleotide. Codon optimization tools, algorithms and services are known in the art—non-limiting examples include services from GeneArt (Life Technologies), DNA2.0 (Menlo Park CA) and/or proprietary methods. In some embodiments, the open reading frame (ORF) sequence is optimized using optimization algorithms.

In some embodiments, a codon optimized sequence shares less than 95% sequence identity to a naturally-occurring or wild-type sequence ORF (e.g., a naturally-occurring or wild-type mRNA sequence encoding an Influenza antigen). In some embodiments, a codon optimized sequence shares less than 90% sequence identity to a naturally-occurring or wild-type sequence (e.g., a naturally-occurring or wild-type mRNA sequence encoding an Influenza antigen). In some embodiments, a codon optimized sequence shares less than 85% sequence identity to a naturally-occurring or wild-type sequence (e.g., a naturally-occurring or wild-type mRNA sequence encoding an Influenza antigen). In some embodiments, a codon optimized sequence shares less than 80% sequence identity to a naturally-occurring or wild-type sequence (e.g., a naturally-occurring or wild-type mRNA sequence encoding an Influenza antigen). In some embodiments, a codon optimized sequence shares less than 75% sequence identity to a naturally-occurring or wild-type sequence (e.g., a naturally-occurring or wild-type mRNA sequence encoding an Influenza antigen).

In some embodiments, a codon optimized sequence shares between 65% and 85% (e.g., between about 67% and about 85% or between about 67% and about 80%) sequence identity to a naturally-occurring or wild-type sequence (e.g., a naturally-occurring or wild-type mRNA sequence encoding an Influenza antigen). In some embodiments, a codon optimized sequence shares between 65% and 75% or about 80% sequence identity to a naturally-occurring or wild-type sequence (e.g., a naturally-occurring or wild-type mRNA sequence encoding an Influenza antigen).

In some embodiments, a codon-optimized sequence encodes an antigen that is as immunogenic as, or more immunogenic than (e.g., at least 10%, at least 20%, at least 30%, at least 40%, at least 50%, at least 100%, or at least 200% more), than an Influenza antigen encoded by a non-codon-optimized)sequence.

When transfected into mammalian cells, the modified mRNAs have a stability of between 12-18 hours, or greater than 18 hours, e.g., 24, 36, 48, 60, 72, or greater than 72 hours.

In some embodiments, a codon optimized RNA may be one in which the levels of G/C are enhanced. The G/C-content of nucleic acid molecules (e.g., mRNA) may influence the stability of the RNA. RNA having an increased amount of guanine (G) and/or cytosine (C) residues may be functionally more stable than RNA containing a large amount of adenine (A) and thymine (T) or uracil (U) nucleotides. As an example, WO02/098443 discloses a pharmaceutical composition containing an mRNA stabilized by sequence modifications in the translated region. Due to the degeneracy of the genetic code, the modifications work by substituting existing codons for those that promote greater RNA stability without changing the resulting amino acid. The approach is limited to coding regions of the RNA.

Chemically Unmodified Nucleotides

In some embodiments, at least one RNA (e.g., mRNA) of a Influenza vaccines of the present disclosure is not chemically modified and comprises the standard ribonucleotides consisting of adenosine, guanosine, cytosine and uridine. In some embodiments, nucleotides and nucleosides of the present disclosure comprise standard nucleoside residues such as those present in transcribed RNA (e.g. A, G, C, or U). In some embodiments, nucleotides and nucleosides of the present disclosure comprise standard deoxyribonucleosides such as those present in DNA (e.g. dA, dG, dC, or dT).

Chemical Modifications

Influenza RNA vaccines of the present disclosure comprise, in some embodiments, at least one ribonucleic acid (RNA) polynucleotide having an open reading frame encoding at least one influenza antigenic polypeptide, or an immunogenic fragment thereof, that comprises at least one chemical modification.

The terms "chemical modification" and "chemically modified" refer to modification with respect to adenosine (A), guanosine (G), uridine (U), thymidine (T) or cytidine (C) ribonucleosides or deoxyribonucleosides in at least one of their position, pattern, percent or population. Generally, these terms do not refer to the ribonucleotide modifications in naturally occurring 5'-terminal mRNA cap moieties. With respect to a polypeptide, the term "modification" refers to a modification relative to the canonical set 20 amino acids. Polypeptides, as provided herein, are also considered "modified" of they contain amino acid substitutions, insertions or a combination of substitutions and insertions.

Polynucleotides (e.g., RNA polynucleotides, such as mRNA polynucleotides), in some embodiments, comprise various (more than one) different modifications. In some embodiments, a particular region of a polynucleotide contains one, two or more (optionally different) nucleoside or nucleotide modifications. In some embodiments, a modified RNA polynucleotide (e.g., a modified mRNA polynucleotide), introduced to a cell or organism, exhibits reduced degradation in the cell or organism, respectively, relative to an unmodified polynucleotide. In some embodiments, a modified RNA polynucleotide (e.g., a modified mRNA polynucleotide), introduced into a cell or organism, may exhibit reduced immunogenicity in the cell or organism, respectively (e.g., a reduced innate response).

Modifications of polynucleotides include, without limitation, those described herein. Polynucleotides (e.g., RNA polynucleotides, such as mRNA polynucleotides) may comprise modifications that are naturally-occurring, non-naturally-occurring or the polynucleotide may comprise a combination of naturally-occurring and non-naturally-occurring modifications. Polynucleotides may include any useful modification, for example, of a sugar, a nucleobase, or an internucleoside linkage (e.g., to a linking phosphate, to a phosphodiester linkage or to the phosphodiester backbone).

Polynucleotides (e.g., RNA polynucleotides, such as mRNA polynucleotides), in some embodiments, comprise non-natural modified nucleotides that are introduced during synthesis or post-synthesis of the polynucleotides to achieve desired functions or properties. The modifications may be present on an internucleotide linkages, purine or pyrimidine bases, or sugars. The modification may be introduced with chemical synthesis or with a polymerase enzyme at the terminal of a chain or anywhere else in the chain. Any of the regions of a polynucleotide may be chemically modified.

The present disclosure provides for modified nucleosides and nucleotides of a polynucleotide (e.g., RNA polynucleotides, such as mRNA polynucleotides). A "nucleoside" refers to a compound containing a sugar molecule (e.g., a pentose or ribose) or a derivative thereof in combination with an organic base (e.g., a purine or pyrimidine) or a derivative thereof (also referred to herein as "nucleobase"). A "nucleotide" refers to a nucleoside, including a phosphate group. Modified nucleotides may by synthesized by any useful method, such as, for example, chemically, enzymatically, or recombinantly, to include one or more modified or non-natural nucleosides. Polynucleotides may comprise a region or regions of linked nucleosides. Such regions may have variable backbone linkages. The linkages may be standard phosphodiester linkages, in which case the polynucleotides would comprise regions of nucleotides.

Modified nucleotide base pairing encompasses not only the standard adenosine-thymine, adenosine-uracil, or guanosine-cytosine base pairs, but also base pairs formed between nucleotides and/or modified nucleotides comprising non-standard or modified bases, wherein the arrangement of hydrogen bond donors and hydrogen bond acceptors permits hydrogen bonding between a non-standard base and a standard base or between two complementary non-standard base structures. One example of such non-standard base pairing is the base pairing between the modified nucleotide inosine and adenine, cytosine or uracil. Any combination of base/sugar or linker may be incorporated into polynucleotides of the present disclosure.

In some embodiments, polynucleotides (e.g., RNA polynucleotides, such as mRNA polynucleotides) include a combination of at least two (e.g., 2, 3, 4 or more) of the aforementioned modified nucleobases.

In some embodiments, modified nucleobases in polynucleotides (e.g., RNA polynucleotides, such as mRNA polynucleotides) are selected from the group consisting of pseudouridine (ψ), N1-methylpseudouridine (m$^1$ψ), N1-ethylpseudouridine, 2-thiouridine, 4'-thiouridine, 5-methylcytosine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methoxyuridine and 2'-O-methyl uridine. In some embodiments, polynucleotides (e.g., RNA polynucleotides, such as mRNA polynucleotides) include a combination of at least two (e.g., 2, 3, 4 or more) of the aforementioned modified nucleobases.

In some embodiments, modified nucleobases in polynucleotides (e.g., RNA polynucleotides, such as mRNA polynucleotides) are selected from the group consisting of 1-methyl-pseudouridine (m$^1$ψ), 5-methoxy-uridine (mo$^5$U), 5-methyl-cytidine (m$^5$C), pseudouridine (ψ), α-thio-guanosine and α-thio-adenosine. In some embodiments, polynucleotides includes a combination of at least two (e.g., 2, 3, 4 or more) of the aforementioned modified nucleobases.

In some embodiments, polynucleotides (e.g., RNA polynucleotides, such as mRNA polynucleotides) comprise pseudouridine (ψ) and 5-methyl-cytidine (m$^5$C). In some embodiments, polynucleotides (e.g., RNA polynucleotides, such as mRNA polynucleotides) comprise 1-methyl-pseudouridine (m$^1$ψ). In some embodiments, polynucleotides (e.g., RNA polynucleotides, such as mRNA polynucleotides) comprise 1-methyl-pseudouridine (m$^1$ψ) and 5-methyl-cytidine (m$^5$C). In some embodiments, polynucleotides (e.g., RNA polynucleotides, such as mRNA polynucleotides) comprise 2-thiouridine (s$^2$U). In some embodiments, polynucleotides (e.g., RNA polynucleotides, such as mRNA polynucleotides) comprise 2-thiouridine and 5-methyl-cytidine (m$^5$C). In some embodiments, polynucleotides (e.g., RNA polynucleotides, such as mRNA polynucleotides) comprise methoxy-uridine (mo$^5$U). In some embodiments, polynucleotides (e.g., RNA polynucleotides, such as mRNA polynucleotides) comprise 5-methoxy-uridine (mo$^5$U) and 5-methyl-cytidine (m$^5$C). In some embodiments, polynucleotides (e.g., RNA polynucleotides, such as mRNA polynucleotides) comprise 2'-O-methyl uridine. In some embodiments polynucleotides (e.g., RNA polynucleotides, such as mRNA polynucleotides) comprise 2'-O-methyl uridine and 5-methyl-cytidine (m$^5$C). In some embodiments, polynucleotides (e.g., RNA polynucleotides, such as mRNA polynucleotides) comprise N6-methyl-adenosine (m$^6$A). In some embodiments, polynucleotides (e.g., RNA polynucleotides, such as mRNA polynucleotides) comprise N6-methyl-adenosine (m6A) and 5-methyl-cytidine (m5C).

In some embodiments, polynucleotides (e.g., RNA polynucleotides, such as mRNA polynucleotides) are uniformly modified (e.g., fully modified, modified throughout the entire sequence) for a particular modification. For example, a polynucleotide can be uniformly modified with 5-methyl-cytidine (m5C), meaning that all cytosine residues in the mRNA sequence are replaced with 5-methyl-cytidine (m5C). Similarly, a polynucleotide can be uniformly modified for any type of nucleoside residue present in the sequence by replacement with a modified residue such as those set forth above.

Exemplary nucleobases and nucleosides having a modified cytosine include N4-acetyl-cytidine (ac4C), 5-methyl-cytidine (m5C), 5-halo-cytidine (e.g., 5-iodo-cytidine), 5-hydroxymethyl-cytidine (hm5C), 1-methyl-pseudoisocytidine, 2-thio-cytidine (s2C), and 2-thio-5-methyl-cytidine.

In some embodiments, a modified nucleobase is a modified uridine. Exemplary nucleobases and In some embodiments, a modified nucleobase is a modified cytosine. nucleosides having a modified uridine include 5-cyano uridine, and 4'-thio uridine.

The polynucleotides of the present disclosure may be partially or fully modified along the entire length of the molecule. For example, one or more or all or a given type of nucleotide (e.g., purine or pyrimidine, or any one or more or all of A, G, U, C) may be uniformly modified in a polynucleotide of the invention, or in a given predetermined sequence region thereof (e.g., in the mRNA including or excluding the polyA tail). In some embodiments, all nucleotides X in a polynucleotide of the present disclosure (or in a given sequence region thereof) are modified nucleotides, wherein X may any one of nucleotides A, G, U, C, or any one of the combinations A+G, A+U, A+C, G+U, G+C, U+C, A+G+U, A+G+C, G+U+C or A+G+C.

The polynucleotide may contain from about 1% to about 100% modified nucleotides (either in relation to overall nucleotide content, or in relation to one or more types of nucleotide, i.e., any one or more of A, G, U or C) or any intervening percentage (e.g., from 1% to 20%, from 1% to 25%, from 1% to 50%, from 1% to 60%, from 1% to 70%, from 1% to 80%, from 1% to 90%, from 1% to 95%, from 10% to 20%, from 10% to 25%, from 10% to 50%, from 10% to 60%, from 10% to 70%, from 10% to 80%, from 10% to 90%, from 10% to 95%, from 10% to 100%, from 20% to 25%, from 20% to 50%, from 20% to 60%, from 20% to 70%, from 20% to 80%, from 20% to 90%, from 20% to 95%, from 20% to 100%, from 50% to 60%, from 50% to 70%, from 50% to 80%, from 50% to 90%, from 50% to 95%, from 50% to 100%, from 70% to 80%, from 70% to 90%, from 70% to 95%, from 70% to 100%, from 80% to 90%, from 80% to 95%, from 80% to 100%, from 90% to 95%, from 90% to 100%, and from 95% to 100%). It will be understood that any remaining percentage is accounted for by the presence of unmodified A, G, U, or C.

The polynucleotides may contain at a minimum 1% and at maximum 100% modified nucleotides, or any intervening percentage, such as at least 5% modified nucleotides, at least 10% modified nucleotides, at least 25% modified nucleotides, at least 50% modified nucleotides, at least 80% modified nucleotides, or at least 90% modified nucleotides. For example, the polynucleotides may contain a modified pyrimidine such as a modified uracil or cytosine. In some embodiments, at least 5%, at least 10%, at least 25%, at least 50%, at least 80%, at least 90% or 100% of the uracil in the polynucleotide is replaced with a modified uracil (e.g., a 5-substituted uracil). The modified uracil can be replaced by a compound having a single unique structure, or can be replaced by a plurality of compounds having different structures (e.g., 2, 3, 4 or more unique structures). In some embodiments, at least 5%, at least 10%, at least 25%, at least 50%, at least 80%, at least 90% or 100% of the cytosine in the polynucleotide is replaced with a modified cytosine (e.g., a 5-substituted cytosine). The modified cytosine can be replaced by a compound having a single unique structure, or can be replaced by a plurality of compounds having different structures (e.g., 2, 3, 4 or more unique structures).

Untranslated Regions (UTRs)

The nucleic acids of the present disclosure may comprise one or more regions or parts which act or function as an untranslated region. Where nucleic acids are designed to encode at least one antigen of interest, the nucleic may comprise one or more of these untranslated regions (UTRs). Wild-type untranslated regions of a nucleic acid are transcribed but not translated. In mRNA, the 5' UTR starts at the transcription start site and continues to the start codon but does not include the start codon; whereas, the 3' UTR starts immediately following the stop codon and continues until the transcriptional termination signal. There is growing body of evidence about the regulatory roles played by the UTRs in terms of stability of the nucleic acid molecule and translation. The regulatory features of a UTR can be incorporated into the polynucleotides of the present disclosure to, among other things, enhance the stability of the molecule. The specific features can also be incorporated to ensure controlled down-regulation of the transcript in case they are misdirected to undesired organs sites. A variety of 5'UTR and 3'UTR sequences are known and available in the art.

A 5' UTR is region of an mRNA that is directly upstream (5') from the start codon (the first codon of an mRNA transcript translated by a ribosome). A 5' UTR does not encode a protein (is non-coding). Natural 5'UTRs have features that play roles in translation initiation. They harbor signatures like Kozak sequences which are commonly known to be involved in the process by which the ribosome initiates translation of many genes. Kozak sequences have the consensus CCR(A/G)CCAUGG (SEQ ID NO: 20), where R is a purine (adenine or guanine) three bases upstream of the start codon (AUG), which is followed by another 'G'. 5'UTR also have been known to form secondary structures which are involved in elongation factor binding.

In some embodiments of the disclosure, a 5' UTR is a heterologous UTR, i.e., is a UTR found in nature associated with a different ORF. In another embodiment, a 5' UTR is a synthetic UTR, i.e., does not occur in nature. Synthetic UTRs include UTRs that have been mutated to improve their properties, e.g., which increase gene expression as well as those which are completely synthetic. Exemplary 5' UTRs include *Xenopus* or human derived a-globin or b-globin (U.S. Pat. Nos. 8,278,063; 9,012,219), human cytochrome b-245 a polypeptide, and hydroxysteroid (17b) dehydrogenase, and Tobacco etch virus (U.S. Pat. Nos. 8,278,063; 9,012,219). CMV immediate-early 1 (IE1) gene (US20140206753, WO2013/185069), the sequence GGGAUCCUACC (SEQ ID NO: 21) (WO2014144196) may also be used. In another embodiment, 5' UTR of a TOP gene is a 5' UTR of a TOP gene lacking the 5' TOP motif (the oligopyrimidine tract) (e.g., WO/2015101414, WO2015101415, WO/2015/062738, WO2015024667, WO2015024667; 5' UTR element derived from ribosomal protein Large 32 (L32) gene (WO/2015101414, WO2015101415, WO/2015/062738), 5' UTR element derived from the 5'UTR of an hydroxysteroid (17-0) dehydrogenase 4 gene (HSD17B4) (WO2015024667), or a 5' UTR element derived from the 5' UTR of ATP5A1 (WO2015024667) can be used. In one embodiment, an internal ribosome entry site (IRES) is used instead of a 5' UTR.

In some embodiments, a 5' UTR of the present disclosure comprises a sequence selected from SEQ ID NO:10, SEQ ID NO:11, SEQ ID NO:14 and SEQ ID NO:15. In some embodiments, a 5' UTR of the present disclosure comprises a sequence selected from SEQ ID NO:10 and SEQ ID NO:11 and the ORF encodes H7N9. In some embodiments, a 5' UTR of the present disclosure comprises a sequence selected from SEQ ID NO:14 and SEQ ID NO:15 and the ORF encodes H10N8.

A 3' UTR is region of an mRNA that is directly downstream (3') from the stop codon (the codon of an mRNA transcript that signals a termination of translation). A 3' UTR does not encode a protein (is non-coding). Natural or wild type 3' UTRs are known to have stretches of adenosines and uridines embedded in them. These AU rich signatures are particularly prevalent in genes with high rates of turnover. Based on their sequence features and functional properties, the AU rich elements (AREs) can be separated into three classes (Chen et al, 1995): Class I AREs contain several dispersed copies of an AUUUA motif within U-rich regions. C-Myc and MyoD contain class I AREs. Class II AREs possess two or more overlapping UUAUUUA(U/A)(U/A) (SEQ ID NO: 22) nonamers. Molecules containing this type of AREs include GM-CSF and TNF-a. Class III ARES are less well defined. These U rich regions do not contain an AUUUA motif. c-Jun and Myogenin are two well-studied examples of this class. Most proteins binding to the AREs are known to destabilize the messenger, whereas members of the ELAV family, most notably HuR, have been documented to increase the stability of mRNA. HuR binds to AREs of all the three classes. Engineering the HuR specific binding sites into the 3' UTR of nucleic acid molecules will lead to HuR binding and thus, stabilization of the message in vivo.

Introduction, removal or modification of 3' UTR AU rich elements (AREs) can be used to modulate the stability of nucleic acids (e.g., RNA) of the disclosure. When engineering specific nucleic acids, one or more copies of an ARE can be introduced to make nucleic acids of the disclosure less stable and thereby curtail translation and decrease production of the resultant protein. Likewise, AREs can be identified and removed or mutated to increase the intracellular stability and thus increase translation and production of the resultant protein. Transfection experiments can be conducted in relevant cell lines, using nucleic acids of the disclosure and protein production can be assayed at various time points post-transfection. For example, cells can be transfected with different ARE-engineering molecules and by using an ELISA kit to the relevant protein and assaying protein produced at 6 hour, 12 hour, 24 hour, 48 hour, and 7 days post-transfection.

3' UTRs may be heterologous or synthetic. With respect to 3' UTRs, globin UTRs, including *Xenopus* β-globin UTRs and human β-globin UTRs are known in the art (U.S. Pat. Nos. 8,278,063, 9,012,219, US20110086907). A modified β-globin construct with enhanced stability in some cell types by cloning two sequential human β-globin 3'UTRs head to tail has been developed and is well known in the art (US2012/0195936, WO2014/071963). In addition a2-globin, al-globin, UTRs and mutants thereof are also known in the art (WO2015101415, WO2015024667). Other 3' UTRs described in the mRNA constructs in the non-patent literature include CYBA (Ferizi et al., 2015) and albumin (Thess et al., 2015). Other exemplary 3' UTRs include that of bovine or human growth hormone (wild type or modified) (WO2013/185069, US20140206753, WO2014152774), rabbit β globin and hepatitis B virus (HBV), α-globin 3' UTR and Viral VEEV 3' UTR sequences are also known in the art. In some embodiments, the sequence UUUGAAUU (WO2014144196) is used. In some embodiments, 3' UTRs of human and mouse ribosomal protein are used. Other examples include rps9 3'UTR (WO2015101414), FIG. 4 (WO2015101415), and human albumin 7 (WO2015101415).

In some embodiments, a 3' UTR of the present disclosure comprises a sequence selected from SEQ ID NO:12, SEQ ID NO:13, SEQ ID NO:16 and SEQ ID NO:17. In some embodiments, a 3' UTR of the present disclosure comprises a sequence selected from SEQ ID NO:12 and SEQ ID NO:11 and the ORF encodes H7N9. In some embodiments, a 3' UTR of the present disclosure comprises a sequence selected from SEQ ID NO:16 and SEQ ID NO:17 and the ORF encodes H10N8.

Those of ordinary skill in the art will understand that 5' UTRs that are heterologous or synthetic may be used with any desired 3' UTR sequence. For example, a heterologous 5' UTR may be used with a synthetic 3' UTR with a heterologous 3' UTR.

Non-UTR sequences may also be used as regions or subregions within a nucleic acid. For example, introns or portions of introns sequences may be incorporated into regions of nucleic acid of the disclosure. Incorporation of intronic sequences may increase protein production as well as nucleic acid levels.

Combinations of features may be included in flanking regions and may be contained within other features. For example, the ORF may be flanked by a 5' UTR which may contain a strong Kozak translational initiation signal and/or a 3' UTR which may include an oligo(dT) sequence for templated addition of a poly-A tail. 5' UTR may comprise a first polynucleotide fragment and a second polynucleotide fragment from the same and/or different genes such as the 5' UTRs described in US Patent Application Publication No. 20100293625 and PCT/US2014/069155, herein incorporated by reference in its entirety.

It should be understood that any UTR from any gene may be incorporated into the regions of a nucleic acid. Furthermore, multiple wild-type UTRs of any known gene may be utilized. It is also within the scope of the present disclosure to provide artificial UTRs which are not variants of wild type regions. These UTRs or portions thereof may be placed in the same orientation as in the transcript from which they were selected or may be altered in orientation or location. Hence a 5' or 3' UTR may be inverted, shortened, lengthened, made with one or more other 5' UTRs or 3' UTRs. As used herein, the term "altered" as it relates to a UTR sequence, means that the UTR has been changed in some way in relation to a reference sequence. For example, a 3' UTR or 5' UTR may be altered relative to a wild-type or native UTR by the change in orientation or location as taught above or may be altered by the inclusion of additional nucleotides, deletion of nucleotides, swapping or transposition of nucleotides. Any of these changes producing an "altered" UTR (whether 3' or 5') comprise a variant UTR.

In some embodiments, a double, triple or quadruple UTR such as a 5' UTR or 3' UTR may be used. As used herein, a "double" UTR is one in which two copies of the same UTR are encoded either in series or substantially in series. For example, a double beta-globin 3' UTR may be used as described in US Patent publication 20100129877, the contents of which are incorporated herein by reference in its entirety.

It is also within the scope of the present disclosure to have patterned UTRs. As used herein "patterned UTRs" are those UTRs which reflect a repeating or alternating pattern, such as ABABAB or AABBAABBAABB or ABCABCABC or variants thereof repeated once, twice, or more than 3 times. In these patterns, each letter, A, B, or C represent a different UTR at the nucleotide level.

In some embodiments, flanking regions are selected from a family of transcripts whose proteins share a common function, structure, feature or property. For example, polypeptides of interest may belong to a family of proteins which are expressed in a particular cell, tissue or at some time during development. The UTRs from any of these genes may be swapped for any other UTR of the same or different family of proteins to create a new polynucleotide. As used herein, a "family of proteins" is used in the broadest sense to refer to a group of two or more polypeptides of interest which share at least one function, structure, feature, localization, origin, or expression pattern.

The untranslated region may also include translation enhancer elements (TEE). As a non-limiting example, the TEE may include those described in US Application No. 20090226470, herein incorporated by reference in its entirety, and those known in the art.

In Vitro Transcription of RNA (e.g., mRNA)

Influenza vaccines of the present disclosure comprise at least one RNA polynucleotide, such as a mRNA (e.g., modified mRNA). mRNA, for example, is transcribed in vitro from template DNA, referred to as an "in vitro transcription template." In some embodiments, an in vitro transcription template encodes a 5' untranslated (UTR) region, contains an open reading frame, and encodes a 3' UTR and a polyA tail. The particular nucleic acid sequence composition and length of an in vitro transcription template will depend on the mRNA encoded by the template.

A "5' untranslated region" (UTR) refers to a region of an mRNA that is directly upstream (i.e., 5') from the start codon (i.e., the first codon of an mRNA transcript translated by a ribosome) that does not encode a polypeptide.

A "3' untranslated region" (UTR) refers to a region of an mRNA that is directly downstream (i.e., 3') from the stop codon (i.e., the codon of an mRNA transcript that signals a termination of translation) that does not encode a polypeptide.

An "open reading frame" is a continuous stretch of DNA beginning with a start codon (e.g., methionine (ATG)), and ending with a stop codon (e.g., TAA, TAG or TGA) and encodes a polypeptide.

A "polyA tail" is a region of mRNA that is downstream, e.g., directly downstream (i.e., 3'), from the 3' UTR that contains multiple, consecutive adenosine monophosphates. A polyA tail may contain 10 to 300 adenosine monophosphates. For example, a polyA tail may contain 10, 20, 30, 40, 50, 60, 70, 80, 90, 100, 110, 120, 130, 140, 150, 160, 170, 180, 190, 200, 210, 220, 230, 240, 250, 260, 270, 280, 290 or 300 adenosine monophosphates. In some embodiments, a polyA tail contains 50 to 250 adenosine monophosphates. In a relevant biological setting (e.g., in cells, in vivo) the poly(A) tail functions to protect mRNA from enzymatic degradation, e.g., in the cytoplasm, and aids in transcription termination, export of the mRNA from the nucleus and translation.

In some embodiments, a polynucleotide includes 200 to 3,000 nucleotides. For example, a polynucleotide may include 200 to 500, 200 to 1000, 200 to 1500, 200 to 3000, 500 to 1000, 500 to 1500, 500 to 2000, 500 to 3000, 1000 to 1500, 1000 to 2000, 1000 to 3000, 1500 to 3000, or 2000 to 3000 nucleotides).

Chemical Synthesis

Solid-phase chemical synthesis. Nucleic acids the present disclosure may be manufactured in whole or in part using solid phase techniques. Solid-phase chemical synthesis of nucleic acids is an automated method wherein molecules are immobilized on a solid support and synthesized step by step in a reactant solution. Solid-phase synthesis is useful in site-specific introduction of chemical modifications in the nucleic acid sequences.

Liquid Phase Chemical Synthesis. The synthesis of nucleic acids of the present disclosure by the sequential addition of monomer building blocks may be carried out in a liquid phase.

Combination of Synthetic Methods. The synthetic methods discussed above each has its own advantages and limitations. Attempts have been conducted to combine these methods to overcome the limitations. Such combinations of methods are within the scope of the present disclosure. The use of solid-phase or liquid-phase chemical synthesis in combination with enzymatic ligation provides an efficient way to generate long chain nucleic acids that cannot be obtained by chemical synthesis alone.

Ligation of Nucleic Acid Regions or Subregions

Assembling nucleic acids by a ligase may also be used. DNA or RNA ligases promote intermolecular ligation of the 5' and 3' ends of polynucleotide chains through the formation of a phosphodiester bond. Nucleic acids such as chimeric polynucleotides and/or circular nucleic acids may be prepared by ligation of one or more regions or subregions. DNA fragments can be joined by a ligase catalyzed reaction to create recombinant DNA with different functions. Two oligodeoxynucleotides, one with a 5' phosphoryl group and another with a free 3' hydroxyl group, serve as substrates for a DNA ligase.

Purification

Purification of the nucleic acids described herein may include, but is not limited to, nucleic acid clean-up, quality assurance and quality control. Clean-up may be performed by methods known in the arts such as, but not limited to, AGENCOURT® beads (Beckman Coulter Genomics, Danvers, MA), poly-T beads, LNA™ oligo-T capture probes (EXIQON® Inc, Vedbaek, Denmark) or HPLC based purification methods such as, but not limited to, strong anion exchange HPLC, weak anion exchange HPLC, reverse phase HPLC (RP-HPLC), and hydrophobic interaction HPLC (HIC-HPLC). The term "purified" when used in relation to a nucleic acid such as a "purified nucleic acid" refers to one that is separated from at least one contaminant. A "contaminant" is any substance that makes another unfit, impure or inferior. Thus, a purified nucleic acid (e.g., DNA and RNA) is present in a form or setting different from that in which it is found in nature, or a form or setting different from that which existed prior to subjecting it to a treatment or purification method.

A quality assurance and/or quality control check may be conducted using methods such as, but not limited to, gel electrophoresis, UV absorbance, or analytical HPLC.

In some embodiments, the nucleic acids may be sequenced by methods including, but not limited to reverse-transcriptase-PCR.

Quantification

In some embodiments, the nucleic acids of the present invention may be quantified in exosomes or when derived from one or more bodily fluid. Bodily fluids include peripheral blood, serum, plasma, ascites, urine, cerebrospinal fluid (CSF), sputum, saliva, bone marrow, synovial fluid, aqueous humor, amniotic fluid, cerumen, breast milk, broncheoalveolar lavage fluid, semen, prostatic fluid, cowper's fluid or pre-ejaculatory fluid, sweat, fecal matter, hair, tears, cyst fluid, pleural and peritoneal fluid, pericardial fluid, lymph, chyme, chyle, bile, interstitial fluid, menses, pus, sebum, vomit, vaginal secretions, mucosal secretion, stool water, pancreatic juice, lavage fluids from sinus cavities, bronchopulmonary aspirates, blastocyl cavity fluid, and umbilical cord blood. Alternatively, exosomes may be retrieved from an organ selected from the group consisting of lung, heart, pancreas, stomach, intestine, bladder, kidney, ovary, testis, skin, colon, breast, prostate, brain, esophagus, liver, and placenta.

Assays may be performed using construct specific probes, cytometry, qRT-PCR, real-time PCR, PCR, flow cytometry, electrophoresis, mass spectrometry, or combinations thereof while the exosomes may be isolated using immunohistochemical methods such as enzyme linked immunosorbent assay (ELISA) methods. Exosomes may also be isolated by size exclusion chromatography, density gradient centrifugation, differential centrifugation, nanomembrane ultrafiltration, immunoabsorbent capture, affinity purification, microfluidic separation, or combinations thereof.

These methods afford the investigator the ability to monitor, in real time, the level of nucleic acids remaining or delivered. This is possible because the nucleic acids of the present disclosure, in some embodiments, differ from the endogenous forms due to the structural or chemical modifications.

In some embodiments, the nucleic acid may be quantified using methods such as, but not limited to, ultraviolet visible spectroscopy (UV/Vis). A non-limiting example of a UV/Vis spectrometer is a NANODROP® spectrometer (ThermoFisher, Waltham, MA). The quantified nucleic acid may be analyzed in order to determine if the nucleic acid may be of proper size, check that no degradation of the nucleic acid has occurred. Degradation of the nucleic acid may be checked by methods such as, but not limited to, agarose gel electrophoresis, HPLC based purification methods such as, but not limited to, strong anion exchange HPLC, weak anion exchange HPLC, reverse phase HPLC (RP-HPLC), and hydrophobic interaction HPLC (HIC-HPLC), liquid chromatography-mass spectrometry (LCMS), capillary electrophoresis (CE) and capillary gel electrophoresis (CGE).

Methods of Treatment

Provided herein are compositions (e.g., pharmaceutical compositions), methods, kits and reagents for prevention and/or treatment of influenza in humans and other mammals. influenza RNA vaccines can be used as therapeutic or prophylactic agents. They may be used in medicine to prevent and/or treat infectious disease.

Broad Spectrum Vaccines

Influenza RNA (e.g., mRNA) vaccines can be used as therapeutic or prophylactic agents. It is envisioned that there may be situations where persons are at risk for infection with more than one betacoronovirus, for example, at risk for infection with influenza. RNA (e.g., mRNA) therapeutic vaccines are particularly amenable to combination vaccination approaches due to a number of factors including, but not limited to, speed of manufacture, ability to rapidly tailor vaccines to accommodate perceived geographical threat, and the like. Moreover, because the vaccines utilize the human body to produce the antigenic protein, the vaccines are amenable to the production of larger, more complex antigenic proteins, allowing for proper folding, surface expression, antigen presentation, etc. in the human subject. To protect against more than one influenza strain, a combination vaccine can be administered that includes RNA encoding at least one antigenic polypeptide of a first influenza and further includes RNA encoding at least one antigenic polypeptide of a second influenza. RNAs (mRNAs) can be co-formulated, for example, in a single LNP or can be formulated in separate LNPs destined for co-administration.

A method of eliciting an immune response in a subject against an influenza is provided in aspects of the invention. The method involves administering to the subject an influenza RNA vaccine comprising at least one RNA polynucleotide having an open reading frame encoding at least one influenza antigenic polypeptide or an immunogenic fragment thereof, thereby inducing in the subject an immune response specific to influenza antigenic polypeptide or an immunogenic fragment thereof, wherein anti-antigenic polypeptide antibody titer in the subject is increased following vaccination relative to anti-antigenic polypeptide antibody titer in a subject vaccinated with a prophylactically effective dose of a traditional vaccine against the influenza. An "anti-antigenic polypeptide antibody" is a serum antibody the binds specifically to the antigenic polypeptide.

A prophylactically effective dose is a therapeutically effective dose that prevents infection with the virus at a clinically acceptable level. In some embodiments the therapeutically effective dose is a dose listed in a package insert for the vaccine. A traditional vaccine, as used herein, refers to a vaccine other than the mRNA vaccines of the invention. For instance, a traditional vaccine includes but is not limited to live microorganism vaccines, killed microorganism vaccines, subunit vaccines, protein antigen vaccines, DNA vaccines, etc. In exemplary embodiments, a traditional vaccine is a vaccine that has achieved regulatory approval and/or is registered by a national drug regulatory body, for example the Food and Drug Administration (FDA) in the United States or the European Medicines Agency (EMA).

In some embodiments the anti-antigenic polypeptide antibody titer in the subject is increased 1 log to 10 log following vaccination relative to anti-antigenic polypeptide antibody titer in a subject vaccinated with a prophylactically effective dose of a traditional vaccine against the influenza.

In some embodiments the anti-antigenic polypeptide antibody titer in the subject is increased 1 log following vaccination relative to anti-antigenic polypeptide antibody titer in a subject vaccinated with a prophylactically effective dose of a traditional vaccine against the influenza.

In some embodiments the anti-antigenic polypeptide antibody titer in the subject is increased 2 log following vaccination relative to anti-antigenic polypeptide antibody titer in a subject vaccinated with a prophylactically effective dose of a traditional vaccine against the influenza.

In some embodiments the anti-antigenic polypeptide antibody titer in the subject is increased 3 log following vaccination relative to anti-antigenic polypeptide antibody titer in a subject vaccinated with a prophylactically effective dose of a traditional vaccine against the influenza.

In some embodiments the anti-antigenic polypeptide antibody titer in the subject is increased 5 log following vaccination relative to anti-antigenic polypeptide antibody titer in a subject vaccinated with a prophylactically effective dose of a traditional vaccine against the influenza.

In some embodiments the anti-antigenic polypeptide antibody titer in the subject is increased 10 log following vaccination relative to anti-antigenic polypeptide antibody titer in a subject vaccinated with a prophylactically effective dose of a traditional vaccine against the influenza.

A method of eliciting an immune response in a subject against an influenza is provided in other aspects of the invention. The method involves administering to the subject an influenza RNA vaccine comprising at least one RNA polynucleotide having an open reading frame encoding at least one influenza antigenic polypeptide or an immunogenic fragment thereof, thereby inducing in the subject an immune response specific to influenza antigenic polypeptide or an immunogenic fragment thereof, wherein the immune response in the subject is equivalent to an immune response in a subject vaccinated with a traditional vaccine against the influenza at 2 times to 100 times the dosage level relative to the RNA vaccine.

In some embodiments the immune response in the subject is equivalent to an immune response in a subject vaccinated with a traditional vaccine at twice the dosage level relative to the influenza RNA vaccine.

In some embodiments the immune response in the subject is equivalent to an immune response in a subject vaccinated with a traditional vaccine at three times the dosage level relative to the influenza RNA vaccine.

In some embodiments the immune response in the subject is equivalent to an immune response in a subject vaccinated with a traditional vaccine at 4 times the dosage level relative to the influenza RNA vaccine.

In some embodiments the immune response in the subject is equivalent to an immune response in a subject vaccinated with a traditional vaccine at 5 times the dosage level relative to the influenza RNA vaccine.

In some embodiments the immune response in the subject is equivalent to an immune response in a subject vaccinated with a traditional vaccine at 10 times the dosage level relative to the influenza RNA vaccine.

In some embodiments the immune response in the subject is equivalent to an immune response in a subject vaccinated with a traditional vaccine at 50 times the dosage level relative to the influenza RNA vaccine.

In some embodiments the immune response in the subject is equivalent to an immune response in a subject vaccinated with a traditional vaccine at 100 times the dosage level relative to the influenza RNA vaccine.

In some embodiments the immune response in the subject is equivalent to an immune response in a subject vaccinated with a traditional vaccine at 10 times to 1000 times the dosage level relative to the influenza RNA vaccine.

In some embodiments the immune response in the subject is equivalent to an immune response in a subject vaccinated with a traditional vaccine at 100 times to 1000 times the dosage level relative to the influenza RNA vaccine.

In other aspects the invention is a composition for or method of vaccinating a subject comprising administering to the subject a nucleic acid vaccine comprising one or more RNA polynucleotides having an open reading frame encoding a first antigenic polypeptide wherein a dosage of between 10 µg/kg and 400 µg/kg of the nucleic acid vaccine is administered to the subject. In some embodiments the dosage of the RNA polynucleotide is 1-5 µg, 5-10 µg, 10-15

μg, 15-20 μg, 10-25 μg, 20-25 μg, 20-50 μg, 30-50 μg, 40-50 μg, 40-60 μg, 60-80 μg, 60-100 μg, 50-100 μg, 80-120 μg, 40-120 μg, 40-150 μg, 50-150 μg, 50-200 μg, 80-200 μg, 100-200 μg, 120-250 μg, 150-250 μg, 180-280 μg, 200-300 μg, 50-300 μg, 80-300 μg, 100-300 μg, 40-300 μg, 50-350 μg, 100-350 μg, 200-350 μg, 300-350 μg, 320-400 μg, 40-380 μg, 40-100 μg, 100-400 μg, 200-400 μg, or 300-400 μg per dose. In some embodiments, the nucleic acid vaccine is administered to the subject by intradermal or intramuscular injection.

In some embodiments, the nucleic acid vaccine is administered to the subject on day zero. In some embodiments, a second dose of the nucleic acid vaccine is administered to the subject on day twenty one.

In other embodiments the immune response is assessed by determining anti-antigenic polypeptide antibody titer in the subject.

In other aspects the invention is a method of eliciting an immune response in a subject against an influenza by administering to the subject an influenza RNA vaccine comprising at least one RNA polynucleotide having an open reading frame encoding at least one influenza antigenic polypeptide or an immunogenic fragment thereof, thereby inducing in the subject an immune response specific to influenza antigenic polypeptide or an immunogenic fragment thereof, wherein the immune response in the subject is induced 2 days to 10 weeks earlier relative to an immune response induced in a subject vaccinated with a prophylactically effective dose of a traditional vaccine against the influenza. In some embodiments the immune response in the subject is induced in a subject vaccinated with a prophylactically effective dose of a traditional vaccine at 2 times to 100 times the dosage level relative to the RNA vaccine.

In some embodiments the immune response in the subject is induced 2 days earlier relative to an immune response induced in a subject vaccinated with a prophylactically effective dose of a traditional vaccine.

In some embodiments the immune response in the subject is induced 3 days earlier relative to an immune response induced in a subject vaccinated a prophylactically effective dose of a traditional vaccine.

In some embodiments the immune response in the subject is induced 1 week earlier relative to an immune response induced in a subject vaccinated with a prophylactically effective dose of a traditional vaccine.

In some embodiments the immune response in the subject is induced 2 weeks earlier relative to an immune response induced in a subject vaccinated with a prophylactically effective dose of a traditional vaccine.

In some embodiments the immune response in the subject is induced 3 weeks earlier relative to an immune response induced in a subject vaccinated with a prophylactically effective dose of a traditional vaccine.

In some embodiments the immune response in the subject is induced 5 weeks earlier relative to an immune response induced in a subject vaccinated with a prophylactically effective dose of a traditional vaccine.

In some embodiments the immune response in the subject is induced 10 weeks earlier relative to an immune response induced in a subject vaccinated with a prophylactically effective dose of a traditional vaccine.

A method of eliciting an immune response in a subject against an influenza by administering to the subject an influenza RNA vaccine having an open reading frame encoding a first antigenic polypeptide, wherein the RNA polynucleotide does not include a stabilization element, and wherein an adjuvant is not coformulated or co-administered with the vaccine is also provided herein.

Therapeutic and Prophylactic Compositions

Provided herein are compositions (e.g., pharmaceutical compositions), methods, kits and reagents for prevention, treatment or diagnosis of influenza in humans. Influenza RNA vaccines can be used as therapeutic or prophylactic agents. They may be used in medicine to prevent and/or treat infectious disease. In some embodiments, the influenza vaccines of the invention can be envisioned for use in the priming of immune effector cells, for example, to activate peripheral blood mononuclear cells (PBMCs) ex vivo, which are then infused (re-infused) into a subject.

In exemplary embodiments, an influenza vaccine containing RNA polynucleotides as described herein can be administered to a subject (e.g., a mammalian subject, such as a human subject), and the RNA polynucleotides are translated in vivo to produce an antigenic polypeptide. In some embodiments, the subject is a woman of child-bearing age. In some embodiments, vaccines described herein reduce or prevent congenital transmission of influenza from a mother to a child. (Pass et al. (2014) J Ped Infect Dis 3 (suppl 1): S2-S6.)

The influenza RNA vaccines may be induced for translation of a polypeptide (e.g., antigen or immunogen) in a cell, tissue or organism. In exemplary embodiments, such translation occurs in vivo, although there can be envisioned embodiments where such translation occurs ex vivo, in culture or in vitro. In exemplary embodiments, the cell, tissue or organism is contacted with an effective amount of a composition containing an influenza RNA vaccine that contains a polynucleotide that has at least one a translatable region encoding an antigenic polypeptide.

An "effective amount" of the influenza RNA vaccine is provided based, at least in part, on the target tissue, target cell type, means of administration, physical characteristics of the polynucleotide (e.g., size, and extent of modified nucleosides) and other components of the influenza RNA vaccine, and other determinants. In general, an effective amount of the influenza RNA vaccine composition provides an induced or boosted immune response as a function of antigen production in the cell, preferably more efficient than a composition containing a corresponding unmodified polynucleotide encoding the same antigen or a peptide antigen. Increased antigen production may be demonstrated by increased cell transfection (the percentage of cells transfected with the RNA vaccine), increased protein translation from the polynucleotide, decreased nucleic acid degradation (as demonstrated, for example, by increased duration of protein translation from a modified polynucleotide), or altered antigen specific immune response of the host cell.

In some embodiments, RNA vaccines (including polynucleotides their encoded polypeptides) in accordance with the present disclosure may be used for treatment of influenza.

Influenza RNA vaccines may be administered prophylactically or therapeutically as part of an active immunization scheme to healthy individuals or early in infection during the incubation phase or during active infection after onset of symptoms. In some embodiments, the amount of RNA vaccines of the present disclosure provided to a cell, a tissue or a subject may be an amount effective for immune prophylaxis.

Influenza RNA vaccines may be administrated with other prophylactic or therapeutic compounds. As a non-limiting example, a prophylactic or therapeutic compound may be an adjuvant or a booster. As used herein, when referring to a prophylactic composition, such as a vaccine, the term "booster" refers to an extra administration of the prophylactic (vaccine) composition. A booster (or booster vaccine) may be given after an earlier administration of the prophylactic composition. The time of administration between the initial administration of the prophylactic composition and the booster may be, but is not limited to, 1 minute, 2 minutes, 3 minutes, 4 minutes, 5 minutes, 6 minutes, 7 minutes, 8 minutes, 9 minutes, 10 minutes, 15 minutes, 20 minutes 35 minutes, 40 minutes, 45 minutes, 50 minutes, 55 minutes, 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 1 day, 36 hours, 2 days, 3 days, 4 days, 5 days, 6 days, 1 week, 10 days, 2 weeks, 3 weeks, 1 month, 2 months, 3 months, 4 months, 5 months, 6 months, 7 months, 8 months, 9 months, 10 months, 11 months, 1 year, 18 months, 2 years, 3 years, 4 years, 5 years, 6 years, 7 years, 8 years, 9 years, 10 years, 11 years, 12 years, 13 years, 14 years, 15 years, 16 years, 17 years, 18 years, 19 years, 20 years, 25 years, 30 years, 35 years, 40 years, 45 years, 50 years, 55 years, 60 years, 65 years, 70 years, 75 years, 80 years, 85 years, 90 years, 95 years or more than 99 years. In exemplary embodiments, the time of administration between the initial administration of the prophylactic composition and the booster may be, but is not limited to, 1 week, 2 weeks, 3 weeks, 1 month, 2 months, 3 months, 6 months or 1 year.

In some embodiments, influenza RNA vaccines may be administered intramuscularly or intradermally, similarly to the administration of inactivated vaccines known in the art.

The influenza RNA vaccines may be utilized in various settings depending on the prevalence of the infection or the degree or level of unmet medical need. As a non-limiting example, the RNA vaccines may be utilized to treat and/or prevent a variety of infectious disease. RNA vaccines have superior properties in that they produce much larger antibody titers and produce responses early than commercially available anti-virals.

Provided herein are pharmaceutical compositions including influenza RNA vaccines and RNA vaccine compositions and/or complexes optionally in combination with one or more pharmaceutically acceptable excipients.

Influenza RNA vaccines may be formulated or administered alone or in conjunction with one or more other components. For instance, influenza RNA vaccines (vaccine compositions) may comprise other components including, but not limited to, adjuvants. In some embodiments, influenza RNA vaccines do not include an adjuvant (they are adjuvant free).

Influenza RNA vaccines may be formulated or administered in combination with one or more pharmaceutically-acceptable excipients. In some embodiments, vaccine compositions comprise at least one additional active substances, such as, for example, a therapeutically-active substance, a prophylactically-active substance, or a combination of both. Vaccine compositions may be sterile, pyrogen-free or both sterile and pyrogen-free. General considerations in the formulation and/or manufacture of pharmaceutical agents, such as vaccine compositions, may be found, for example, in Remington: The Science and Practice of Pharmacy 21st ed., Lippincott Williams & Wilkins, 2005 (incorporated herein by reference in its entirety).

In some embodiments, influenza RNA vaccines are administered to humans, human patients or subjects. For the purposes of the present disclosure, the phrase "active ingredient" generally refers to the RNA vaccines or the polynucleotides contained therein, for example, RNA polynucleotides (e.g., mRNA polynucleotides) encoding antigenic polypeptides.

Formulations of the vaccine compositions described herein may be prepared by any method known or hereafter developed in the art of pharmacology. In general, such preparatory methods include the step of bringing the active ingredient (e.g., mRNA polynucleotide) into association with an excipient and/or one or more other accessory ingredients, and then, if necessary and/or desirable, dividing, shaping and/or packaging the product into a desired single- or multi-dose unit.

Relative amounts of the active ingredient, the pharmaceutically acceptable excipient, and/or any additional ingredients in a pharmaceutical composition in accordance with the disclosure will vary, depending upon the identity, size, and/or condition of the subject treated and further depending upon the route by which the composition is to be administered. By way of example, the composition may comprise between 0.1% and 100%, e.g., between 0.5 and 50%, between 1-30%, between 5-80%, at least 80% (w/w) active ingredient.

Influenza RNA vaccines can be formulated using one or more excipients to: (1) increase stability; (2) increase cell transfection; (3) permit the sustained or delayed release (e.g., from a depot formulation); (4) alter the biodistribution (e.g., target to specific tissues or cell types); (5) increase the translation of encoded protein in vivo; and/or (6) alter the release profile of encoded protein (antigen) in vivo. In addition to traditional excipients such as any and all solvents, dispersion media, diluents, or other liquid vehicles, dispersion or suspension aids, surface active agents, isotonic agents, thickening or emulsifying agents, preservatives, excipients can include, without limitation, lipidoids, liposomes, lipid nanoparticles, polymers, lipoplexes, core-shell nanoparticles, peptides, proteins, cells transfected with influenza RNA vaccines (e.g., for transplantation into a subject), hyaluronidase, nanoparticle mimics and combinations thereof.

Stabilizing Elements

Naturally-occurring eukaryotic mRNA molecules have been found to contain stabilizing elements, including, but not limited to untranslated regions (UTR) at their 5'-end (5'UTR) and/or at their 3'-end (3'UTR), in addition to other structural features, such as a 5'-cap structure or a 3'-poly(A) tail. Both the 5'UTR and the 3'UTR are typically transcribed from the genomic DNA and are elements of the premature mRNA. Characteristic structural features of mature mRNA, such as the 5'-cap and the 3'-poly(A) tail are usually added to the transcribed (premature) mRNA during mRNA processing. The 3'-poly(A) tail is typically a stretch of adenine nucleotides added to the 3'-end of the transcribed mRNA. It can comprise up to about 400 adenine nucleotides. In some embodiments the length of the 3'-poly(A) tail may be an essential element with respect to the stability of the individual mRNA.

In some embodiments the RNA vaccine may include one or more stabilizing elements. Stabilizing elements may include for instance a histone stem-loop. A stem-loop binding protein (SLBP), a 32 kDa protein has been identified. It is associated with the histone stem-loop at the 3'-end of the histone messages in both the nucleus and the cytoplasm. Its expression level is regulated by the cell cycle; it is peaks during the S-phase, when histone mRNA levels are also elevated. The protein has been shown to be essential for efficient 3'-end processing of histone pre-mRNA by the U7 snRNP. SLBP continues to be associated with the stem-loop after processing, and then stimulates the translation of mature histone mRNAs into histone proteins in the cytoplasm. The RNA binding domain of SLBP is conserved through metazoa and protozoa; its binding to the histone stem-loop depends on the structure of the loop. The minimum binding site includes at least three nucleotides 5' and two nucleotides 3' relative to the stem-loop.

In some embodiments, the RNA vaccines include a coding region, at least one histone stem-loop, and optionally, a poly(A) sequence or polyadenylation signal. The poly(A) sequence or polyadenylation signal generally should enhance the expression level of the encoded protein. The encoded protein, in some embodiments, is not a histone protein, a reporter protein (e.g. Luciferase, GFP, EGFP, β-Galactosidase, EGFP), or a marker or selection protein (e.g. alpha-Globin, Galactokinase and Xanthine:guanine phosphoribosyl transferase (GPT)).

In some embodiments, the combination of a poly(A) sequence or polyadenylation signal and at least one histone stem-loop, even though both represent alternative mechanisms in nature, acts synergistically to increase the protein expression beyond the level observed with either of the individual elements. It has been found that the synergistic effect of the combination of poly(A) and at least one histone stem-loop does not depend on the order of the elements or the length of the poly(A) sequence.

In some embodiments, the RNA vaccine does not comprise a histone downstream element (HDE). "Histone downstream element" (HDE) includes a purine-rich polynucleotide stretch of approximately 15 to 20 nucleotides 3' of naturally occurring stem-loops, representing the binding site for the U7 snRNA, which is involved in processing of histone pre-mRNA into mature histone mRNA. Ideally, the inventive nucleic acid does not include an intron.

In some embodiments, the RNA vaccine may or may not contain a enhancer and/or promoter sequence, which may be modified or unmodified or which may be activated or inactivated. In some embodiments, the histone stem-loop is generally derived from histone genes, and includes an intramolecular base pairing of two neighbored partially or entirely reverse complementary sequences separated by a spacer, consisting of a short sequence, which forms the loop of the structure. The unpaired loop region is typically unable to base pair with either of the stem loop elements. It occurs more often in RNA, as is a key component of many RNA secondary structures, but may be present in single-stranded DNA as well. Stability of the stem-loop structure generally depends on the length, number of mismatches or bulges, and base composition of the paired region. In some embodiments, wobble base pairing (non-Watson-Crick base pairing) may result. In some embodiments, the at least one histone stem-loop sequence comprises a length of 15 to 45 nucleotides.

In other embodiments the RNA vaccine may have one or more AU-rich sequences removed. These sequences, sometimes referred to as AURES are destabilizing sequences found in the 3'UTR. The AURES may be removed from the RNA vaccines. Alternatively the AURES may remain in the RNA vaccine.

Nanoparticle Formulations

In some embodiments, influenza RNA vaccines are formulated in a nanoparticle. In some embodiments, influenza RNA vaccines are formulated in a lipid nanoparticle. In some embodiments, influenza RNA vaccines are formulated in a lipid-polycation complex, referred to as a cationic lipid nanoparticle. The formation of the lipid nanoparticle may be accomplished by methods known in the art and/or as described in U.S. Pub. No. 20120178702, herein incorporated by reference in its entirety. As a non-limiting example, the polycation may include a cationic peptide or a polypeptide such as, but not limited to, polylysine, polyornithine and/or polyarginine and the cationic peptides described in International Pub. No. WO2012013326 or US Patent Pub. No. US20130142818; each of which is herein incorporated by reference in its entirety. In some embodiments, influenza RNA vaccines are formulated in a lipid nanoparticle that includes a non-cationic lipid such as, but not limited to, cholesterol or dioleoyl phosphatidylethanolamine (DOPE).

A lipid nanoparticle formulation may be influenced by, but not limited to, the selection of the cationic lipid component, the degree of cationic lipid saturation, the nature of the PEGylation, ratio of all components and biophysical parameters such as size. In one example by Semple et al. (Nature Biotech. 2010 28:172-176; herein incorporated by reference in its entirety), the lipid nanoparticle formulation is composed of 57.1% cationic lipid, 7.1% dipalmitoylphosphatidylcholine, 34.3% cholesterol, and 1.4% PEG-c-DMA. As another example, changing the composition of the cationic lipid can more effectively deliver siRNA to various antigen presenting cells (Basha et al. Mol Ther. 2011 19:2186-2200; herein incorporated by reference in its entirety).

In some embodiments, lipid nanoparticle formulations may comprise 35 to 45% cationic lipid, 40% to 50% cationic lipid, 50% to 60% cationic lipid and/or 55% to 65% cationic lipid. In some embodiments, the ratio of lipid to RNA (e.g., mRNA) in lipid nanoparticles may be 5:1 to 20:1, 10:1 to 25:1, 15:1 to 30:1 and/or at least 30:1.

In some embodiments, the ratio of PEG in the lipid nanoparticle formulations may be increased or decreased and/or the carbon chain length of the PEG lipid may be modified from C14 to C18 to alter the pharmacokinetics and/or biodistribution of the lipid nanoparticle formulations. As a non-limiting example, lipid nanoparticle formulations may contain 0.5% 30 to 3.0%, 1.0% to 3.5%, 1.5% to 4.0%, 2.0% to 4.5%, 2.5% to 5.0% and/or 3.0% to 6.0% of the lipid molar ratio of PEG-c-DOMG (R-3-[(ω-methoxy-poly(ethyleneglycol)2000)carbamoyl)]-1,2-dimyristyloxypropyl-3-amine) (also referred to herein as PEG-DOMG) as compared to the cationic lipid, DSPC and cholesterol. In some embodiments, the PEG-c-DOMG may be replaced with a PEG lipid such as, but not limited to, PEG-DSG (1,2-Distearoyl-sn-glycerol, methoxypolyethylene glycol), PEG-DMG (1,2-Dimyristoyl-sn-glycerol) and/or PEG-DPG (1,2-Dipalmitoyl-sn-glycerol, methoxypolyethylene glycol). The cationic lipid may be selected from any lipid known in the art such as, but not limited to, DLin-MC3-DMA, DLin-DMA, C12-200 and DLin-KC2-DMA.

In some embodiments, an influenza RNA vaccine formulation is a nanoparticle that comprises at least one lipid. The lipid may be selected from, but is not limited to, DLin-DMA, DLin-K-DMA, 98N12-5, C12-200, DLin-MC3-DMA, DLin-KC2-DMA, DODMA, PLGA, PEG, PEG-DMG, PEGylated lipids and amino alcohol lipids. In some embodiments, the lipid may be a cationic lipid such as, but not limited to, DLin-DMA, DLin-D-DMA, DLin-MC3-DMA, DLin-KC2-DMA, DODMA and amino alcohol lipids. The amino alcohol cationic lipid may be the lipids described in and/or made by the methods described in US Patent Publication No. US20130150625, herein incorporated by reference in its entirety. As a non-limiting example, the cationic lipid may be 2-amino-3-[(9Z,12Z)-octadeca-9,12-dien-1-yloxy]-2-{[(9Z,2Z)-octadeca-9,12-dien-1-yloxy]methyl}propan-1-ol (Compound 1 in US20130150625);

2-amino-3-[(9Z)-octadec-9-en-1-yloxy]-2-{[(9Z)-octadec-9-en-1-yloxy]methyl}propan-1-ol (Compound 2 in US20130150625); 2-amino-3-[(9Z,12Z)-octadeca-9,12-dien-1-yloxy]-2-[(octyloxy)methyl]propan-1-ol (Compound 3 in US20130150625); and 2-(dimethylamino)-3-[(9Z,12Z)-octadeca-9,12-dien-1-yloxy]-2-{[(9Z,12Z)-octadeca-9,12-dien-1-yloxy]methyl}propan-1-ol (Compound 4 in US20130150625); or any pharmaceutically acceptable salt or stereoisomer thereof.

Lipid nanoparticle formulations typically comprise a lipid, in particular, an ionizable cationic lipid, for example, 2,2-dilinoleyl-4-dimethylaminoethyl-[1,3]-dioxolane (DLin-KC2-DMA), dilinoleyl-methyl-4-dimethylaminobutyrate (DLin-MC3-DMA), or di((Z)-non-2-en-1-yl) 9-((4-(dimethylamino)butanoyl)oxy)heptadecanedioate (L319), and further comprise a neutral lipid, a sterol and a molecule capable of reducing particle aggregation, for example a PEG or PEG-modified lipid.

In some embodiments, a lipid nanoparticle formulation consists essentially of (i) at least one lipid selected from the group consisting of 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319); (ii) a neutral lipid selected from DSPC, DPPC, POPC, DOPE and SM; (iii) a sterol, e.g., cholesterol; and (iv) a PEG-lipid, e.g., PEG-DMG or PEG-cDMA, in a molar ratio of 20-60% cationic lipid:5-25% neutral lipid:25-55% sterol:0.5-15% PEG-lipid.

In some embodiments, a lipid nanoparticle formulation includes 25% to 75% on a molar basis of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), e.g., 35 to 65%, 45 to 65%, 60%, 57.5%, 50% or 40% on a molar basis.

In some embodiments, a lipid nanoparticle formulation includes 0.5% to 15% on a molar basis of the neutral lipid, e.g., 3 to 12%, 5 to 10% or 15%, 10%, or 7.5% on a molar basis. Examples of neutral lipids include, without limitation, DSPC, POPC, DPPC, DOPE and SM. In some embodiments, the formulation includes 5% to 50% on a molar basis of the sterol (e.g., 15 to 45%, 20 to 40%, 40%, 38.5%, 35%, or 31% on a molar basis. A non-limiting example of a sterol is cholesterol. In some embodiments, a lipid nanoparticle formulation includes 0.5% to 20% on a molar basis of the PEG or PEG-modified lipid (e.g., 0.5 to 10%, 0.5 to 5%, 1.5%, 0.5%, 1.5%, 3.5%, or 5% on a molar basis. In some embodiments, a PEG or PEG modified lipid comprises a PEG molecule of an average molecular weight of 2,000 Da. In some embodiments, a PEG or PEG modified lipid comprises a PEG molecule of an average molecular weight of less than 2,000, for example around 1,500 Da, around 1,000 Da, or around 500 Da. Non-limiting examples of PEG-modified lipids include PEG-distearoyl glycerol (PEG-DMG) (also referred herein as PEG-C14 or C14-PEG), PEG-cDMA (further discussed in Reyes et al. J. Controlled Release, 107, 276-287 (2005) the contents of which are herein incorporated by reference in its entirety).

In some embodiments, lipid nanoparticle formulations include 25-75% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), 0.5-15% of the neutral lipid, 5-50% of the sterol, and 0.5-20% of the PEG or PEG-modified lipid on a molar basis.

In some embodiments, lipid nanoparticle formulations include 35-65% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), 3-12% of the neutral lipid, 15-45% of the sterol, and 0.5-10% of the PEG or PEG-modified lipid on a molar basis.

In some embodiments, lipid nanoparticle formulations include 45-65% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), 5-10% of the neutral lipid, 25-40% of the sterol, and 0.5-10% of the PEG or PEG-modified lipid on a molar basis.

In some embodiments, lipid nanoparticle formulations include 60% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), 7.5% of the neutral lipid, 31% of the sterol, and 1.5% of the PEG or PEG-modified lipid on a molar basis.

In some embodiments, lipid nanoparticle formulations include 50% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), 10% of the neutral lipid, 38.5% of the sterol, and 1.5% of the PEG or PEG-modified lipid on a molar basis.

In some embodiments, lipid nanoparticle formulations include 50% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), 10% of the neutral lipid, 35% of the sterol, 4.5% or 5% of the PEG or PEG-modified lipid, and 0.5% of the targeting lipid on a molar basis.

In some embodiments, lipid nanoparticle formulations include 40% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), 15% of the neutral lipid, 40% of the sterol, and 5% of the PEG or PEG-modified lipid on a molar basis.

In some embodiments, lipid nanoparticle formulations include 57.2% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), 7.1% of the neutral lipid, 34.3% of the sterol, and 1.4% of the PEG or PEG-modified lipid on a molar basis.

In some embodiments, lipid nanoparticle formulations include 57.5% of a cationic lipid selected from the PEG lipid is PEG-cDMA (PEG-cDMA is further discussed in Reyes et al. (J. Controlled Release, 107, 276-287 (2005), the contents of which are herein incorporated by reference in its entirety), 7.5% of the neutral lipid, 31.5% of the sterol, and 3.5% of the PEG or PEG-modified lipid on a molar basis.

In some embodiments, lipid nanoparticle formulations consists essentially of a lipid mixture in molar ratios of 20-70% cationic lipid:5-45% neutral lipid:20-55% cholesterol:0.5-15% PEG-modified lipid. In some embodiments, lipid nanoparticle formulations consists essentially of a lipid mixture in a molar ratio of 20-60% cationic lipid:5-25% neutral lipid:25-55% cholesterol:0.5-15% PEG-modified lipid.

In some embodiments, the molar lipid ratio is 50/10/38.5/1.5 (mol % cationic lipid/neutral lipid, e.g., DSPC/Chol/PEG-modified lipid, e.g., PEG-DMG, PEG-DSG or PEG-DPG), 57.2/7.1134.3/1.4 (mol % cationic lipid/neutral lipid, e.g., DPPC/Chol/PEG-modified lipid, e.g., PEG-cDMA), 40/15/40/5 (mol % cationic lipid/neutral lipid, e.g., DSPC/Chol/PEG-modified lipid, e.g., PEG-DMG), 50/10/35/4.5/0.5 (mol % cationic lipid/neutral lipid, e.g., DSPC/Chol/PEG-modified lipid, e.g., PEG-DSG), 50/10/35/5 (cationic lipid/neutral lipid, e.g., DSPC/Chol/PEG-modified lipid, e.g., PEG-DMG), 40/10/40/10 (mol % cationic lipid/neutral lipid, e.g., DSPC/Chol/PEG-modified lipid, e.g., PEG-DMG or PEG-cDMA), 35/15/40/10 (mol % cationic lipid/neutral lipid, e.g., DSPC/Chol/PEG-modified lipid, e.g., PEG-DMG or PEG-cDMA) or 52/13/30/5 (mol % cationic lipid/neutral lipid, e.g., DSPC/Chol/PEG-modified lipid, e.g., PEG-DMG or PEG-cDMA).

Non-limiting examples of lipid nanoparticle compositions and methods of making them are described, for example, in Semple et al. (2010) Nat. Biotechnol. 28:172-176; Jayarama et al. (2012), Angew. Chem. Int. Ed., 51: 8529-8533; and Maier et al. (2013) Molecular Therapy 21, 1570-1578 (the contents of each of which are incorporated herein by reference in their entirety).

In some embodiments, lipid nanoparticle formulations may comprise a cationic lipid, a PEG lipid and a structural lipid and optionally comprise a non-cationic lipid. As a non-limiting example, a lipid nanoparticle may comprise 40-60% of cationic lipid, 5-15% of a non-cationic lipid, 1-2% of a PEG lipid and 30-50% of a structural lipid. As another non-limiting example, the lipid nanoparticle may comprise 50% cationic lipid, 10% non-cationic lipid, 1.5% PEG lipid and 38.5% structural lipid. As yet another non-limiting example, a lipid nanoparticle may comprise 55% cationic lipid, 10% non-cationic lipid, 2.5% PEG lipid and 32.5% structural lipid. In some embodiments, the cationic lipid may be any cationic lipid described herein such as, but not limited to, DLin-KC2-DMA, DLin-MC3-DMA and L319.

In some embodiments, the lipid nanoparticle formulations described herein may be 4 component lipid nanoparticles. The lipid nanoparticle may comprise a cationic lipid, a non-cationic lipid, a PEG lipid and a structural lipid. As a non-limiting example, the lipid nanoparticle may comprise 40-60% of cationic lipid, 5-15% of a non-cationic lipid, 1-2% of a PEG lipid and 30-50% of a structural lipid. As another non-limiting example, the lipid nanoparticle may comprise 50% cationic lipid, 10% non-cationic lipid, 1.5% PEG lipid and 38.5% structural lipid. As yet another non-limiting example, the lipid nanoparticle may comprise 55% cationic lipid, 10% non-cationic lipid, 2.5% PEG lipid and 32.5% structural lipid. In some embodiments, the cationic lipid may be any cationic lipid described herein such as, but not limited to, DLin-KC2-DMA, DLin-MC3-DMA and L319.

In some embodiments, the lipid nanoparticle formulations described herein may comprise a cationic lipid, a non-cationic lipid, a PEG lipid and a structural lipid. As a non-limiting example, the lipid nanoparticle comprise 50% of the cationic lipid DLin-KC2-DMA, 10% of the non-cationic lipid DSPC, 1.5% of the PEG lipid PEG-DOMG and 38.5% of the structural lipid cholesterol. As a non-limiting example, the lipid nanoparticle comprise 50% of the cationic lipid DLin-MC3-DMA, 10% of the non-cationic lipid DSPC, 1.5% of the PEG lipid PEG-DOMG and 38.5% of the structural lipid cholesterol. As a non-limiting example, the lipid nanoparticle comprise 50% of the cationic lipid DLin-MC3-DMA, 10% of the non-cationic lipid DSPC, 1.5% of the PEG lipid PEG-DMG and 38.5% of the structural lipid cholesterol. As yet another non-limiting example, the lipid nanoparticle comprise 55% of the cationic lipid L319, 10% of the non-cationic lipid DSPC, 2.5% of the PEG lipid PEG-DMG and 32.5% of the structural lipid cholesterol.

In some embodiments, a nanoparticle comprises compounds of Formula (I):

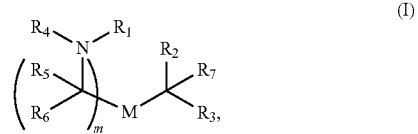

or a salt or isomer thereof, wherein:

$R_1$ is selected from the group consisting of C5-30 alkyl, C5-20 alkenyl, —R*YR", —YR", and —R"M'R';

$R_2$ and $R_3$ are independently selected from the group consisting of H, C1-14 alkyl, C2-14 alkenyl, —R*YR", —YR", and —R*OR", or $R_2$ and $R_3$, together with the atom to which they are attached, form a heterocycle or carbocycle;

$R_4$ is selected from the group consisting of a C3-6 carbocycle, —(CH2)nQ, —(CH2)nCHQR, —CHQR, —CQ(R)2, and unsubstituted C1-6 alkyl, where Q is selected from a carbocycle, heterocycle, —OR, —O(CH2)nN(R)2, —C(O)OR, —OC(O)R, —CX3, —CX2H, —CXH2, —CN, —N(R)2, —C(O)N(R)2, —N(R)C(O)R, —N(R)S(O)2R, —N(R)C(O)N(R)2, —N(R)C(S)N(R)2, —N(R)R8, —O(CH2)nOR, —N(R)C(=NR9)N(R)2, —N(R)C(=CHR9)N(R)2, —OC(O)N(R)2, —N(R)C(O)OR, —N(OR)C(O)R, —N(OR)S(O)2R, —N(OR)C(O)OR, —N(OR)C(O)N(R)2, —N(OR)C(S)N(R)2, —N(OR)C(=NR9)N(R)2, —N(OR)C(=CHR9)N(R)2, —C(=NR9)N(R)2, —C(=NR9)R, —C(O)N(R)OR, and —C(R)N(R)2C(O)OR, and each n is independently selected from 1, 2, 3, 4, and 5;

each $R_5$ is independently selected from the group consisting of C1-3 alkyl, C2-3 alkenyl, and H;

each $R_6$ is independently selected from the group consisting of C1-3 alkyl, C2-3 alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)2-, —S—S—, an aryl group, and a heteroaryl group;

$R_7$ is selected from the group consisting of C1-3 alkyl, C2-3 alkenyl, and H;

$R_8$ is selected from the group consisting of C3-6 carbocycle and heterocycle;

$R_9$ is selected from the group consisting of H, CN, NO2, C1-6 alkyl, —OR, —S(O)2R, —S(O)2N(R)2, C2-6 alkenyl, C3-6 carbocycle and heterocycle;

each R is independently selected from the group consisting of C1-3 alkyl, C2-3 alkenyl, and H;

each R' is independently selected from the group consisting of C1-18 alkyl, C2-18 alkenyl, —R*YR", —YR", and H;

each R" is independently selected from the group consisting of C3-14 alkyl and C3-14 alkenyl;

each R* is independently selected from the group consisting of C1-12 alkyl and C2-12 alkenyl;

each Y is independently a C3-6 carbocycle;

each X is independently selected from the group consisting of F, Cl, Br, and I; and m is selected from 5, 6, 7, 8, 9, 10, 11, 12, and 13.

In some embodiments, a subset of compounds of Formula (I) includes those in which when R4 is —(CH2)nQ, —(CH2)nCHQR, —CHQR, or —CQ(R)2, then (i) Q is not —N(R)2 when n is 1, 2, 3, 4 or 5, or (ii) Q is not 5, 6, or 7-membered heterocycloalkyl when n is 1 or 2.

In some embodiments, another subset of compounds of Formula (I) includes those in which R1 is selected from the group consisting of C5-30 alkyl, C5-20 alkenyl, —R*YR", —YR", and —R"M'R';

R2 and R3 are independently selected from the group consisting of H, C1-14 alkyl, C2-14 alkenyl, —R*YR", —YR", and —R*OR", or R2 and R3, together with the atom to which they are attached, form a heterocycle or carbocycle;

R4 is selected from the group consisting of a C3-6 carbocycle, —(CH2)nQ, —(CH2)nCHQR, —CHQR, —CQ(R)2, and unsubstituted C1-6 alkyl, where Q is selected from a C3-6 carbocycle, a 5- to 14-membered heteroaryl having one or more heteroatoms selected from N, O, and S, —OR, —O(CH2)nN(R)2, —C(O)OR, —OC(O)R, —CX3, —CX2H, —CXH2, —CN, —C(O)N(R)2, —N(R)C(O)R, —N(R)S(O)2R, —N(R)C(O)N(R)2, —N(R)C(S)N(R)2, —CRN(R)2C(O)OR, —N(R)R8, —O(CH2)nOR, —N(R)C(=NR9)N(R)2, —N(R)C(=CHR9)N(R)2, —OC(O)N(R)2, —N(R)C(O)OR, —N(OR)C(O)R, —N(OR)S(O)2R, —N(OR)C(O)OR, —N(OR)C(O)N(R)2, —N(OR)C(S)N(R)2, —N(OR)C(=NR9)N(R)2, —N(OR)C(=CHR9)N(R)2, —C(=NR9)N(R)2, —C(=NR9)R, —C(O)N(R)OR, and a 5- to 14-membered heterocycloalkyl having one or more heteroatoms selected from N, O, and S which is substituted with one or more substituents selected from oxo (=O), OH, amino, mono- or di-alkylamino, and C1-3 alkyl, and each n is independently selected from 1, 2, 3, 4, and 5;

each R5 is independently selected from the group consisting of C1-3 alkyl, C2-3 alkenyl, and H;

each R6 is independently selected from the group consisting of C1-3 alkyl, C2-3 alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)2-, —S—S—, an aryl group, and a heteroaryl group;

R7 is selected from the group consisting of C1-3 alkyl, C2-3 alkenyl, and H;

R8 is selected from the group consisting of C3-6 carbocycle and heterocycle;

R9 is selected from the group consisting of H, CN, NO2, C1-6 alkyl, —OR, —S(O)2R, —S(O)2N(R)2, C2-6 alkenyl, C3-6 carbocycle and heterocycle;

each R is independently selected from the group consisting of C1-3 alkyl, C2-3 alkenyl, and H;

each R' is independently selected from the group consisting of C1-18 alkyl, C2-18 alkenyl, —R*YR", —YR", and H;

each R" is independently selected from the group consisting of C3-14 alkyl and C3-14 alkenyl;

each R* is independently selected from the group consisting of C1-12 alkyl and C2-12 alkenyl;

each Y is independently a C3-6 carbocycle;

each X is independently selected from the group consisting of F, Cl, Br, and I; and m is selected from 5, 6, 7, 8, 9, 10, 11, 12, and 13, or salts or isomers thereof.

In some embodiments, another subset of compounds of Formula (I) includes those in which R1 is selected from the group consisting of C5-30 alkyl, C5-20 alkenyl, —R*YR", —YR", and —R"M'R';

R2 and R3 are independently selected from the group consisting of H, C1-14 alkyl, C2-14 alkenyl, —R*YR", —YR", and —R*OR", or R2 and R3, together with the atom to which they are attached, form a heterocycle or carbocycle;

R4 is selected from the group consisting of a C3-6 carbocycle, —(CH2)nQ, —(CH2)nCHQR, —CHQR, —CQ(R)2, and unsubstituted C1-6 alkyl, where Q is selected from a C3-6 carbocycle, a 5- to 14-membered heterocycle having one or more heteroatoms selected from N, O, and S, —OR, —O(CH2)nN(R)2, —C(O)OR, —OC(O)R, —CX3, —CX2H, —CXH2, —CN, —C(O)N(R)2, —N(R)C(O)R, —N(R)S(O)2R, —N(R)C(O)N(R)2, —N(R)C(S)N(R)2, —CRN(R)2C(O)OR, —N(R)R8, —O(CH2)nOR, —N(R)C(=NR9)N(R)2, —N(R)C(=CHR9)N(R)2, —OC(O)N(R)2, —N(R)C(O)OR, —N(OR)C(O)R, —N(OR)S(O)2R, —N(OR)C(O)OR, —N(OR)C(O)N(R)2, —N(OR)C(S)N(R)2, —N(OR)C(=NR9)N(R)2, —N(OR)C(=CHR9)N(R)2, —C(=NR9)R, —C(O)N(R)OR, and —C(=NR9)N(R)2, and each n is independently selected from 1, 2, 3, 4, and 5; and when Q is a 5- to 14-membered heterocycle and (i) R4 is —(CH2)nQ in which n is 1 or 2, or (ii) R4 is —(CH2)nCHQR in which n is 1, or (iii) R4 is —CHQR, and —CQ(R)2, then Q is either a 5- to 14-membered heteroaryl or 8- to 14-membered heterocycloalkyl;

each R5 is independently selected from the group consisting of C1-3 alkyl, C2-3 alkenyl, and H;

each R6 is independently selected from the group consisting of C1-3 alkyl, C2-3 alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)2-, —S—S—, an aryl group, and a heteroaryl group;

R7 is selected from the group consisting of C1-3 alkyl, C2-3 alkenyl, and H;

R8 is selected from the group consisting of C3-6 carbocycle and heterocycle;

R9 is selected from the group consisting of H, CN, NO2, C1-6 alkyl, —OR, —S(O)2R, —S(O)2N(R)2, C2-6 alkenyl, C3-6 carbocycle and heterocycle;

each R is independently selected from the group consisting of C1-3 alkyl, C2-3 alkenyl, and H;

each R' is independently selected from the group consisting of C1-18 alkyl, C2-18 alkenyl, —R*YR", —YR", and H;

each R" is independently selected from the group consisting of C3-14 alkyl and C3-14 alkenyl;

each R* is independently selected from the group consisting of C1-12 alkyl and C2-12 alkenyl;
each Y is independently a C3-6 carbocycle;
each X is independently selected from the group consisting of F, Cl, Br, and I; and
m is selected from 5, 6, 7, 8, 9, 10, 11, 12, and 13,
or salts or isomers thereof.

In some embodiments, another subset of compounds of Formula (I) includes those in which R1 is selected from the group consisting of C5-30 alkyl, C5-20 alkenyl, —R*YR", —YR", and —R"M'R';
R2 and R3 are independently selected from the group consisting of H, C1-14 alkyl, C2-14 alkenyl, —R*YR", —YR", and —R*OR", or R2 and R3, together with the atom to which they are attached, form a heterocycle or carbocycle;
R4 is selected from the group consisting of a C3-6 carbocycle, —(CH2)nQ, —(CH2)nCHQR, —CHQR, —CQ(R)2, and unsubstituted C1-6 alkyl, where Q is selected from a C3-6 carbocycle, a 5- to 14-membered heteroaryl having one or more heteroatoms selected from N, O, and S, —OR, —O(CH2)nN(R)2, —C(O)OR, —OC(O)R, —CX3, —CX2H, —CXH2, —CN, —C(O)N(R)2, —N(R)C(O)R, —N(R)S(O)2R, —N(R)C(O)N(R)2, —N(R)C(S)N(R)2, —CRN(R)2C(O)OR, —N(R)R8, —O(CH2)nOR, —N(R)C(=NR9)N(R)2, —N(R)C(=CHR9)N(R)2, —OC(O)N(R)2, —N(R)C(O)OR, —N(OR)C(O)R, —N(OR)S(O)2R, —N(OR)C(O)OR, —N(OR)C(O)N(R)2, —N(OR)C(S)N(R)2, —N(OR)C(=NR9)N(R)2, —N(OR)C(=CHR9)N(R)2, —C(=NR9)R, —C(O)N(R)OR, and —C(=NR9)N(R)2, and each n is independently selected from 1, 2, 3, 4, and 5;
each R5 is independently selected from the group consisting of C1-3 alkyl, C2-3 alkenyl, and H;
each R6 is independently selected from the group consisting of C1-3 alkyl, C2-3 alkenyl, and H;
M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)2-, —S—S—, an aryl group, and a heteroaryl group;
R7 is selected from the group consisting of C1-3 alkyl, C2-3 alkenyl, and H;
R8 is selected from the group consisting of C3-6 carbocycle and heterocycle;
R9 is selected from the group consisting of H, CN, NO2, C1-6 alkyl, —OR, —S(O)2R, —S(O)2N(R)2, C2-6 alkenyl, C3-6 carbocycle and heterocycle;
each R is independently selected from the group consisting of C1-3 alkyl, C2-3 alkenyl, and H;
each R' is independently selected from the group consisting of C1-18 alkyl, C2-18 alkenyl, —R*YR", —YR", and H;
each R" is independently selected from the group consisting of C3-14 alkyl and C3-14 alkenyl;
each R* is independently selected from the group consisting of C1-12 alkyl and C2-12 alkenyl;
each Y is independently a C3-6 carbocycle;
each X is independently selected from the group consisting of F, Cl, Br, and I; and
m is selected from 5, 6, 7, 8, 9, 10, 11, 12, and 13,
or salts or isomers thereof.

In some embodiments, another subset of compounds of Formula (I) includes those in which R1 is selected from the group consisting of C5-30 alkyl, C5-20 alkenyl, —R*YR", —YR", and —R"M'R';

R2 and R3 are independently selected from the group consisting of H, C2-14 alkyl, C2-14 alkenyl, —R*YR", —YR", and —R*OR", or R2 and R3, together with the atom to which they are attached, form a heterocycle or carbocycle;
R4 is —(CH2)nQ or —(CH2)nCHQR, where Q is —N(R)2, and n is selected from 3, 4, and 5;
each R5 is independently selected from the group consisting of C1-3 alkyl, C2-3 alkenyl, and H;
each R6 is independently selected from the group consisting of C1-3 alkyl, C2-3 alkenyl, and H;
M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)2-, —S—S—, an aryl group, and a heteroaryl group;
R7 is selected from the group consisting of C1-3 alkyl, C2-3 alkenyl, and H;
each R is independently selected from the group consisting of C1-3 alkyl, C2-3 alkenyl, and H;
each R' is independently selected from the group consisting of C1-18 alkyl, C2-18 alkenyl, —R*YR", —YR", and H;
each R" is independently selected from the group consisting of C3-14 alkyl and C3-14 alkenyl;
each R* is independently selected from the group consisting of C1-12 alkyl and C1-12 alkenyl;
each Y is independently a C3-6 carbocycle;
each X is independently selected from the group consisting of F, Cl, Br, and I; and
m is selected from 5, 6, 7, 8, 9, 10, 11, 12, and 13,
or salts or isomers thereof.

In some embodiments, another subset of compounds of Formula (I) includes those in which R1 is selected from the group consisting of C5-30 alkyl, C5-20 alkenyl, —R*YR", —YR", and —R"M'R';
R2 and R3 are independently selected from the group consisting of C1-14 alkyl, C2-14 alkenyl, —R*YR", —YR", and —R*OR", or R2 and R3, together with the atom to which they are attached, form a heterocycle or carbocycle;
R4 is selected from the group consisting of —(CH2)nQ, —(CH2)nCHQR, —CHQR, and —CQ(R)2, where Q is —N(R)2, and n is selected from 1, 2, 3, 4, and 5;
each R5 is independently selected from the group consisting of C1-3 alkyl, C2-3 alkenyl, and H;
each R6 is independently selected from the group consisting of C1-3 alkyl, C2-3 alkenyl, and H;
M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)2-, —S—S—, an aryl group, and a heteroaryl group;
R7 is selected from the group consisting of C1-3 alkyl, C2-3 alkenyl, and H;
each R is independently selected from the group consisting of C1-3 alkyl, C2-3 alkenyl, and H;
each R' is independently selected from the group consisting of C1-18 alkyl, C2-18 alkenyl, —R*YR", —YR", and H;
each R" is independently selected from the group consisting of C3-14 alkyl and C3-14 alkenyl;
each R* is independently selected from the group consisting of C1-12 alkyl and C1-12 alkenyl;
each Y is independently a C3-6 carbocycle;
each X is independently selected from the group consisting of F, Cl, Br, and I; and m is selected from 5, 6, 7, 8, 9, 10, 11, 12, and 13, or salts or isomers thereof.

In some embodiments, a subset of compounds of Formula (I) includes those of Formula (IA):

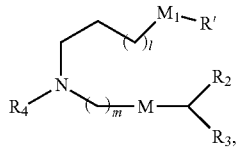

(IA)

or a salt or isomer thereof, wherein 1 is selected from 1, 2, 3, 4, and 5; m is selected from 5, 6, 7, 8, and 9; M1 is a bond or M'; R4 is unsubstituted C1-3 alkyl, or —(CH2)nQ, in which Q is OH, —NHC(S)N(R)2, —NHC(O)N(R)2, —N(R)C(O)R, —N(R)S(O)2R, —N(R)R8, —NHC(=NR9)N(R)2, —NHC(=CHR9)N(R)2, —OC(O)N(R)2, —N(R)C(O)OR, heteroaryl or heterocycloalkyl; M and M' are independently selected from —C(O)O—, —OC(O)—, —C(O)N(R')—, —P(O)(OR')O—, —S—S—, an aryl group, and a heteroaryl group; and R2 and R3 are independently selected from the group consisting of H, C1-14 alkyl, and C2-14 alkenyl.

In some embodiments, a subset of compounds of Formula (I) includes those of Formula (II):

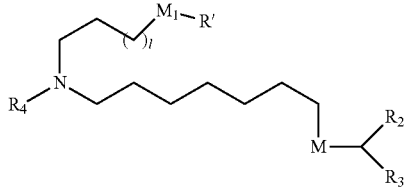

(II)

or a salt or isomer thereof, wherein 1 is selected from 1, 2, 3, 4, and 5; M1 is a bond or M'; R4 is unsubstituted C1-3 alkyl, or —(CH2)nQ, in which n is 2, 3, or 4, and Q is OH, —NHC(S)N(R)2, —NHC(O)N(R)2, —N(R)C(O)R, —N(R)S(O)2R, —N(R)R8, —NHC(=NR9)N(R)2, —NHC(=CHR9)N(R)2, —OC(O)N(R)2, —N(R)C(O)OR, heteroaryl or heterocycloalkyl; M and M' are independently selected from —C(O)O—, —OC(O)—, —C(O)N(R')—, —P(O)(OR')O—, —S—S—, an aryl group, and a heteroaryl group; and R2 and R3 are independently selected from the group consisting of H, C1-14 alkyl, and C2-14 alkenyl.

In some embodiments, a subset of compounds of Formula (I) includes those of Formula (IIa), (IIb), (IIc), or (IIe):

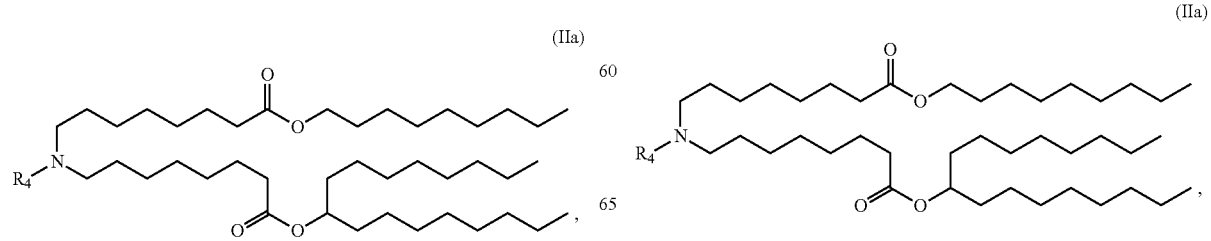

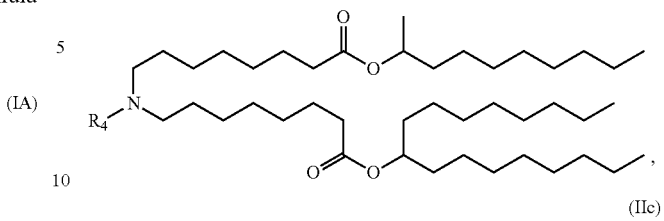

(IIb)

(IIc)

(IIe)

or a salt or isomer thereof, wherein R4 is as described herein.

In some embodiments, a subset of compounds of Formula (I) includes those of Formula (IId):

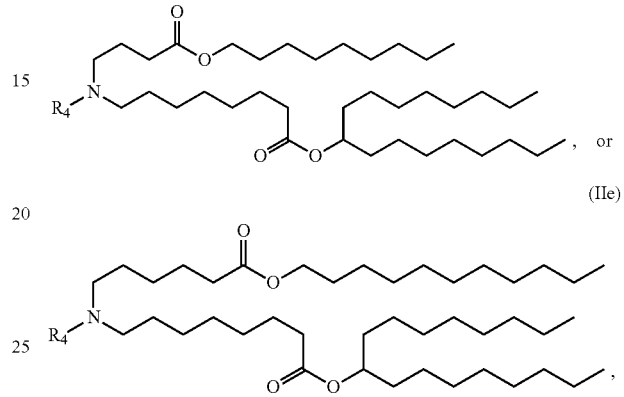

(IId)

or a salt or isomer thereof, wherein n is 2, 3, or 4; and m, R', R", and R2 through R6 are as described herein. For example, each of R2 and R3 may be independently selected from the group consisting of C5-14 alkyl and C5-14 alkenyl.

In some embodiments, a subset of compounds of Formula (I) includes those of Formula (IIa), (IIb), (IIc), or (IIe):

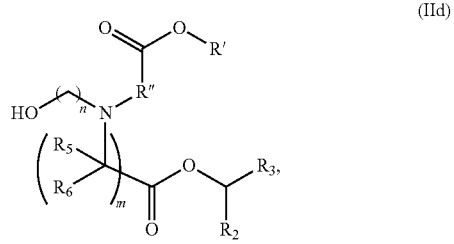

(IIa)

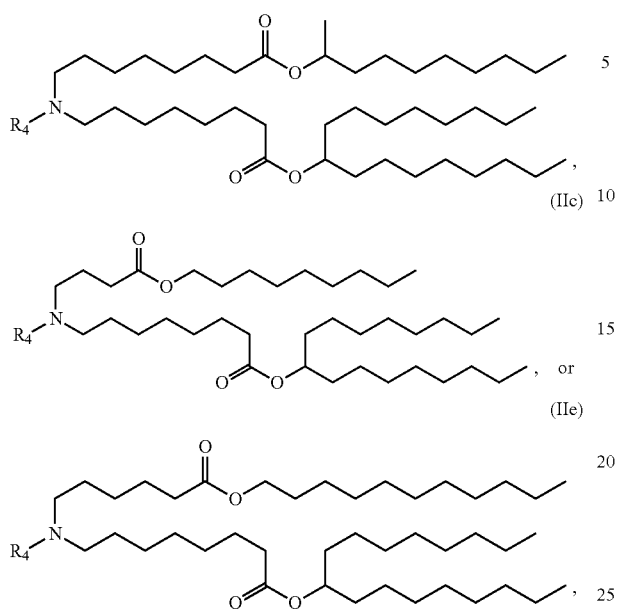

or a salt or isomer thereof, wherein R4 is as described herein.

In some embodiments, a subset of compounds of Formula (I) includes those of Formula (IId):

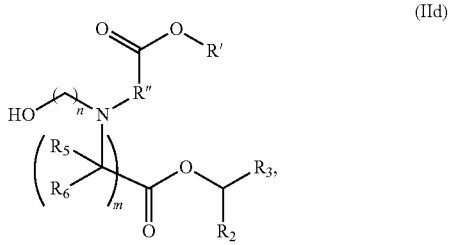

or a salt or isomer thereof, wherein n is 2, 3, or 4; and m, R', R", and R2 through R6 are as described herein. For example, each of R2 and R3 may be independently selected from the group consisting of C5-14 alkyl and C5-14 alkenyl.

In some embodiments, the compound of Formula (I) is compound 18 or 25:

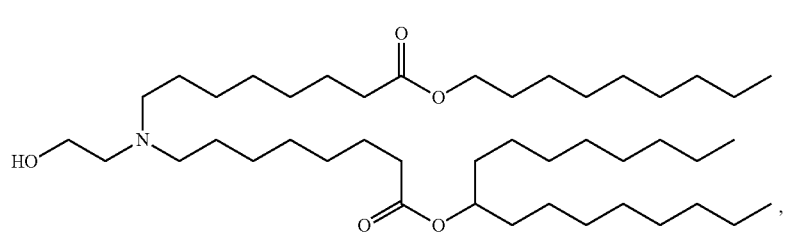

(Compound 18)

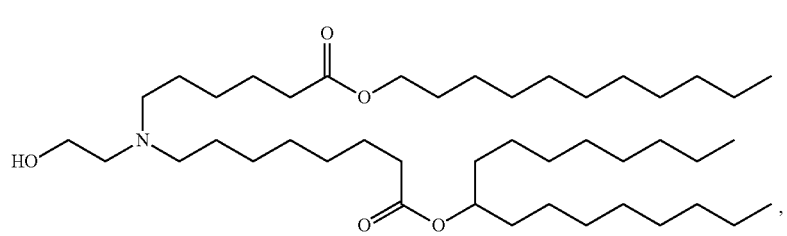

(Compound 25)

or salts and isomers thereof.

In some embodiments, the disclosure features a nanoparticle composition including a lipid component comprising a compound as described herein (e.g., a compound according to Formula (I), (IA), (II), (IIa), (IIb), (IIc), (IId) or (IIe)).

The lipid composition of a pharmaceutical composition disclosed herein can comprise one or more a polyethylene glycol (PEG) lipid.

As used herein, the term "PEG-lipid" refers to polyethylene glycol (PEG)-modified lipids. Non-limiting examples of PEG-lipids include PEG-modified phosphatidylethanolamine and phosphatidic acid, PEG-ceramide conjugates (e.g., PEG-CerC14 or PEG-CerC20), PEG-modified dialkylamines and PEG-modified 1,2-diacyloxypropan-3-amines. Such lipids are also referred to as PEGylated lipids. For example, a PEG lipid can be PEG-c-DOMG, PEG-DMG, PEG-DLPE, PEG-DMPE, PEG-DPPC, or a PEG-DSPE lipid.

In some embodiments, the PEG-lipid includes, but not limited to 1,2-dimyristoyl-sn-glycerol methoxypolyethylene glycol (PEG-DMG), 1,2-distearoyl-sn-glycero-3-phosphoethanolamine-N-[amino(polyethylene glycol)] (PEG-DSPE), PEG-disteryl glycerol (PEG-DSG), PEG-dipalmetoleyl, PEG-dioleyl, PEG-distearyl, PEG-diacylglycamide (PEG-DAG), PEG-dipalmitoyl phosphatidylethanolamine (PEG-DPPE), or PEG-1,2-dimyristyloxlpropyl-3-amine (PEG-c-DMA).

In one embodiment, the PEG-lipid is selected from the group consisting of a PEG-modified phosphatidylethanolamine, a PEG-modified phosphatidic acid, a PEG-modified ceramide, a PEG-modified dialkylamine, a PEG-modified diacylglycerol, a PEG-modified dialkylglycerol, and mixtures thereof.

In some embodiments, the lipid moiety of the PEG-lipids includes those having lengths of from about C14 to about C22, preferably from about C14 to about C16. In some embodiments, a PEG moiety, for example an mPEG-NH2, has a size of about 1000, 2000, 5000, 10,000, 15,000 or 20,000 daltons. In one embodiment, the PEG-lipid is PEG2k-DMG.

In one embodiment, the lipid nanoparticles described herein can comprise a PEG lipid which is a non-diffusible PEG. Non-limiting examples of non-diffusible PEGs include PEG-DSG and PEG-DSPE.

In certain embodiments, a PEG lipid useful in the present invention is a PEGylated fatty acid. In certain embodiments, a PEG lipid useful in the present invention is a compound of Formula (VIII). Provided herein are compounds of Formula (VIII):

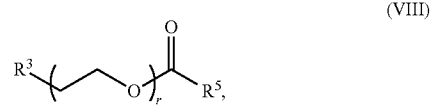

(VIII)

or a salts thereof, wherein:
R3 is —ORO;
RO is hydrogen, optionally substituted alkyl or an oxygen protecting group;
r is an integer between 1 and 100, inclusive and in some embodiments is 45;
R5 is optionally substituted C10-40 alkyl, optionally substituted C10-40 alkenyl, or optionally substituted C10-40 alkynyl; and optionally one or more methylene groups of R5 are replaced with optionally substituted carbocyclylene, optionally substituted heterocyclylene, optionally substituted arylene, optionally substituted heteroarylene, N(RN), —O, S, C(O), C(O)N(RN), NRNC(O), NRNC(O)N(RN), C(O)O, OC(O), OC(O)O, —OC(O)N(RN), NRNC(O)O, C(O)S, SC(O), C(=NRN), C(=NRN)N(RN), NRNC(=NRN), —NRNC(=NRN)N(RN), C(S), C(S)N(RN), NRNC(S), NRNC(S)N(RN), S(O), OS(O), S(O)O, OS(O)O, OS(O)2, S(O)2O, OS(O)2O, N(RN)S(O), S(O)N(RN), N(RN)S(O)N(RN), —OS(O)N(RN), N(RN)S(O)O, S(O)2, N(RN)S(O)2, S(O)2N(RN), N(RN)S(O)2N(RN), —OS(O)2N(RN), or N(RN)S(O)2O; and
each instance of RN is independently hydrogen, optionally substituted alkyl, or a nitrogen protecting group.

In certain embodiments, the compound of Formula (VIII) is of Formula (VIII-OH):

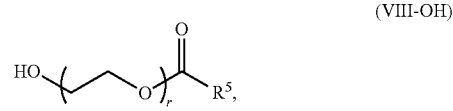

(VIII-OH)

or a salt thereof. In some embodiments, r is 45.

In certain embodiments, the PEG lipid is of one of the following formulae:

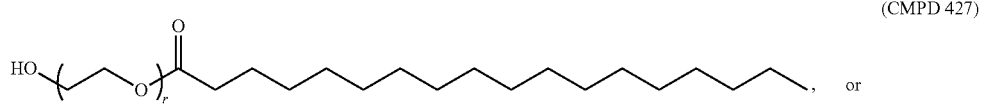

(CMPD 427)

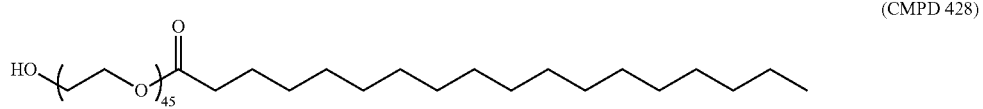

(CMPD 428)

or salts thereof.

In one embodiment, the amount of PEG-lipid in the lipid composition of a pharmaceutical composition disclosed herein ranges from about 0.1 mol % to about 5 mol %, from about 0.5 mol % to about 5 mol %, from about 1 mol % to about 5 mol %, from about 1.5 mol % to about 5 mol %, from about 2 mol % to about 5 mol % mol %, from about 0.1 mol % to about 4 mol %, from about 0.5 mol % to about 4 mol %, from about 1 mol % to about 4 mol %, from about 1.5 mol % to about 4 mol %, from about 2 mol % to about 4 mol %, from about 0.1 mol % to about 3 mol %, from about 0.5 mol % to about 3 mol %, from about 1 mol % to about 3 mol %, from about 1.5 mol % to about 3 mol %, from about 2 mol % to about 3 mol %, from about 0.1 mol % to about 2 mol %, from about 0.5 mol % to about 2 mol %, from about 1 mol % to about 2 mol %, from about 1.5 mol % to about 2 mol %, from about 0.1 mol % to about 1.5 mol %, from about 0.5 mol % to about 1.5 mol %, or from about 1 mol % to about 1.5 mol %.

In one embodiment, the amount of PEG-lipid in the lipid composition disclosed herein is about 2 mol %. In one embodiment, the amount of PEG-lipid in the lipid composition disclosed herein is about 1.5 mol %.

In one embodiment, the amount of PEG-lipid in the lipid composition disclosed herein is at least about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, or 5 mol %.

In some aspects, the lipid composition of the pharmaceutical compositions disclosed herein does not comprise a PEG-lipid.

In some embodiments the LNP is comprised of Compounds 18 and 428.

In some embodiments, the LNP has a molar ratio of 50:38.5:10:1.5 of Compound 18:Phospholipid:Cholesterol:Compound 428. In some embodiments, the LNP has a molar ratio of 50:38.5:10:1.5 of Compound 18:DSPC:Cholesterol:Compound 428.

In some embodiments, the LNP has a molar ratio of 40:38.5:20:1.5 of Compound 18:Phospholipid:Cholesterol:Compound 428. In some embodiments, the LNP has a molar ratio of 40:38.5:20:1.5 of Compound 18:DSPC:Cholesterol:Compound 428.

In some embodiments, a nanoparticle composition can have the formulation of Compound 18:Phospholipid:Chol:Compound 428 with a mole ratio of 50:10:38.5:1.5. In some embodiments, a nanoparticle composition can have the formulation of Compound 18:DSPC:Chol:Compound 428 with a mole ratio of 50:10:38.5:1.5.

In some embodiments the LNP is comprised of Compounds 25.

Relative amounts of the active ingredient, the pharmaceutically acceptable excipient, and/or any additional ingredients in a vaccine composition may vary, depending upon the identity, size, and/or condition of the subject being treated and further depending upon the route by which the composition is to be administered. For example, the composition may comprise between 0.1% and 99% (w/w) of the active ingredient. By way of example, the composition may comprise between 0.1% and 100%, e.g., between 0.5 and 50%, between 1-30%, between 5-80%, at least 80% (w/w) active ingredient.

In some embodiments, the RNA vaccine composition may comprise the polynucleotide described herein, formulated in a lipid nanoparticle comprising MC3, Cholesterol, DSPC and PEG2000-DMG, the buffer trisodium citrate, sucrose and water for injection. As a non-limiting example, the composition comprises: 2.0 mg/mL of drug substance (e.g., polynucleotides encoding H10N8 influenza virus), 21.8 mg/mL of MC3, 10.1 mg/mL of cholesterol, 5.4 mg/mL of DSPC, 2.7 mg/mL of PEG2000-DMG, 5.16 mg/mL of trisodium citrate, 71 mg/mL of sucrose and 1.0 mL of water for injection.

In some embodiments, a nanoparticle (e.g., a lipid nanoparticle) has a mean diameter of 10-500 nm, 20-400 nm, 30-300 nm, 40-200 nm. In some embodiments, a nanoparticle (e.g., a lipid nanoparticle) has a mean diameter of 50-150 nm, 50-200 nm, 80-100 nm or 80-200 nm.

In some embodiments, the RNA vaccine formulation comprising the polynucleotide is a nanoparticle which may comprise at least one lipid. The lipid may be selected from, but is not limited to, DLin-DMA, DLin-K-DMA, 98N12-5, C12-200, DLin-MC3-DMA, DLin-KC2-DMA, DODMA, PLGA, PEG, PEG-DMG, PEGylated lipids and amino alcohol lipids. In another aspect, the lipid may be a cationic lipid such as, but not limited to, DLin-DMA, DLin-D-DMA, DLin-MC3-DMA, DLin-KC2-DMA, DODMA and amino alcohol lipids. The amino alcohol cationic lipid may be the lipids described in and/or made by the methods described in US Patent Publication No. US20130150625, herein incorporated by reference in its entirety. As a non-limiting example, the cationic lipid may be 2-amino-3-[(9Z,12Z)-octadeca-9,12-dien-1-yloxy]-2-{[(9Z,2Z)-octadeca-9,12-dien-1-yloxy]methyl}propan-1-ol (Compound 1 in US20130150625); 2-amino-3-[(9Z)-octadec-9-en-1-yloxy]-2-{[(9Z)-octadec-9-en-1-yloxy]methyl}propan-1-ol (Compound 2 in US20130150625); 2-amino-3-[(9Z,12Z)-octadeca-9,12-dien-1-yloxy]-2-[(octyloxy)methyl]propan-1-ol (Compound 3 in US20130150625); and 2-(dimethylamino)-3-[(9Z,12Z)-octadeca-9,12-dien-1-yloxy]-2-{[(9Z,12Z)-octadeca-9,12-dien-1-yloxy]methyl}propan-1-ol (Compound 4 in US20130150625); or any pharmaceutically acceptable salt or stereoisomer thereof.

Lipid nanoparticle formulations typically comprise a lipid, in particular, an ionizable cationic lipid, for example, 2,2-dilinoleyl-4-dimethylaminoethyl-[1,3]-dioxolane (DLin-KC2-DMA), dilinoleyl-methyl-4-dimethylaminobutyrate (DLin-MC3-DMA), or di((Z)-non-2-en-1-yl) 9-((4-(dimethylamino)butanoyl)oxy)heptadecanedioate (L319), and further comprise a neutral lipid, a sterol and a molecule capable of reducing particle aggregation, for example a PEG or PEG-modified lipid.

In some embodiments, the lipid nanoparticle formulation consists essentially of (i) at least one lipid selected from the group consisting of 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy) heptadecanedioate (L319); (ii) a neutral lipid selected from DSPC, DPPC, POPC, DOPE and SM; (iii) a sterol, e.g., cholesterol; and (iv) a PEG-lipid, e.g., PEG-DMG or PEG-cDMA, in a molar ratio of about 20-60% cationic lipid:5-25% neutral lipid:25-55% sterol:0.5-15% PEG-lipid.

In some embodiments, the formulation includes from about 25% to about 75% on a molar basis of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), e.g., from about 35 to about 65%, from about 45 to about 65%, about 60%, about 57.5%, about 50% or about 40% on a molar basis.

In some embodiments, the formulation includes from about 0.5% to about 15% on a molar basis of the neutral lipid e.g., from about 3 to about 12%, from about 5 to about 10% or about 15%, about 10%, or about 7.5% on a molar basis. Exemplary neutral lipids include, but are not limited to, DSPC, POPC, DPPC, DOPE and SM. In some embodiments, the formulation includes from about 5% to about 50% on a molar basis of the sterol (e.g., about 15 to about 45%, about 20 to about 40%, about 40%, about 38.5%, about 35%, or about 31% on a molar basis. An exemplary sterol is cholesterol. In some embodiments, the formulation includes from about 0.5% to about 20% on a molar basis of the PEG or PEG-modified lipid (e.g., about 0.5 to about 10%, about 0.5 to about 5%, about 1.5%, about 0.5%, about 1.5%, about 3.5%, or about 5% on a molar basis. In some embodiments, the PEG or PEG modified lipid comprises a PEG molecule of an average molecular weight of 2,000 Da. In other embodiments, the PEG or PEG modified lipid comprises a PEG molecule of an average molecular weight of less than 2,000, for example around 1,500 Da, around 1,000 Da, or around 500 Da. Exemplary PEG-modified lipids include, but are not limited to, PEG-distearoyl glycerol (PEG-DMG) (also referred herein as PEG-C14 or C14-PEG), PEG-cDMA (further discussed in Reyes et al. J. Controlled Release, 107, 276-287 (2005) the contents of which are herein incorporated by reference in its entirety)

In some embodiments, the formulations of the inventions include 25-75% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), 0.5-15% of the neutral lipid, 5-50% of the sterol, and 0.5-20% of the PEG or PEG-modified lipid on a molar basis.

In some embodiments, the formulations of the inventions include 35-65% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), 3-12% of the neutral lipid, 15-45% of the sterol, and 0.5-10% of the PEG or PEG-modified lipid on a molar basis.

In some embodiments, the formulations of the inventions include 45-65% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), 5-10% of the neutral lipid, 25-40% of the sterol, and 0.5-10% of the PEG or PEG-modified lipid on a molar basis.

In some embodiments, the formulations of the inventions include about 60% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), about 7.5% of the neutral lipid, about 31% of the sterol, and about 1.5% of the PEG or PEG-modified lipid on a molar basis.

In some embodiments, the formulations of the inventions include about 50% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), about 10% of the neutral lipid, about 38.5% of the sterol, and about 1.5% of the PEG or PEG-modified lipid on a molar basis.

In some embodiments, the formulations of the inventions include about 50% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), about 10% of the neutral lipid, about 35% of the sterol, about 4.5% or about 5% of the PEG or PEG-modified lipid, and about 0.5% of the targeting lipid on a molar basis.

In some embodiments, the formulations of the inventions include about 40% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), about 15% of the neutral lipid, about 40% of the sterol, and about 5% of the PEG or PEG-modified lipid on a molar basis.

In some embodiments, the formulations of the inventions include about 57.2% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), about 7.1% of the neutral lipid, about 34.3% of the sterol, and about 1.4% of the PEG or PEG-modified lipid on a molar basis.

In some embodiments, the formulations of the inventions include about 57.5% of a cationic lipid selected from the PEG lipid is PEG-cDMA (PEG-cDMA is further discussed in Reyes et al. (J. Controlled Release, 107, 276-287 (2005), the contents of which are herein incorporated by reference in its entirety), about 7.5% of the neutral lipid, about 31.5% of the sterol, and about 3.5% of the PEG or PEG-modified lipid on a molar basis.

In preferred embodiments, lipid nanoparticle formulation consists essentially of a lipid mixture in molar ratios of about 20-70% cationic lipid:5-45% neutral lipid:20-55% cholesterol:0.5-15% PEG-modified lipid; more preferably in a molar ratio of about 20-60% cationic lipid:5-25% neutral lipid:25-55% cholesterol:0.5-15% PEG-modified lipid.

In particular embodiments, the molar lipid ratio is approximately 50/10/38.5/1.5 (mol % cationic lipid/neutral lipid, e.g., DSPC/Chol/PEG-modified lipid, e.g., PEG-DMG, PEG-DSG or PEG-DPG), 57.2/7.1134.3/1.4 (mol % cationic lipid/neutral lipid, e.g., DPPC/Chol/PEG-modified lipid, e.g., PEG-cDMA), 40/15/40/5 (mol % cationic lipid/neutral lipid, e.g., DSPC/Chol/PEG-modified lipid, e.g., PEG-DMG), 50/10/35/4.5/0.5 (mol % cationic lipid/neutral lipid, e.g., DSPC/Chol/PEG-modified lipid, e.g., PEG-DSG), 50/10/35/5 (cationic lipid/neutral lipid, e.g., DSPC/Chol/PEG-modified lipid, e.g., PEG-DMG), 40/10/40/10 (mol % cationic lipid/neutral lipid, e.g., DSPC/Chol/PEG-modified lipid, e.g., PEG-DMG or PEG-cDMA), 35/15/40/10 (mol % cationic lipid/neutral lipid, e.g., DSPC/Chol/PEG-modified lipid, e.g., PEG-DMG or PEG-cDMA) or 52/13/30/5 (mol % cationic lipid/neutral lipid, e.g., DSPC/Chol/PEG-modified lipid, e.g., PEG-DMG or PEG-cDMA).

In some embodiments, the lipid nanoparticle formulations described herein may comprise a cationic lipid, a PEG lipid and a structural lipid and optionally comprise a non-cationic lipid. As a non-limiting example, the lipid nanoparticle may comprise about 40-60% of cationic lipid, about 5-15% of a non-cationic lipid, about 1-2% of a PEG lipid and about 30-50% of a structural lipid. As another non-limiting example, the lipid nanoparticle may comprise about 50% cationic lipid, about 10% non-cationic lipid, about 1.5% PEG lipid and about 38.5% structural lipid. As yet another non-limiting example, the lipid nanoparticle may comprise about 55% cationic lipid, about 10% non-cationic lipid, about 2.5% PEG lipid and about 32.5% structural lipid. In some embodiments, the cationic lipid may be any cationic lipid described herein such as, but not limited to, DLin-KC2-DMA, DLin-MC3-DMA and L319.

In some embodiments, the lipid nanoparticle formulations described herein may be 4 component lipid nanoparticles. The lipid nanoparticle may comprise a cationic lipid, a non-cationic lipid, a PEG lipid and a structural lipid. As a non-limiting example, the lipid nanoparticle may comprise about 40-60% of cationic lipid, about 5-15% of a non-cationic lipid, about 1-2% of a PEG lipid and about 30-50% of a structural lipid. As another non-limiting example, the lipid nanoparticle may comprise about 50% cationic lipid, about 10% non-cationic lipid, about 1.5% PEG lipid and about 38.5% structural lipid. As yet another non-limiting example, the lipid nanoparticle may comprise about 55% cationic lipid, about 10% non-cationic lipid, about 2.5% PEG lipid and about 32.5% structural lipid. In some embodiments, the cationic lipid may be any cationic lipid described herein such as, but not limited to, DLin-KC2-DMA, DLin-MC3-DMA and L319.

In some embodiments, the lipid nanoparticle formulations described herein may comprise a cationic lipid, a non-cationic lipid, a PEG lipid and a structural lipid. As a non-limiting example, the lipid nanoparticle comprise about 50% of the cationic lipid DLin-KC2-DMA, about 10% of the non-cationic lipid DSPC, about 1.5% of the PEG lipid PEG-DOMG and about 38.5% of the structural lipid cholesterol. As a non-limiting example, the lipid nanoparticle comprise about 50% of the cationic lipid DLin-MC3-DMA, about 10% of the non-cationic lipid DSPC, about 1.5% of the PEG lipid PEG-DOMG and about 38.5% of the structural lipid cholesterol. As a non-limiting example, the lipid nanoparticle comprise about 50% of the cationic lipid DLin-MC3-DMA, about 10% of the non-cationic lipid DSPC, about 1.5% of the PEG lipid PEG-DMG and about 38.5% of the structural lipid cholesterol. As yet another non-limiting example, the lipid nanoparticle comprise about 55% of the cationic lipid L319, about 10% of the non-cationic lipid DSPC, about 2.5% of the PEG lipid PEG-DMG and about 32.5% of the structural lipid cholesterol.

In some embodiments, RNA vaccine may be delivered using smaller LNPs. Such particles may comprise a diameter from below 0.1 um up to 100 nm such as, but not limited to, less than 0.1 um, less than 1.0 um, less than 5 um, less than 10 um, less than 15 um, less than 20 um, less than 25 um, less than 30 um, less than 35 um, less than 40 um, less than 50 um, less than 55 um, less than 60 um, less than 65 um, less than 70 um, less than 75 um, less than 80 um, less than 85 um, less than 90 um, less than 95 um, less than 100 um, less than 125 um, less than 150 um, less than 175 um, less than 200 um, less than 225 um, less than 250 um, less than 275 um, less than 300 um, less than 325 um, less than 350 um, less than 375 um, less than 400 um, less than 425 um, less than 450 um, less than 475 um, less than 500 um, less than 525 um, less than 550 um, less than 575 um, less than 600 um, less than 625 um, less than 650 um, less than 675 um, less than 700 um, less than 725 um, less than 750 um, less than 775 um, less than 800 um, less than 825 um, less than 850 um, less than 875 um, less than 900 um, less than 925 um, less than 950 um, and less than 975 um.

In another embodiment, RNA vaccines may be delivered using smaller LNPs which may comprise a diameter from about 1 nm to about 100 nm, from about 1 nm to about 10 nm, about 1 nm to about 20 nm, from about 1 nm to about 30 nm, from about 1 nm to about 40 nm, from about 1 nm to about 50 nm, from about 1 nm to about 60 nm, from about 1 nm to about 70 nm, from about 1 nm to about 80 nm, from about 1 nm to about 90 nm, from about 5 nm to about from 100 nm, from about 5 nm to about 10 nm, about 5 nm to about 20 nm, from about 5 nm to about 30 nm, from about 5 nm to about 40 nm, from about 5 nm to about 50 nm, from about 5 nm to about 60 nm, from about 5 nm to about 70 nm, from about 5 nm to about 80 nm, from about 5 nm to about 90 nm, about 10 to about 50 nM, from about 20 to about 50 nm, from about 30 to about 50 nm, from about 40 to about 50 nm, from about 20 to about 60 nm, from about 30 to about 60 nm, from about 40 to about 60 nm, from about 20 to about 70 nm, from about 30 to about 70 nm, from about 40 to about 70 nm, from about 50 to about 70 nm, from about 60 to about 70 nm, from about 20 to about 80 nm, from about 30 to about 80 nm, from about 40 to about 80 nm, from about 50 to about 80 nm, from about 60 to about 80 nm, from about 20 to about 90 nm, from about 30 to about 90 nm, from about 40 to about 90 nm, from about 50 to about 90 nm, from about 60 to about 90 nm and/or from about 70 to about 90 nm.

In some embodiments, a LNP of the disclosure comprises an N:P ratio of from about 2:1 to about 30:1.

In some embodiments, a LNP of the disclosure comprises an N:P ratio of about 6:1.

In some embodiments, a LNP of the disclosure comprises an N:P ratio of about 3:1.

In some embodiments, a LNP of the disclosure comprises a wt/wt ratio of the ionizable cationic lipid component to the RNA of from about 10:1 to about 100:1.

In some embodiments, a LNP of the disclosure comprises a wt/wt ratio of the ionizable cationic lipid component to the RNA of about 20:1.

In some embodiments, a LNP of the disclosure comprises a wt/wt ratio of the ionizable cationic lipid component to the RNA of about 10:1.

In some embodiments, a LNP of the disclosure has a mean diameter from about 50 nm to about 150 nm.

In some embodiments, a LNP of the disclosure has a mean diameter from about 70 nm to about 120 nm.

Modes of Vaccine Administration

Influenza RNA vaccines may be administered by any route which results in a therapeutically effective outcome. These include, but are not limited to, intradermal, intramuscular, and/or subcutaneous administration. The present disclosure provides methods comprising administering RNA vaccines to a subject in need thereof. The exact amount required will vary from subject to subject, depending on the species, age, and general condition of the subject, the severity of the disease, the particular composition, its mode of administration, its mode of activity, and the like. influenza RNA vaccines compositions are typically formulated in dosage unit form for ease of administration and uniformity of dosage. It will be understood, however, that the total daily usage of influenza RNA vaccines compositions may be decided by the attending physician within the scope of sound medical judgment. The specific therapeutically effective, prophylactically effective, or appropriate imaging dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

In some embodiments, influenza RNA vaccines compositions may be administered at dosage levels sufficient to deliver 0.0001 mg/kg to 100 mg/kg, 0.001 mg/kg to 0.05 mg/kg, 0.005 mg/kg to 0.05 mg/kg, 0.001 mg/kg to 0.005 mg/kg, 0.05 mg/kg to 0.5 mg/kg, 0.01 mg/kg to 50 mg/kg, 0.1 mg/kg to 40 mg/kg, 0.5 mg/kg to 30 mg/kg, 0.01 mg/kg to 10 mg/kg, 0.1 mg/kg to 10 mg/kg, or 1 mg/kg to 25 mg/kg, of subject body weight per day, one or more times a day, per week, per month, etc. to obtain the desired therapeutic, diagnostic, prophylactic, or imaging effect (see e.g., the range of unit doses described in International Publication No WO2013078199, herein incorporated by reference in its entirety). The desired dosage may be delivered three times a day, two times a day, once a day, every other day, every third day, every week, every two weeks, every three weeks, every four weeks, every 2 months, every three months, every 6 months, etc. In certain embodiments, the desired dosage may be delivered using multiple administrations (e.g., two, three, four, five, six, seven, eight, nine, ten, eleven, twelve, thirteen, fourteen, or more administrations). When multiple administrations are employed, split dosing regimens such as those described herein may be used. In exemplary embodiments, influenza RNA vaccines compositions may be administered at dosage levels sufficient to deliver 0.0005 mg/kg to 0.01 mg/kg, e.g., about 0.0005 mg/kg to about 0.0075 mg/kg, e.g., about 0.0005 mg/kg, about 0.001 mg/kg, about 0.002 mg/kg, about 0.003 mg/kg, about 0.004 mg/kg or about 0.005 mg/kg.

In some embodiments, influenza RNA vaccine compositions may be administered once or twice (or more) at dosage levels sufficient to deliver 0.025 mg/kg to 0.250 mg/kg, 0.025 mg/kg to 0.500 mg/kg, 0.025 mg/kg to 0.750 mg/kg, or 0.025 mg/kg to 1.0 mg/kg.

In some embodiments, influenza RNA vaccine compositions may be administered twice (e.g., Day 0 and Day 7, Day 0 and Day 14, Day 0 and Day 21, Day 0 and Day 28, Day 0 and Day 60, Day 0 and Day 90, Day 0 and Day 120, Day 0 and Day 150, Day 0 and Day 180, Day 0 and 3 months later, Day 0 and 6 months later, Day 0 and 9 months later, Day 0 and 12 months later, Day 0 and 18 months later, Day 0 and 2 years later, Day 0 and 5 years later, or Day 0 and 10 years later) at a total dose of or at dosage levels sufficient to deliver a total dose of 0.0100 mg, 0.025 mg, 0.050 mg, 0.075 mg, 0.100 mg, 0.125 mg, 0.150 mg, 0.175 mg, 0.200 mg, 0.225 mg, 0.250 mg, 0.275 mg, 0.300 mg, 0.325 mg, 0.350 mg, 0.375 mg, 0.400 mg, 0.425 mg, 0.450 mg, 0.475 mg, 0.500 mg, 0.525 mg, 0.550 mg, 0.575 mg, 0.600 mg, 0.625 mg, 0.650 mg, 0.675 mg, 0.700 mg, 0.725 mg, 0.750 mg, 0.775 mg, 0.800 mg, 0.825 mg, 0.850 mg, 0.875 mg, 0.900 mg, 0.925 mg, 0.950 mg, 0.975 mg, or 1.0 mg. Higher and lower dosages and frequency of administration are encompassed by the present disclosure. For example, an influenza RNA vaccine composition may be administered three or four times.

In some embodiments, influenza RNA vaccine compositions may be administered twice (e.g., Day 0 and Day 7, Day 0 and Day 14, Day 0 and Day 21, Day 0 and Day 28, Day 0 and Day 60, Day 0 and Day 90, Day 0 and Day 120, Day 0 and Day 150, Day 0 and Day 180, Day 0 and 3 months later, Day 0 and 6 months later, Day 0 and 9 months later, Day 0 and 12 months later, Day 0 and 18 months later, Day 0 and 2 years later, Day 0 and 5 years later, or Day 0 and 10 years later) at a total dose of or at dosage levels sufficient to deliver a total dose of 0.010 mg, 0.025 mg, 0.100 mg or 0.400 mg.

In some embodiments the RNA vaccine for use in a method of vaccinating a subject is administered to the subject in a single dosage of between 10 µg/kg and 400 µg/kg of the nucleic acid vaccine in an effective amount to vaccinate the subject. In some embodiments the RNA vaccine for use in a method of vaccinating a subject is administered to the subject in a single dosage of between 10 µg and 400 µg of the nucleic acid vaccine in an effective amount to vaccinate the subject. In some embodiments, an influenza RNA (e.g., mRNA) vaccine for use in a method of vaccinating a subject is administered to the subject in a single dosage of 10 µg. In some embodiments, an influenza RNA vaccine for use in a method of vaccinating a subject is administered to the subject in a single dosage of 2 µg. In some embodiments, an influenza RNA vaccine for use in a method of vaccinating a subject is administered to the subject in two dosages of 10 µg. In some embodiments, an influenza RNA vaccine for use in a method of vaccinating a subject is administered the subject two dosages of 2 µg.

An influenza RNA vaccine pharmaceutical composition described herein can be formulated into a dosage form described herein, such as an intranasal, intratracheal, or injectable (e.g., intravenous, intraocular, intravitreal, intramuscular, intradermal, intracardiac, intraperitoneal, and subcutaneous).

Influenza RNA Vaccine Formulations and Methods of Use

Some aspects of the present disclosure provide formulations of the influenza RNA (e.g., mRNA) vaccine, wherein the influenza RNA vaccine is formulated in an effective amount to produce an antigen specific immune response in a subject (e.g., production of antibodies specific to an anti-influenza antigenic polypeptide). "An effective amount" is a dose of an influenza RNA (e.g., mRNA) vaccine effective to produce an antigen-specific immune response. Also provided herein are methods of inducing an antigen-specific immune response in a subject.

In some embodiments, the antigen-specific immune response is characterized by measuring an anti-influenza antigenic polypeptide antibody titer produced in a subject administered an influenza RNA (e.g., mRNA) vaccine as provided herein. An antibody titer is a measurement of the amount of antibodies within a subject, for example, antibodies that are specific to a particular antigen (e.g., an anti-influenza antigenic polypeptide) or epitope of an antigen. Antibody titer is typically expressed as the inverse of the greatest dilution that provides a positive result. Enzyme-linked immunosorbent assay (ELISA) is a common assay for determining antibody titers, for example.

In some embodiments, an antibody titer is used to assess whether a subject has had an infection or to determine whether immunizations are required. In some embodiments, an antibody titer is used to determine the strength of an autoimmune response, to determine whether a booster immunization is needed, to determine whether a previous vaccine was effective, and to identify any recent or prior infections. In accordance with the present disclosure, an antibody titer may be used to determine the strength of an immune response induced in a subject by the influenza RNA vaccine.

In some embodiments, an anti-influenza antigenic polypeptide antibody titer produced in a subject is increased by at least 1 log relative to a control. For example, anti-influenza antigenic polypeptide antibody titer produced in a subject may be increased by at least 1.5, at least 2, at least 2.5, or at least 3 log relative to a control. In some embodiments, the anti-influenza antigenic polypeptide antibody titer produced in the subject is increased by 1, 1.5, 2, 2.5 or 3 log relative to a control. In some embodiments, the anti-influenza antigenic polypeptide antibody titer produced in the subject is increased by 1-3 log relative to a control. For example, the anti-influenza antigenic polypeptide antibody titer produced in a subject may be increased by 1-1.5, 1-2, 1-2.5, 1-3, 1.5-2, 1.5-2.5, 1.5-3, 2-2.5, 2-3, or 2.5-3 log relative to a control.

In some embodiments, the anti-influenza antigenic polypeptide antibody titer produced in a subject is increased at least 2 times relative to a control. For example, the anti-influenza antigenic polypeptide antibody titer produced in a subject may be increased at least 3 times, at least 4 times, at least 5 times, at least 6 times, at least 7 times, at least 8 times, at least 9 times, or at least 10 times relative to a control. In some embodiments, the anti-influenza antigenic polypeptide antibody titer produced in the subject is increased 2, 3, 4, 5, 6, 7, 8, 9, or 10 times relative to a control. In some embodiments, the anti-influenza antigenic polypeptide antibody titer produced in a subject is increased 2-10 times relative to a control. For example, the anti-influenza antigenic polypeptide antibody titer produced in a subject may be increased 2-10, 2-9, 2-8, 2-7, 2-6, 2-5, 2-4, 2-3, 3-10, 3-9, 3-8, 3-7, 3-6, 3-5, 3-4, 4-10, 4-9, 4-8, 4-7, 4-6, 4-5, 5-10, 5-9, 5-8, 5-7, 5-6, 6-10, 6-9, 6-8, 6-7, 7-10, 7-9, 7-8, 8-10, 8-9, or 9-10 times relative to a control.

A control, in some embodiments, is the anti-influenza antigenic polypeptide antibody titer produced in a subject who has not been administered an influenza RNA (e.g., mRNA) vaccine. In some embodiments, a control is an anti-influenza antigenic polypeptide antibody titer produced in a subject who has been administered a live attenuated influenza vaccine. An attenuated vaccine is a vaccine produced by reducing the virulence of a viable (live). An attenuated virus is altered in a manner that renders it harmless or less virulent relative to live, unmodified virus. In some embodiments, a control is an anti-influenza antigenic polypeptide antibody titer produced in a subject administered inactivated influenza vaccine. In some embodiments, a control is an anti-influenza antigenic polypeptide antibody titer produced in a subject administered a recombinant or purified influenza protein vaccine. Recombinant protein vaccines typically include protein antigens that either have been produced in a heterologous expression system (e.g., bacteria or yeast) or purified from large amounts of the pathogenic organism.

In some embodiments, an effective amount of an influenza RNA (e.g., mRNA) vaccine is a dose that is reduced compared to the standard of care dose of a recombinant influenza protein vaccine. A "standard of care," as provided herein, refers to a medical or psychological treatment guideline and can be general or specific. "Standard of care" specifies appropriate treatment based on scientific evidence and collaboration between medical professionals involved in the treatment of a given condition. It is the diagnostic and treatment process that a physician/clinician should follow for a certain type of patient, illness or clinical circumstance. A "standard of care dose," as provided herein, refers to the dose of a recombinant or purified influenza protein vaccine, or a live attenuated or inactivated influenza vaccine, that a physician/clinician or other medical professional would administer to a subject to treat or prevent influenza, or an influenza-related condition, while following the standard of care guideline for treating or preventing influenza, or an influenza-related condition.

In some embodiments, the anti-influenza antigenic polypeptide antibody titer produced in a subject administered an effective amount of an influenza RNA vaccine is equivalent to an anti-influenza antigenic polypeptide antibody titer produced in a control subject administered a standard of care dose of a recombinant or purified influenza protein vaccine or a live attenuated or inactivated influenza vaccine.

In some embodiments, an effective amount of an influenza RNA (e.g., mRNA) vaccine is a dose equivalent to an at least 2-fold reduction in a standard of care dose of a recombinant or purified influenza protein vaccine. For example, an effective amount of an influenza RNA vaccine may be a dose equivalent to an at least 3-fold, at least 4-fold, at least 5-fold, at least 6-fold, at least 7-fold, at least 8-fold, at least 9-fold, or at least 10-fold reduction in a standard of care dose of a recombinant or purified influenza protein vaccine. In some embodiments, an effective amount of an influenza RNA vaccine is a dose equivalent to an at least at least 100-fold, at least 500-fold, or at least 1000-fold reduction in a standard of care dose of a recombinant or purified influenza protein vaccine. In some embodiments, an effective amount of an influenza RNA vaccine is a dose equivalent to a 2-, 3-, 4-, 5-, 6-, 7-, 8-, 9-, 10-, 20-, 50-, 100-, 250-, 500-, or 1000-fold reduction in a standard of care dose of a recombinant or purified influenza protein vaccine. In some embodiments, the anti-influenza antigenic polypeptide antibody titer produced in a subject administered an effective amount of an influenza RNA vaccine is equivalent to an anti-influenza antigenic polypeptide antibody titer produced in a control subject administered the standard of care dose of a recombinant or protein influenza protein vaccine or a live attenuated or inactivated influenza vaccine. In some embodiments, an effective amount of an influenza RNA (e.g., mRNA) vaccine is a dose equivalent to a 2-fold to 1000-fold (e.g., 2-fold to 100-fold, 10-fold to 1000-fold) reduction in the standard of care dose of a recombinant or purified influenza protein vaccine, wherein the anti-influenza antigenic polypeptide antibody titer produced in the subject is equivalent to an anti-influenza antigenic polypeptide antibody titer produced in a control subject administered the standard of care dose of a recombinant or purified influenza protein vaccine or a live attenuated or inactivated influenza vaccine.

In some embodiments, the effective amount of an influenza RNA (e.g., mRNA) vaccine is a dose equivalent to a 2 to 1000-, 2 to 900-, 2 to 800-, 2 to 700-, 2 to 600-, 2 to 500-, 2 to 400-, 2 to 300-, 2 to 200-, 2 to 100-, 2 to 90-, 2 to 80-, 2 to 70-, 2 to 60-, 2 to 50-, 2 to 40-, 2 to 30-, 2 to 20-, 2 to 10-, 2 to 9-, 2 to 8-, 2 to 7-, 2 to 6-, 2 to 5-, 2 to 4-, 2 to 3-, 3 to 1000-, 3 to 900-, 3 to 800-, 3 to 700-, 3 to 600-, 3 to 500-, 3 to 400-, 3 to 3 to 00-, 3 to 200-, 3 to 100-, 3 to 90-, 3 to 80-, 3 to 70-, 3 to 60-, 3 to 50-, 3 to 40-, 3 to 30-, 3 to 20-, 3 to 10-, 3 to 9-, 3 to 8-, 3 to 7-, 3 to 6-, 3 to 5-, 3 to 4-, 4 to 1000-, 4 to 900-, 4 to 800-, 4 to 700-, 4 to 600-, 4 to 500-, 4 to 400-, 4 to 4 to 00-, 4 to 200-, 4 to 100-, 4 to 90-, 4 to 80-, 4 to 70-, 4 to 60-, 4 to 50-, 4 to 40-, 4 to 30-, 4 to 20-, 4 to 10-, 4 to 9-, 4 to 8-, 4 to 7-, 4 to 6-, 4 to 5-, 4 to 4-, 5 to 1000-, 5 to 900-, 5 to 800-, 5 to 700-, 5 to 600-, 5 to 500-, 5 to 400-, 5 to 300-, 5 to 200-, 5 to 100-, 5 to 90-, 5 to 80-, 5 to 70-, 5 to 60-, 5 to 50-, 5 to 40-, 5 to 30-, 5 to 20-, 5 to 10-, 5 to 9-, 5 to 8-, 5 to 7-, 5 to 6-, 6 to 1000-, 6 to 900-, 6 to 800-, 6 to 700-, 6 to 600-, 6 to 500-, 6 to 400-, 6 to 300-, 6 to 200-, 6 to 100-, 6 to 90-, 6 to 80-, 6 to 70-, 6 to 60-, 6 to 50-, 6 to 40-, 6 to 30-, 6 to 20-, 6 to 10-, 6 to 9-, 6 to 8-, 6 to 7-, 7 to 1000-, 7 to 900-, 7 to 800-, 7 to 700-, 7 to 600-, 7 to 500-, 7 to 400-, 7 to 300-, 7 to 200-, 7 to 100-, 7 to 90-, 7 to 80-, 7 to 70-, 7 to 60-, 7 to 50-, 7 to 40-, 7 to 30-, 7 to 20-, 7 to 10-, 7 to 9-, 7 to 8-, 8 to 1000-, 8 to 900-, 8 to 800-, 8 to 700-, 8 to 600-, 8 to 500-, 8 to 400-, 8 to 300-, 8 to 200-, 8 to 100-, 8 to 90-, 8 to 80-, 8 to 70-, 8 to 60-, 8 to 50-, 8 to 40-, 8 to 30-, 8 to 20-, 8 to 10-, 8 to 9-, 9 to 1000-, 9 to 900-, 9 to 800-, 9 to 700-, 9 to 600-, 9 to 500-, 9 to 400-, 9 to 300-, 9 to 200-, 9 to 100-, 9 to 90-, 9 to 80-, 9 to 70-, 9 to 60-, 9 to 50-, 9 to 40-, 9 to 30-, 9 to 20-, 9 to 10-, 10 to 1000-, 10 to 900-, 10 to 800-, 10 to 700-, 10 to 600-, 10 to 500-, 10 to 400-, 10 to 300-, 10 to 200-, 10 to 100-, 10 to 90-, 10 to 80-, 10 to 70-, 10 to 60-, 10 to 50-, 10 to 40-, 10 to 30-, 10 to 20-, 20 to 1000-, 20 to 900-, 20 to 800-, 20 to 700-, 20 to 600-, 20 to 500-, 20 to 400-, 20 to 300-, 20 to 200-, 20 to 100-, 20 to 90-, 20 to 80-, 20 to 70-, 20 to 60-, 20 to 50-, 20 to 40-, 20 to 30-, 30 to 1000-, 30 to 900-, 30 to 800-, 30 to 700-, 30 to 600-, 30 to 500-, 30 to 400-, 30 to 300-, 30 to 200-, 30 to 100-, 30 to 90-, 30 to 80-, 30 to 70-, 30 to 60-, 30 to 50-, 30 to 40-, 40 to 1000-, 40 to 900-, 40 to 800-, 40 to 700-, 40 to 600-, 40 to 500-, 40 to 400-, 40 to 300-, 40 to 200-, 40 to 100-, 40 to 90-, 40 to 80-, 40 to 70-, 40 to 60-, 40 to 50-, 50 to 1000-, 50 to 900-, 50 to 800-, 50 to 700-, 50 to 600-, 50 to 500-, 50 to 400-, 50 to 300-, 50 to 200-, 50 to 100-, 50 to 90-, 50 to 80-, 50 to 70-, 50 to 60-, 60 to 1000-, 60 to 900-, 60 to 800-, 60 to 700-, 60 to 600-, 60 to 500-, 60 to 400-, 60 to 300-, 60 to 200-, 60 to 100-, 60 to 90-, 60 to 80-, 60 to 70-, 70 to 1000-, 70 to 900-, 70 to 800-, 70 to 700-, 70 to 600-, 70 to 500-, 70 to 400-, 70 to 300-, 70 to 200-, 70 to 100-, 70 to 90-, 70 to 80-, 80 to 1000-, 80 to 900-, 80 to 800-, 80 to 700-, 80 to 600-, 80 to 500-, 80 to 400-, 80 to 300-, 80 to 200-, 80 to 100-, 80 to 90-, 90 to 1000-, 90 to 900-, 90 to 800-, 90 to 700-, 90 to 600-, 90 to 500-, 90 to 400-, 90 to 300-, 90 to 200-, 90 to 100-, 100 to 1000-, 100 to 900-, 100 to 800-, 100 to 700-, 100 to 600-, 100 to 500-, 100 to 400-, 100 to 300-, 100 to 200-, 200 to 1000-, 200 to 900-, 200 to 800-, 200 to 700-, 200 to 600-, 200 to 500-, 200 to 400-, 200 to 300-, 300 to 1000-, 300 to 900-, 300 to 800-, 300 to 700-, 300 to 600-, 300 to 500-, 300 to 400-, 400 to 1000-, 400 to 900-, 400 to 800-, 400 to 700-, 400 to 600-, 400 to 500-, 500 to 1000-, 500 to 900-, 500 to 800-, 500 to 700-, 500 to 600-, 600 to 1000-, 600 to 900-, 600 to 800-, 600 to 700-, 700 to 1000-, 700 to 900-, 700 to 800-, 800 to 1000-, 800 to 900-, or 900 to 1000-fold reduction in the standard of care dose of a recombinant influenza protein vaccine. In some embodiments, such as the foregoing, the anti-influenza antigenic polypeptide antibody titer produced in the subject is equivalent to an anti-influenza antigenic polypeptide antibody titer produced in a control subject administered the standard of care dose of a recombinant or purified influenza protein vaccine or a live attenuated or inactivated influenza vaccine. In some embodiments, the effective amount is a dose equivalent to (or equivalent to an at least) 2-, 3-, 4-, 5-, 6-, 7-, 8-, 9-, 10-, 20-, 30-, 40-, 50-, 60-, 70-, 80-, 90-, 100-, 110-, 120-, 130-, 140-, 150-, 160-, 170-, 1280-, 190-, 200-, 210-, 220-, 230-, 240-, 250-, 260-, 270-, 280-, 290-, 300-, 310-, 320-, 330-, 340-, 350-, 360-, 370-, 380-, 390-, 400-, 410-, 420-, 430-, 440-, 450-, 4360-, 470-, 480-, 490-, 500-, 510-, 520-, 530-, 540-, 550-, 560-, 5760-, 580-, 590-, 600-, 610-, 620-, 630-, 640-, 650-, 660-, 670-, 680-, 690-, 700-, 710-, 720-, 730-, 740-, 750-, 760-, 770-, 780-, 790-, 800-, 810-, 820-, 830-, 840-, 850-, 860-, 870-, 880-, 890-, 900-, 910-, 920-, 930-, 940-, 950-, 960-, 970-, 980-, 990-, or 1000-fold reduction in the standard of care dose of a recombinant influenza protein vaccine. In some embodiments, such as the foregoing, an anti-influenza antigenic polypeptide antibody titer produced in the subject is equivalent to an anti-influenza antigenic polypeptide antibody titer produced in a control subject administered the standard of care dose of a recombinant or purified influenza protein vaccine or a live attenuated or inactivated influenza vaccine.

In some embodiments, the effective amount of an influenza RNA (e.g., mRNA) vaccine is a total dose of 50-1000 µg. In some embodiments, the effective amount of an influenza RNA (e.g., mRNA) vaccine is a total dose of 50-1000, 50-900, 50-800, 50-700, 50-600, 50-500, 50-400, 50-300, 50-200, 50-100, 50-90, 50-80, 50-70, 50-60, 60-1000, 60-900, 60-800, 60-700, 60-600, 60-500, 60-400, 60-300, 60-200, 60-100, 60-90, 60-80, 60-70, 70-1000, 70-900, 70-800, 70-700, 70-600, 70-500, 70-400, 70-300, 70-200, 70-100, 70-90, 70-80, 80-1000, 80-900, 80-800, 80-700, 80-600, 80-500, 80-400, 80-300, 80-200, 80-100, 80-90, 90-1000, 90-900, 90-800, 90-700, 90-600, 90-500, 90-400, 90-300, 90-200, 90-100, 100-1000, 100-900, 100-800, 100-700, 100-600, 100-500, 100-400, 100-300, 100-200, 200-1000, 200-900, 200-800, 200-700, 200-600, 200-500, 200-400, 200-300, 300-1000, 300-900, 300-800, 300-700, 300-600, 300-500, 300-400, 400-1000, 400-900, 400-800, 400-700, 400-600, 400-500, 500-1000, 500-900, 500-800, 500-700, 500-600, 600-1000, 600-900, 600-900, 600-700, 700-1000, 700-900, 700-800, 800-1000, 800-900, or 900-1000 µg. In some embodiments, the effective amount of an influenza RNA (e.g., mRNA) vaccine is a total dose of 50, 100, 150, 200, 250, 300, 350, 400, 450, 500, 550, 600, 650, 700, 750, 800, 850, 900, 950 or 1000 µg. In some embodiments, the effective amount is a dose of 25-500 µg administered to the subject a total of two times. In some embodiments, the effective amount of an influenza RNA (e.g., mRNA) vaccine is a dose of 25-500, 25-400, 25-300, 25-200, 25-100, 25-50, 50-500, 50-400, 50-300, 50-200, 50-100, 100-500, 100-400, 100-300, 100-200, 150-500, 150-400, 150-300, 150-200, 200-500, 200-400, 200-300, 250-500, 250-400, 250-300, 300-500, 300-400, 350-500, 350-400, 400-500 or 450-500 µg administered to the subject a total of two times. In some embodiments, the effective amount of an influenza RNA (e.g., mRNA) vaccine is a total dose of 25, 50, 100, 150, 200, 250, 300, 350, 400, 450, or 500 µg administered to the subject a total of two times.

In some embodiments, the antigen specific immune response induced by the influenza RNA vaccines in a subject is the production of antibodies specific to an anti-influenza antigenic polypeptide. In some embodiments, such antibodies are capable of neutralizing influenza in an infected host. In some embodiments, the antigen specific immune response induced by the influenza RNA vaccines in a subject is antigen-specific T-cell response. Such T-cell response may provide immunity to the immunized animal (e.g., mice or human) against fusion influenza infections.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

Example 1. mRNA for H10N8 Influenza

Figure 6:
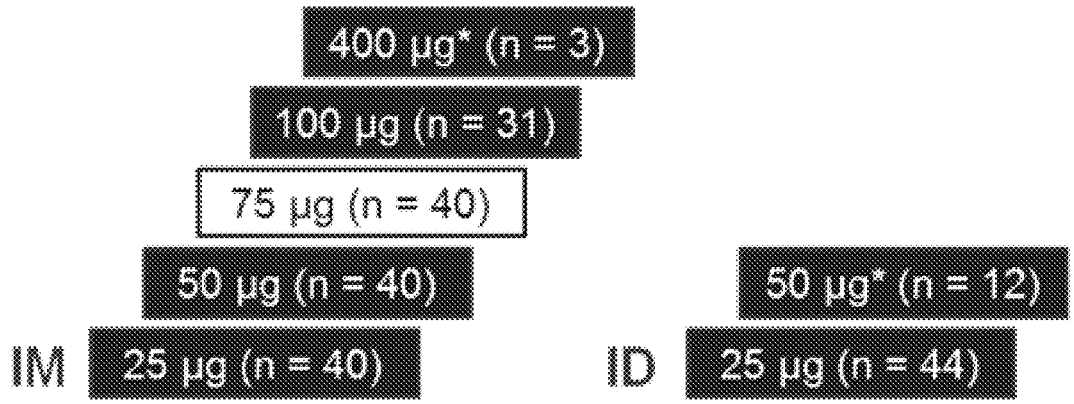
FIG. 6: A schematic showing the dose-escalation by administration type during a phase 1 trial. Black boxes indicate a cohort that was completed or closed. White boxes indicate a cohort that continues to enroll. An asterisk is used to depict cohorts that received a prime dose only and were later discontinued.

A phase I clinical trial was conducted to test an mRNA vaccine for H10N8 influenza. The schematic FIG. 6 shows the dose-escalation by administration type during a phase 1 trial. Black boxes indicate a cohort that was completed or closed. White boxes indicate a cohort that continues to enroll. An asterisk is used to depict cohorts that received a prime dose only and were later discontinued.

mRNA encoding full-length, membrane-bound hemagglutinin was produced and used in human subjects in a Phase 1 trial. Dose-escalating was performed by administration type, intramuscular (IM) and intradermal (ID) cohorts, at a placebo controlled rate of 3:1. Subjects received 2 doses at day 1 and at day 22. 400 µg were given to the IM group, while the ID group received 50 µg due to safety concerns.

The HAI titers and microneutralization (MN) were measured at day 43. The protocol was later amended to include 75 µg for the elderly cohort.

Figure 2:
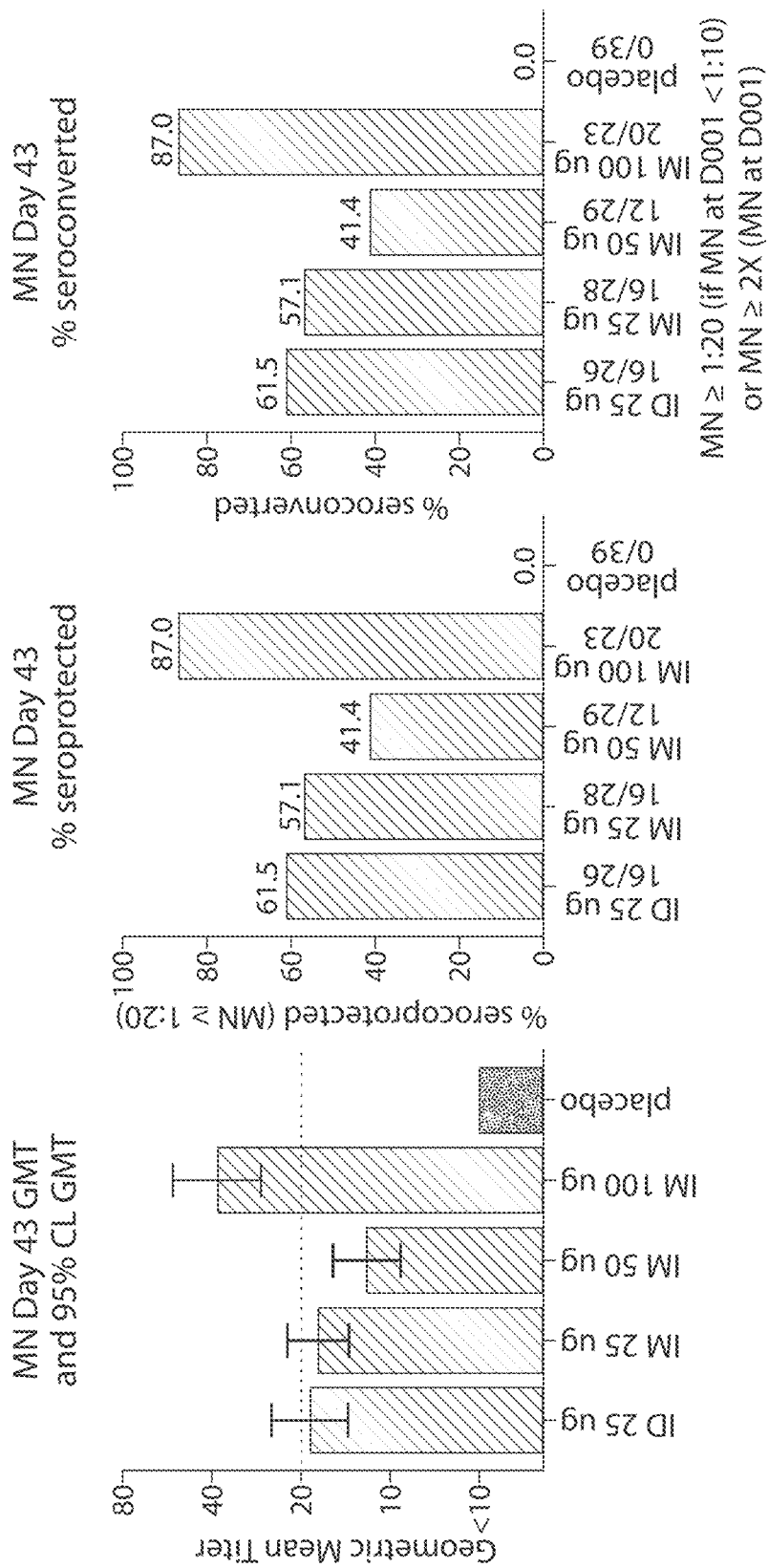
FIG. 2: Graphs show the results of the phase 1 trial in the 100 μg intramuscular (IM) cohort based on microneuralizations (MN).

It was expected that HAI titers of 1:40 or HAI increases of 4× from baseline would be more protective. The unblinded data from the phase 1 trial reported that up to 100% of the IM 100 µg cohort achieved a 1:40 titer, while 78% of this cohort had a 4× increase from baseline (FIG. 1). It was also thought that microneutralizations of 1:20 or an MN increase of 2× from baseline would be protective. The unblinded data from the phase 1 trial reported that 87% of the IM 100 µg cohort achieved a 1:20 or 2× MN increase from baseline (FIG. 2).

Example 2. mRNA for H7N9 Influenza

Figure 7:
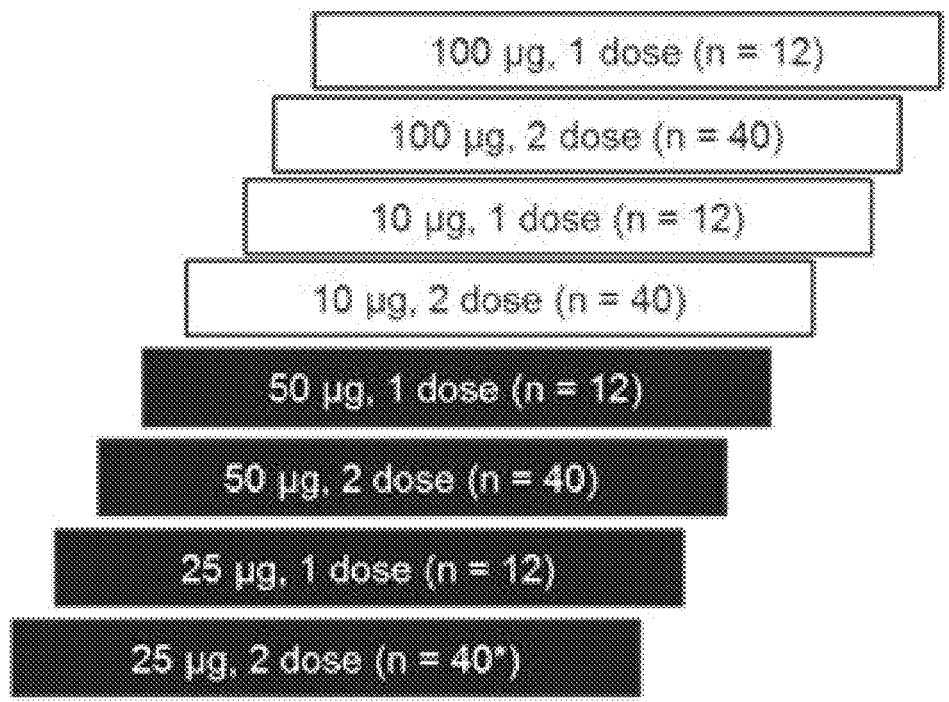
FIG. 7: A schematic showing the dose-escalation on the intramuscular (IM) cohort during a phase 1 trial. Black boxes indicate a cohort that was completed or closed. White boxes indicate a cohort that continues to enroll. An asterisk is used to depict a cohort where 3 participants missed a dose.

A phase I clinical trial was conducted to test an mRNA vaccine for H7N9 influenza. The schematic in FIG. 7 shows the dose-escalation on the intramuscular (IM) cohort during a phase 1 trial. Black boxes indicate a cohort that was completed or closed. White boxes indicate a cohort that continues to enroll. An asterisk is used to depict a cohort where 3 participants missed a dose.

mRNA encoding full-length, membrane-bound hemagglutinin was tested in a Phase 1 trial. Dose-escalating was performed on the intramuscular (IM) cohort at a placebo controlled rate of 3:1. Subjects received a prime dose at day 1 and a booster at day 22. Finally, HAI titers and microneutralization (MN) levels were measured at day 43. The protocol was later amended to include a 10 µg cohort and to remove the 200 µg cohort.

Figure 3:
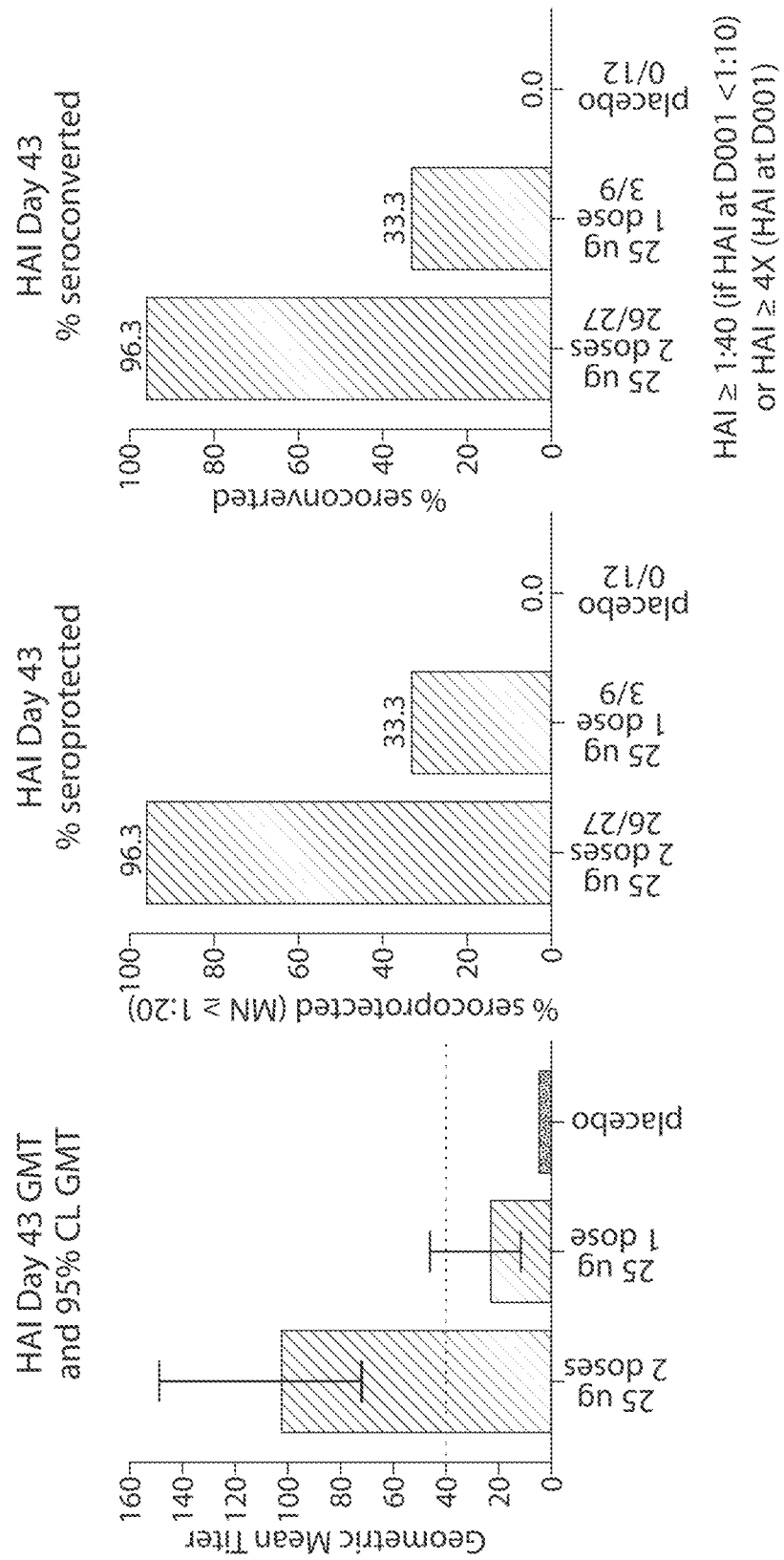
FIG. 3: Graphs show the results of the phase 1 trial in the 125 μg intramuscular (IM) 2 dose cohort based on hemagglutination inhibition (HAI).
Figure 4:
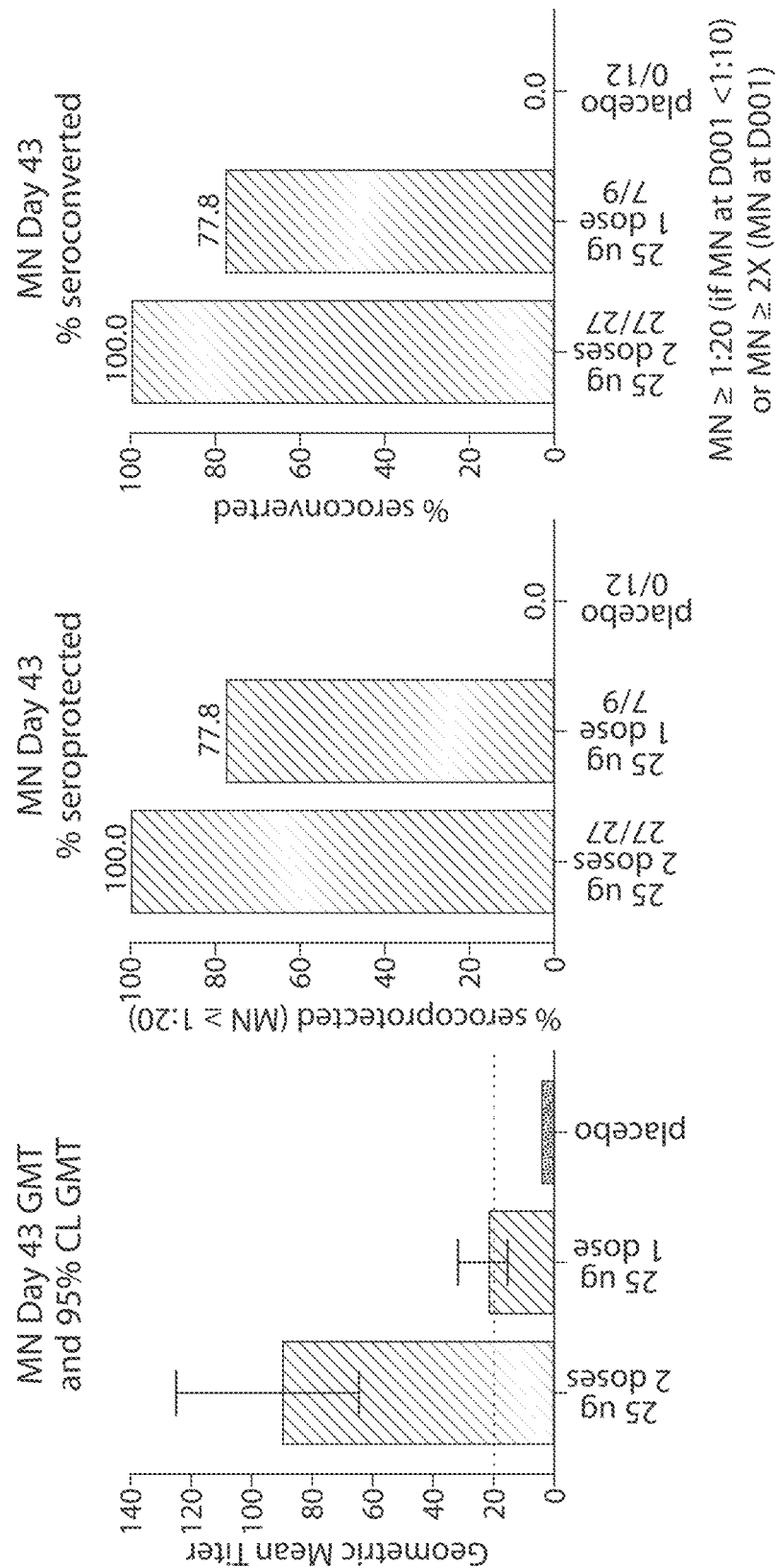
FIG. 4: Graphs show the results of the phase 1 trial in the 100 μg intramuscular (IM) cohort based on microneuralizations (MN).

It was expected that HAI titers of 1:40 or an HAI increase of 4× from baseline would be more protective. The unblinded data from the phase 1 trial reported that up to 96% (26 out of 27) of subjects of the IM 25 µg 2 dose cohort showed an increase in protection based on HAI. Three out of nine subjects in the single dose cohort also achieved this same result (FIG. 3). It was also theorized that microneutralizations of 1:20 or an MN increase of 2× from baseline would to be protective. The unblinded data from the phase 1 trial reported that up to 100% of the IM 25 µg 2 dose cohort achieved a 1:20 or 2× MN increase from baseline. Seven out of nine subjects in the single dose cohort also achieved this same result (FIG. 4).

Table 1 shows comparison data of competitors with the percentage of individuals with HAI or MN greater than 40 at day 21 (day 14 for Novarax) after the second dose.

TABLE 1

Comparison to Competitor Data

| Company | Adjuvant | HAI | MN |
|---|---|---|---|
| Novartis | MF59 | 52 | 78 |
| Novavax | Iscomatrix | 81 | N/T |
| GSK | AS03 | 96 | 96 |
| Constructs of the invention | | 96 | 100 |

Example 3. Long Term mRNA Vaccine for H10N8 Influenza

Figure 5:
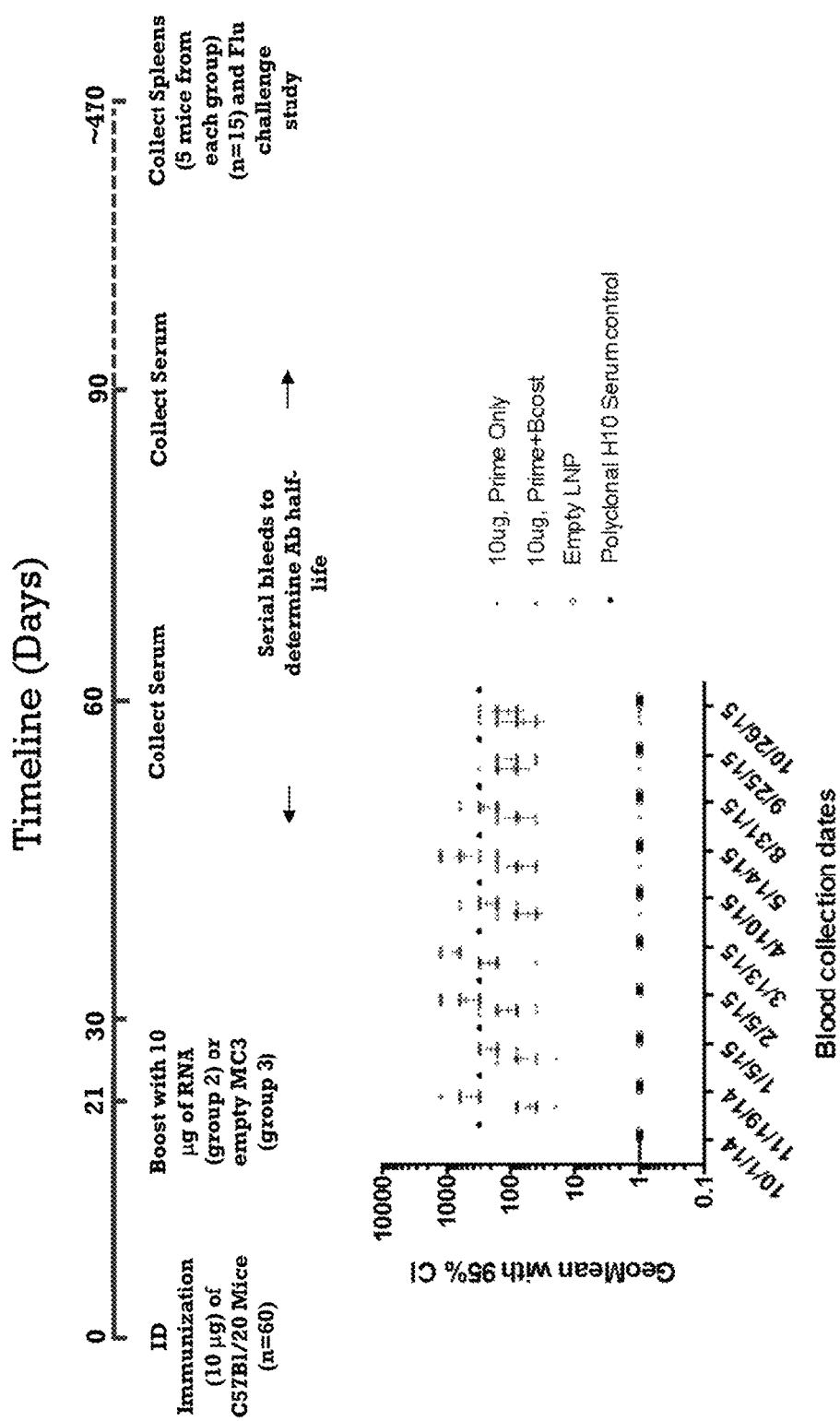
FIG. 5: Time line of long term vaccination study and graph showing the results.

In this study, mice were vaccinated with an mRNA H10N8 influenza vaccine and observed for over a year. Blood was collected monthly to study the longevity of the HAI response. The results are shown in FIG. 5. HAI titers remained relatively constant for more than nine months. Some decline can be seen at around 11 months. However these mice are beginning to die at that point from natural causes. The life span of a mouse is about 12-16 mo. The results demonstrate, quite unexpectedly, that the protective effect of the mRNA vaccine lasted through the mouse lifetime.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc. As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc. Each possibility represents a separate embodiment of the present invention.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

SEQUENCE LISTING

```
Sequence total quantity: 23
SEQ ID NO: 1            moltype = AA  length = 560
FEATURE                 Location/Qualifiers
source                  1..560
                        mol_type = protein
                        note = Influenza A virus
                        organism = unidentified
SEQUENCE: 1
MNTQILVFAL IAIIPTNADK ICLGHHAVSN GTKVNTLTER GVEVVNATET VERTNIPRIC  60
SKGKKTVDLG QCGLLGTITG PPQCDQFLEF SADLIIERRE GSDVCYPGKF VNEEALRQIL  120
RESGGIDKEA MGFTYSGIRT NGATSACRRS GSSFYAEMKW LLSNTDNAAF PQMTKSYKNT  180
RKSPALIVWG IHHSVSTAEQ TKLYGSGNKL VTVGSSNYQQ SFVPSPGARP QVNGQSGRID  240
FHWLMLNPND TVTFSFNGAF IAPDRASFLR GKSMGIQSGV QVDANCEGDC YHSGGTIISN  300
LPFQNIDSRA VGKCPRYVKQ RSLLLATGMK NVPEIPKGRG LFGAIAGFIE NGWEGLIDGW  360
YGFRHQNAQG EGTAADYKST QSAIDQITGK LNRLIEKTNQ QFELIDNEFN EVEKQIGNVI  420
NWTRDSITEV WSYNAELLVA MENQHTIDLA DSEMDKLYER VKRQLRENAE EDGTGCFEIF  480
HKCDDDCMAS IRNNTYDHSK YREEAMQNRI QIDPVKLSSG YKDVILWFSF GASCFILLAI  540
VMGLVFICVK NGNMRCTICI                                              560

SEQ ID NO: 2            moltype = RNA  length = 1953
FEATURE                 Location/Qualifiers
misc_feature            1..1953
                        note = Synthetic Polynucleotide
misc_feature            1
                        note = Modified by 7MeGpppG2'OMe
misc_feature            1953
                        note = Modified by OH
source                  1..1953
                        mol_type = other RNA
                        organism = synthetic construct
SEQUENCE: 2
ggaaataaga gagaaaagaa gagtaagaag aaatataaga gccaccatgt acaaaatcgt  60
cgtcattatc gcattgctgg gcgctgtcaa gggactcgac aagatctgtc tcggacacca  120
cgcggtggct aacggaacca tcgtcaagac cctgactaac gagcaggaag aagtgaccaa  180
cgccaccgaa actgtggaat ccaccgggat caacagattg tgcatgaagg gtcggaagca  240
caaggatctg ggaaactgcc acccgattgg aatgctcatc ggcaccccgg catgcgatct  300
gcatctgact gggatgtggg ataccttat cgagcgggaa aacgcgatcg catactgtta  360
ccccggtgcc accgtgaacg tggaggcgct cagacagaag attatggagt caggcggcat  420
caacaagatt tccacgggct tcacctacgg gtcctccatt aactccgccg gtaccactcg  480
ggcctgcatg cggaacggag ggaactcctt ttacgccgag ctcaagtggc ttgtgtcaaa  540
atccaaggga cagaatttcc cccaaaccac caacacctat aggaacaccg acaccgccga  600
acatctcatt atgtggggca tccatcaccc ttcgagcaca caggagaaga atgacctcta  660
cggcacccag tcgctgagca tctccgtggg ctcatcgacc tatcgcaaca acttcgtgcc  720
tgtggtcggc gcccgacctc aagtcaacgg acagtccgga cgcattgact tccattggac  780
tctggtgcaa ccgggagaca acatcacttt ctcccacaac ggcggactga ttgccccaag  840
```

-continued

```
ccgcgtgtca aagctgatcg gtagagggct gggtattcag tcggatgctc ccatcgataa  900
caactgcgaa tccaagtgct tttggagagg cggctccatc aatactcggc tgccgtttca  960
gaacctgagc ccgaggaccg tggggcagtg cccaaaatac gtgaatcgcc ggtcactgat  1020
gctggcgacc ggaatgagga acgtgcctga actcatccag ggacgggggc tgttcggcgc  1080
catcgccggc ttcctggaaa acggatggga gggaatggtg gacggttggt acggcttccg  1140
ccaccaaaac gcccagggaa ctggacaggc cgccgactac aagtccacac aggccgcaat  1200
agaccagatc actgggaagc tcaaccgcct tgtggaaaag actaacactg aattcgagtc  1260
gatcgagtct gagttctccg agatcgaaca ccagattggg aacgtgatca actggacgaa  1320
ggactccatt accgacatct ggacctacca ggcggaactg ctcgtggcga tggagaacca  1380
gcacactatc gacatggccg actccgagat gctgaatctg tacgaacgcg tgcggaagca  1440
actgagacaa aacgctgaag aagatggaaa gggttgtttc gagatctacc acgcctgcga  1500
cgacagctgc atggaaagca ttaggaacaa tacctacgac cactcgcagt accgggagga  1560
ggcccttctg aaccggctga acattaaccc cgtgaccttg agctccggct acaaggacat  1620
catcctgtgg ttctcgtttg gagccagctg cttcgtgctg ctggccgtcg tgatgggatt  1680
gttcttcttc tgcctgaaaa acggaaacat gcgctgcacc atctgtattt gataataggc  1740
tggagcctcg gtggccatgc ttcttgcccc ttgggcctcc ccccagcccc tcctcccctt  1800
cctgcacccg tacccccgtg gtctttgaat aaagtctgag tgggcggcaa aaaaaaaaaa  1860
aaaaaaaaaa aaaaaaaaaa aaaaaaaaaa aaaaaaaaaa aaaaaaaaaa aaaaaaaaaa  1920
aaaaaaaaaa aaaaaaaaaa aaaaaaaatc tag                                1953

SEQ ID NO: 3            moltype = DNA  length = 1683
FEATURE                 Location/Qualifiers
misc_feature            1..1683
                        note = Synthetic Polynucleotide
source                  1..1683
                        mol_type = other DNA
                        organism = synthetic construct
SEQUENCE: 3
atgtacaaaa tcgtcgtcat tatcgcattg ctgggcgctg tcaagggact cgacaagatc  60
tgtctcggac accacgcggt ggctaacgga accatcgtca agaccctgac taacgagcag  120
gaagaagtga ccaacgccac cgaaactgtg gaatccaccg ggatcaacag attgtgcatg  180
aagggtcgga agcacaagga tctgggaaac tgccacccga ttggaatgct catcggcacc  240
ccggcatgcg atctgcatct gactgggatg tgggataccc ttatcgagcg ggaaaacgcg  300
atcgcatact gttaccccgg tgccaccgtg aacgtggagg cgctcagaca gaagattatg  360
gagtcaggcg gcatcaacaa gatttccacg ggcttcacct acgggtcctc cattaactcc  420
gccggtacca ctcgggcctg catgcggaac ggagggaact ccttttacgc cgagctcaag  480
tggcttgtgt caaaatccaa gggacagaat ttcccccaaa ccaccaacac ctataggaac  540
accgacaccg ccgaacatct cattatgtgg ggcatccatc acccttcgag cacacaggag  600
aagaatgacc tctacggcac ccagtcgctg agcatctccg tgggctcatc gacctatcgc  660
aacaacttcg tgcctgtggt cggcgcccga cctcaagtca acggacagtc cggacgcatt  720
gacttccatt ggactctggt gcaaccggga gacaacatca ctttctccca caacggcgga  780
ctgattgccc caagccgcgt gtcaaagctg atcggtagag ggctgggtat tcagtcggat  840
gctcccatcg ataacaactg cgaatccaag tgcttttgga gaggcggctc catcaatact  900
cggctgccgt ttcagaacct gagcccgagg accgtggggc agtgcccaaa atacgtgaat  960
cgccggtcac tgatgctggc gaccggaatg aggaacgtgc ctgaactcat ccagggacgg  1020
gggctgttcg gcgccatcgc cggcttcctg gaaaacggat gggagggaat ggtggacggt  1080
tggtacggct tccgccacca aaacgcccag ggaactggac aggccgccga ctacaagtcc  1140
acacaggccg caatagacca gatcactggg aagctcaacc gccttgtgga aaagactaac  1200
actgaattcg agtcgatcga gtctgagttc tccgagatcg aacaccagat tgggaacgtg  1260
atcaactgga cgaaggactc cattaccgac atctggacct accaggcgga actgctcgtg  1320
gcgatggaga accagcacac tatcgacatg gccgactccg agatgctgaa tctgtacgaa  1380
cgcgtgcgga agcaactgag acaaaacgct gaagaagatg gaaagggttg tttcgagatc  1440
taccacgcct gcgacgacag ctgcatggaa agcattagga acaataccta cgaccactcg  1500
cagtaccggg aggaggccct tctgaaccgg ctgaacatta accccgtgac cttgagctcc  1560
ggctacaagg acatcatcct gtggttctcg tttggagcca gctgcttcgt gctgctggcc  1620
gtcgtgatgg gattgttctt cttctgcctg aaaaacggaa acatgcgctg caccatctgt  1680
att                                                                 1683

SEQ ID NO: 4            moltype = AA  length = 561
FEATURE                 Location/Qualifiers
source                  1..561
                        mol_type = protein
                        note = Influenza A virus
                        organism = unidentified
SEQUENCE: 4
MYKIVVIIAL LGAVKGLDKI CLGHHAVANG TIVKTLTNEQ EEVTNATETV ESTGINRLCM  60
KGRKHKDLGN CHPIGMLIGT PACDLHLTGM WDTLIERENA IAYCYPGATV NVEALRQKIM  120
ESGGINKIST GFTYGSSINS AGTTRACMRN GGNSFYAELK WLVSKSKGQN FPQTTNTYRN  180
TDTAEHLIMW GIHHPSSTQE KNDLYGTQSL SISVGSSTYR NNFVPVVGAR PQVNGQSGRI  240
DFHWTLVQPG DNITFSHNGG LIAPSRVSKL IGRGLGIQSD APIDNNCESK CFWRGGSINT  300
RLPFQNLSPR TVGQCPKYVN RRSLMLATGM RNVPELIQGR GLFGAIAGFL ENGWEGMVDG  360
WYGFRHQNAQ GTGQAADYKS TQAAIDQITG KLNRLVEKTN TEFESIESEF SEIEHQIGNV  420
INWTKDSITD IWTYQAELLV AMENQHTIDM ADSEMLNLYE RVRKQLRQNA EEDGKGCFEI  480
YHACDDSCME SIRNNTYDHS QYREEALLNR LNINPVTLSS GYKDIILWFS FGASCFVLLA  540
VVMGLFFFCL KNGNMRCTIC I                                             561

SEQ ID NO: 5            moltype = DNA  length = 1891
FEATURE                 Location/Qualifiers
misc_feature            1..1891
```

```
                        note = Synthetic Polynucleotide
source                  1..1891
                        mol_type = other DNA
                        organism = synthetic construct
SEQUENCE: 5
tcaagctttt ggaccctcgt acagaagcta atacgactca ctataggaa ataagagaga      60
aaagaagagt aagaagaaat ataagagcca ccatgaatac ccagattctc gtgttcgccc    120
tcatcgctat catcccaacc aatgccgaca agatctgctt gggtcatcat gcggtgtcga    180
acggaaccaa ggtcaacacc ctgaccgagc ggggagtgga agtggtcaac gctactgaaa    240
cggtggaaag gactaatatc ccacgcatct gctcaaaggg aaagaaaact gtggatctcg    300
gacagtgtgg acttctgggg accatcacgg gtccaccgca atgcgatcag tttctggagt    360
tcagcgcaga tctgatcatc gagcgcagag aagggtccga cgtttgttac cctgaaagt    420
tcgtgaacga agaggcactg cgccaaatct gcgggagag cggcggcatt gacaaagagg    480
ccatgggatt cacctactcg ggtattcgca ctaacggtgc cacttctgcg tgccggcgtt    540
ccgggtcctc cttctatgcc gagatgaagt ggctcctgtc gaacaccgac aacgcagctt    600
ttccgcaaat gactaagtcc tacaaaaaca ctagaaagtc gccggcactg atcgtctggg    660
gaatccatca ctccgtgtct actgcggagc aaactaagct gtacggcagc ggaaacaagc    720
tcgtgaccgt cggttcatcg aactaccagc agagcttttgt gccaagcccc ggagcgaggc    780
cccaggtcaa cgggcagagc ggacgcatcg acttccactg gctgatgctc aatccgaatg    840
acaccgtgac cttctcgttc aatgcgcct tcatcgcacc tgaccgcgcc agcttcctga    900
gaggaaagtc aatgggcata cagtcgggcg tccaagtgga tgccaactgc gagggagact    960
gctatcactc cggcggaacc atcatctcca atttgccgtt tcaaaacatc gactcgcgcg   1020
cagtgggaaa gtgtccgcga tacgtgaagc agagatcact gctgctggcc actgggatga   1080
agaacgtgcc tgaaatcccg aaaggaaggg ggttgttcgg cgctattgcg ggcttcatcg   1140
aaaacgatg ggaggggctc atcgatggtt ggtacggatt caggcaccag aacgcgcagg   1200
gggaaggaac ggccgctgat tacaagtcaa ctcaatcggc cattgaccaa atcactggca   1260
aactgaatcg cctgatcgaa aagaccaatc agcagtttga gttgatcgac aacgaattca   1320
acgaagtgga gaaacagatt ggcaatgtca tcaattggac cagagatagc atcacggaag   1380
tctggtcgta caacgccgaa ctcctggttg cgatggaaaa tcaacacacc atcgacctgg   1440
ccgactccga aatggacaaa ctctacgagc gggtcaaacg ccagctgcgc gaaaacgcag   1500
aagaagatgg aaccggatgc ttcgagatct ttcataagtg cgacgacgat tgcatggcca   1560
gcatccggaa caatacctac gatcactcca gtaccggga ggaagcgatg caaaatcgga   1620
tccagattga cccggtcaaa ctgtcgtcag gctacaagga tgtgatcctt tggttctcat   1680
tcggagcgtc ctgttttatc cttctggcta ttgtgatggg cctggtgttc atctgcgtga   1740
agaacgaaa catgcgctgc actatctgca tctgataata ggctggagcc tcggtggcca   1800
tgcttcttgc cccttgggcc tccccccagc ccctcctccc cttcctgcac ccgtaccccc   1860
gtggtctttg aataaagtct gagtgggcgg c                                  1891

SEQ ID NO: 6            moltype = RNA    length = 1891
FEATURE                 Location/Qualifiers
misc_feature            1..1891
                        note = Synthetic Polynucleotide
source                  1..1891
                        mol_type = other RNA
                        organism = synthetic construct
SEQUENCE: 6
tcaagctttt ggaccctcgt acagaagcta atacgactca ctataggaa ataagagaga      60
aaagaagagt aagaagaaat ataagagcca ccatgaatac ccagattctc gtgttcgccc    120
tcatcgctat catcccaacc aatgccgaca agatctgctt gggtcatcat gcggtgtcga    180
acggaaccaa ggtcaacacc ctgaccgagc ggggagtgga agtggtcaac gctactgaaa    240
cggtggaaag gactaatatc ccacgcatct gctcaaaggg aaagaaaact gtggatctcg    300
gacagtgtgg acttctgggg accatcacgg gtccaccgca atgcgatcag tttctggagt    360
tcagcgcaga tctgatcatc gagcgcagag aagggtccga cgtttgttac cctgaaagt    420
tcgtgaacga agaggcactg cgccaaatct gcgggagag cggcggcatt gacaaagagg    480
ccatgggatt cacctactcg ggtattcgca ctaacggtgc cacttctgcg tgccggcgtt    540
ccgggtcctc cttctatgcc gagatgaagt ggctcctgtc gaacaccgac aacgcagctt    600
ttccgcaaat gactaagtcc tacaaaaaca ctagaaagtc gccggcactg atcgtctggg    660
gaatccatca ctccgtgtct actgcggagc aaactaagct gtacggcagc ggaaacaagc    720
tcgtgaccgt cggttcatcg aactaccagc agagctttgt gccaagcccc ggagcgaggc    780
cccaggtcaa cgggcagagc ggacgcatcg acttccactg gctgatgctc aatccgaatg    840
acaccgtgac cttctcgttc aatgcgcct tcatcgcacc tgaccgcgcc agcttcctga    900
gaggaaagtc aatgggcata cagtcgggcg tccaagtgga tgccaactgc gagggagact    960
gctatcactc cggcggaacc atcatctcca atttgccgtt tcaaaacatc gactcgcgcg   1020
cagtgggaaa gtgtccgcga tacgtgaagc agagatcact gctgctggcc actgggatga   1080
agaacgtgcc tgaaatcccg aaaggaaggg ggttgttcgg cgctattgcg ggcttcatcg   1140
aaaacgatg ggaggggctc atcgatggtt ggtacggatt caggcaccag aacgcgcagg   1200
gggaaggaac ggccgctgat tacaagtcaa ctcaatcggc cattgaccaa atcactggca   1260
aactgaatcg cctgatcgaa aagaccaatc agcagtttga gttgatcgac aacgaattca   1320
acgaagtgga gaaacagatt ggcaatgtca tcaattggac cagagatagc atcacggaag   1380
tctggtcgta caacgccgaa ctcctggttg cgatggaaaa tcaacacacc atcgacctgg   1440
ccgactccga aatggacaaa ctctacgagc gggtcaaacg ccagctgcgc gaaaacgcag   1500
aagaagatgg aaccggatgc ttcgagatct ttcataagtg cgacgacgat tgcatggcca   1560
gcatccggaa caatacctac gatcactcca gtaccggga ggaagcgatg caaaatcgga   1620
tccagattga cccggtcaaa ctgtcgtcag gctacaagga tgtgatcctt tggttctcat   1680
tcggagcgtc ctgttttatc cttctggcta ttgtgatggg cctggtgttc atctgcgtga   1740
agaacgaaa catgcgctgc actatctgca tctgataata ggctggagcc tcggtggcca   1800
tgcttcttgc cccttgggcc tccccccagc ccctcctccc cttcctgcac ccgtaccccc   1860
gtggtctttg aataaagtct gagtgggcgg c                                  1891
```

| SEQ ID NO: 7 | moltype = RNA   length = 1680 |
|---|---|
| FEATURE | Location/Qualifiers |
| misc_feature | 1..1680 |
| | note = Synthetic Polynucleotide |
| source | 1..1680 |
| | mol_type = other RNA |
| | organism = synthetic construct |

SEQUENCE: 7

```
atgaataccc agattctcgt gttcgccctc atcgctatca tcccaaccaa tgccgacaag   60
atctgcttgg gtcatcatgc ggtgtcgaac ggaaccaagg tcaacaccct gaccgagcgg  120
ggagtggaag tggtcaacgc tactgaaacg gtggaaagga ctaatatccc acgcatctgc  180
tcaaagggaa agaaaactgt ggatctcgga cagtgtggac ttctggggac catcacgggt  240
ccaccgcaat gcgatcagtt tctggagttc agcgcagatc tgatcatcga gcgcagagaa  300
gggtccgacg tttgttaccc tggaaagttc gtgaacgaag aggcactgcg ccaaatcttg  360
cgggagagcg gcgcattga caaagaggcc atgggattca cctactcggg tattcgcact  420
aacggtgcca cttctgcgtg ccggcgttcc gggtcctcct tctatgccga gatgaagtgg  480
ctcctgtcga acaccgacaa cgcagctttt ccgcaaatga ctaagtccta caaaaacact  540
agaaagtcgc cggcactgat cgtctgggga atccatcact ccgtgtctac tgccgagcaa  600
actaagctgt acggcagcgg aaacaagctc gtgaccgtcg gttcatcgaa ctaccagcag  660
agctttgtgc caagcccggg agcgaggccc aggtcaacg ggcagagcgg acgcatcgac  720
ttccactggc tgatgctcaa tccgaatgac accgtgacct tctcgttcaa tggcgccttc  780
atcgcacctg accgcgccag cttcctgaga ggaaagtcaa cgcgcataca gtcgggcgtc  840
caagtggatg ccaactgcga gggagactgc tatcactccg gcggaaccat catctccaat  900
ttgccgtttc aaaacatcga ctcgcgcgca gtgggaaagt gtccgcgata cgtgaagcag  960
agatcactgc tgctggccac tgggatgaag aacgtgcctg aaatcccgaa aggaaggggg 1020
ttgttcggcg ctattgcggg cttcatcgaa aacggatggg aggggctcat cgatggttgg 1080
tacggattca ggcaccagaa cgcgcagggg aaggaacggg ccgctgatta caagtcaact 1140
caatcggcca ttgaccaaat cactggcaaa ctgaatcgcc tgatcgaaaa gaccaatcag 1200
cagtttgagt tgatcgacaa cgaattcaac gaagtggaga acagattggg caatgtcatc 1260
aattcgacca gagatagcat cacggaagtc tggtcgtaca acgccgaact cctggttgcg 1320
atggaaaatc aacacaccat cgacctggcc gactccgaaa tggacaaact ctacgagcgg 1380
gtcaaacgcc agctgcgcga aaacgcagaa gaagatggaa ccggatgctt cgagatcttt 1440
cataagtgcg acgacgattg catggccagc atccggaaca atacctacga tcactccaag 1500
taccgggagg aagcgatgca aaatcggatc cagattgacc cggtcaaact gtcgtcaggc 1560
tacaaggatg tgatcctttg gttctcattc ggagcgtcct gttttatcct tctggctatt 1620
gtgatgggcc tggtgttcat ctgcgtgaag aacggaaaca tgccgctgca tatctgcatc 1680
```

| SEQ ID NO: 8 | moltype = RNA   length = 1683 |
|---|---|
| FEATURE | Location/Qualifiers |
| misc_feature | 1..1683 |
| | note = Synthetic Polynucleotide |
| source | 1..1683 |
| | mol_type = other RNA |
| | organism = synthetic construct |

SEQUENCE: 8

```
atgtacaaaa tcgtcgtcat tatcgcattg ctgggcgctg tcaagggact cgacaagatc   60
tgtctcggac accacgcggt ggctaacgga accatcgtca agaccctgac taacgagcag  120
gaagaagtga ccaacgccac cgaaactgtg aatccaccg ggatcaacag attgtgcatg  180
aagggtcgga agcacaagga tctgggaaac tgccacccga ttggaatgct catcggcacc  240
ccggcatgcg atctgcatct gactgggatg tgggataccc ttatcgagcg ggaaaacgcg  300
atcgcatact gttaccccgg tgccaccgtg aacgtggagg cgctcagaca gaagattgga  360
gagtcaggcg gcatcaacaa gatttccacg ggcttcacct acgggtcctc cattaactcc  420
gccggtacca ctcgggcctg catgcggaac ggagggaact ccttttacgc cgagctcaag  480
tggcttgtgt caaaatccaa gggacagaat ttccccaaa ccaccaacac ctataggaac  540
accgacaccg ccgaacatct cattatgtgg ggcatccatc acccttcgag cacacaggag  600
aagaatgacc tctacggcac ccagtcgctg agcatctccg tgggctcatc gacctatcgc  660
aacaacttcg tgcctgtggt cggcgcccga cctcaagtca acggacagtc cggacgcatt  720
gacttccatt ggactctggt gcaaccggga gacaacatca ctttctccca caacggcgga  780
ctgattgccc caagccgcgt gtcaaagctg atcggtagag ggctgggtat tcagtcggat  840
gctcccatcg ataacaactg cgaatccaag tgcttttgga gaggcggctc catcaatact  900
cggctgcgt ttcagaacct gagcccgagg accgtggggc agtgcccaaa atacgtgaat  960
cgccggtcac tgatgctggc gaccggaatg aggaacgtgc ctgaactcat ccagggacgg 1020
gggctgttcg gcgccatcgc cggcttcctg gaaaacggat gggagggaat ggtggacggt 1080
tggtacggct tccgccacca aaacgcccag ggaactggca ctacaagtcg ctacaatact 1140
acacaggccg caatgaccaa gatcactggg aagctcaacc gccttgtgga aaagactaac 1200
actgaattcg agtcgatcga gtctgagttc tccgagatcg aacaccagat tgggaacgtg 1260
atcaactgga cgaaggactc cattaccgac atctggacct accaggcgga actgctcgtg 1320
gcgatggaga accagcacac tatcgacatg gccgactccg agatgctgaa tctgtacgaa 1380
cgcgtgcggg agcaactgag acaaaacgct gaagaagtga aaaggggttg tttcgagatc 1440
taccacgcct cgcgacgacag ctgcatgaaa gcattagga acaataccta cgaccactcg 1500
cagtaccggg aggaggccct tctgaaccgg ctgaacatta ccccgtgac cttgagctcc 1560
ggctacaagg acatcatcct gtggttctcg tttggagcca gctgcttcgt gctgctggcc 1620
gtcgtgatgg gattgttctt cttctgcctg aaaaacggaa acatgcgctg caccatctgt 1680
att                                                               1683
```

| SEQ ID NO: 9 | moltype = RNA   length = 1997 |
|---|---|
| FEATURE | Location/Qualifiers |
| misc_feature | 1..1997 |
| | note = Synthetic Polynucleotide |

| source | 1..1997 |
| --- | --- |
| | mol_type = other RNA |
| | organism = synthetic construct |

SEQUENCE: 9

```
tcaagctttt ggaccctcgt acagaagcta atacgactca ctataggaa ataagagaga    60
aaagaagagt aagaagaaat ataagagcca ccatgaatac ccagattctc gtgttcgccc   120
tcatcgctat catcccaacc aatgccgaca agatctgctt gggtcatcat gcggtgtcga   180
acggaaccaa ggtcaacacc ctgaccgagc ggggagtgga agtggtcaac gctactgaaa   240
cggtggaaag gactaatatc ccacgcatct gctcaaaggg aaagaaaact gtggatctcg   300
gacagtgtgg acttctgggg accatcacgg gtccaccgca atgcgatcag tttctggagt   360
tcagcgcaga tctgatcatc gagcgcagag aagggtccga cgtttgttac cctgaaagt    420
tcgtgaacga agaggcactg cgccaaatct gcgggagag cggcggcatt gacaaagagg    480
ccatgggatt cacctactcg ggtattcgca ctaacggtgc cacttctgcg tgccggcgtt    540
ccgggtcctc cttctatgcc gagatgaagt ggctcctgtc gaacaccgac aacgcagctt    600
ttccgcaaat gactaagtcc tacaaaaaca ctagaaagtc gccggcactg atcgtctggg    660
gaatccatca ctccgtgtct actgcggagc aaactaagct gtacggcagc ggaaacaagc    720
tcgtgaccgt cggttcatcg aactaccagc agagctttgt gccaagcccc ggagcgaggc    780
cccaggtcaa cgggcagagc ggacgcatcg acttccactg gctgatgctc aatccgaatg    840
acaccgtgac cttctcgttc aatgcgcct tcatcgcacc tgaccgcgcc agcttcctga    900
gaggaaagtc aatgggcata cagtcgggcg tccaagtgga tgccaactgc gagggagact    960
gctatcactc cggcggaacc atcatctcca atttgccgtt tcaaaacatc gactcgcgcg   1020
cagtgggaaa gtgtccgcga tacgtgaagc agagatcact gctgctgaac actgggatga   1080
agaacgtgcc tgaaatcccg aaaggaaggg ggttgttcgg cgctattgcg ggcttcatcg   1140
aaaacgatg ggagggtc atcgatggtt ggtacggatt caggcaccag aacgcgcagg    1200
gggaaggaac ggccgctgat tacaagtcaa ctcaatcggc cattgaccaa atcactggca   1260
aactgaatcg cctgatcgaa aagaccaatc agcagtttga gttgatcgac atcgaattca   1320
acgaagtgga gaaacagatt ggcaatgtca tcaattggac cagagatagc atcacgaag   1380
tctggtcgta caacgccgaa ctcctggttg cgatggaaaa tcaacacacc atcgacctgg   1440
ccgactccga aatggacaaa ctctacgagc gggtcaaacg ccagctgcgc gaaaacgcag   1500
aagaagatgg aaccggatgc ttcgagatct ttcataagtg gacgacgat tgcatggcca   1560
gcatccggaa caatacctac gatcactcca gtaccggga ggaagcgatg caaaatcgga   1620
tccagattga cccggtcaaa ctgtcgtcag gctacaagga tgtgatcctt tggttctcat   1680
tcggagcgtc ctgttttatc cttctggcta ttgtgatggg cctggtgttc atctgcgtga   1740
agaacggaaa catgcgctgc actatctgca tctgataata ggctggagcc tcggtggcca   1800
tgcttcttgc cccttgggcc tcccccagcc ccctcctcc cttcctgcac ccgtaccccc    1860
gtggtctttg aataaagtct gagtgggcgg caaaaaaaaa aaaaaaaaa aaaaaaaaaa   1920
aaaaaaaaaa aaaaaaaaaa aaaaaaaaaa aaaaaaaaaa aaaaaaaaaa aaaaaaaaaa   1980
aaaaaaaaaa atctaga                                                 1997
```

| SEQ ID NO: 10 | moltype = RNA length = 47 |
| --- | --- |
| FEATURE | Location/Qualifiers |
| misc_feature | 1..47 |
| | note = Synthetic Polynucleotide |
| source | 1..47 |
| | mol_type = other RNA |
| | organism = synthetic construct |

SEQUENCE: 10

```
gggaataag agagaaaaga agagtaagaa gaaatataag agccacc              47
```

| SEQ ID NO: 11 | moltype = DNA length = 47 |
| --- | --- |
| FEATURE | Location/Qualifiers |
| misc_feature | 1..47 |
| | note = Synthetic Polynucleotide |
| source | 1..47 |
| | mol_type = other DNA |
| | organism = synthetic construct |

SEQUENCE: 11

```
gggaaataag agagaaaaga agagtaagaa gaaatataag agccacc             47
```

| SEQ ID NO: 12 | moltype = RNA length = 119 |
| --- | --- |
| FEATURE | Location/Qualifiers |
| misc_feature | 1..119 |
| | note = Synthetic Polynucleotide |
| source | 1..119 |
| | mol_type = other RNA |
| | organism = synthetic construct |

SEQUENCE: 12

```
tgataatagg ctggagcctc ggtggccatg cttcttgccc cttgggcctc ccccagccc    60
ctcctcccct tcctgcaccc gtaccccgt ggtctttgaa taaagtctga gtgggcggc    119
```

| SEQ ID NO: 13 | moltype = DNA length = 119 |
| --- | --- |
| FEATURE | Location/Qualifiers |
| misc_feature | 1..119 |
| | note = Synthetic Polynucleotide |
| source | 1..119 |
| | mol_type = other DNA |
| | organism = synthetic construct |

SEQUENCE: 13

```
tgataatagg ctggagcctc ggtggccatg cttcttgccc cttgggcctc ccccagccc    60
```

```
ctcctcccct tcctgcaccc gtaccccgt ggtctttgaa taaagtctga gtgggcggc      119

SEQ ID NO: 14          moltype = RNA   length = 47
FEATURE                Location/Qualifiers
misc_feature           1..47
                       note = Synthetic Polynucleotide
source                 1..47
                       mol_type = other RNA
                       organism = synthetic construct
SEQUENCE: 14
gggaaataag agagaaaaga agagtaagaa gaaatataag agccacc                   47

SEQ ID NO: 15          moltype = DNA   length = 47
FEATURE                Location/Qualifiers
misc_feature           1..47
                       note = Synthetic Polynucleotide
source                 1..47
                       mol_type = other DNA
                       organism = synthetic construct
SEQUENCE: 15
gggaaataag agagaaaaga agagtaagaa gaaatataag agccacc                   47

SEQ ID NO: 16          moltype = RNA   length = 119
FEATURE                Location/Qualifiers
misc_feature           1..119
                       note = Synthetic Polynucleotide
source                 1..119
                       mol_type = other RNA
                       organism = synthetic construct
SEQUENCE: 16
tgataatagg ctggagcctc ggtggccatg cttcttgccc cttgggcctc ccccagccc      60
ctcctcccct tcctgcaccc gtaccccgt ggtctttgaa taaagtctga gtgggcggc      119

SEQ ID NO: 17          moltype = DNA   length = 119
FEATURE                Location/Qualifiers
misc_feature           1..119
                       note = Synthetic Polynucleotide
source                 1..119
                       mol_type = other DNA
                       organism = synthetic construct
SEQUENCE: 17
tgataatagg ctggagcctc ggtggccatg cttcttgccc cttgggcctc ccccagccc      60
ctcctcccct tcctgcaccc gtaccccgt ggtctttgaa taaagtctga gtgggcggc      119

SEQ ID NO: 18          moltype = AA    length = 18
FEATURE                Location/Qualifiers
REGION                 1..18
                       note = Synthetic Polypeptide
source                 1..18
                       mol_type = protein
                       organism = synthetic construct
SEQUENCE: 18
MDWTWILFLV AAATRVHS                                                   18

SEQ ID NO: 19          moltype = AA    length = 20
FEATURE                Location/Qualifiers
REGION                 1..20
                       note = Synthetic Polypeptide
source                 1..20
                       mol_type = protein
                       organism = synthetic construct
SEQUENCE: 19
METPAQLLFL LLLWLPDTTG                                                 20

SEQ ID NO: 20          moltype =       length =
SEQUENCE: 20
000

SEQ ID NO: 21          moltype = RNA   length = 11
FEATURE                Location/Qualifiers
misc_feature           1..11
                       note = Synthetic Polynucleotide
source                 1..11
                       mol_type = other RNA
                       organism = synthetic construct
SEQUENCE: 21
gggatcctac c                                                          11

SEQ ID NO: 22          moltype =       length =
```

```
SEQUENCE: 22
000

SEQ ID NO: 23          moltype = AA  length = 4
FEATURE                Location/Qualifiers
REGION                 1..4
                       note = Synthetic Polypeptide
source                 1..4
                       mol_type = protein
                       organism = synthetic construct
SEQUENCE: 23
GGGS                                                              4
```

What is claimed is:

1. A method of inducing an influenza virus antigen-specific immune response in a human subject, the method comprising administering to the human subject a composition comprising 10-100 µg of a messenger ribonucleic acid (mRNA) polynucleotide to thereby induce a protective antigen-specific immune response in the subject, wherein the mRNA polynucleotide comprises an open reading frame encoding an influenza virus hemagglutinin (HA) antigen and is formulated in a lipid nanoparticle (LNP), wherein 100% of uracil nucleosides in the open reading frame are N1-methylpseudouridine, and wherein the LNP comprises a compound of Formula (I):

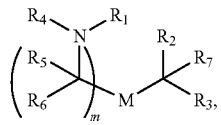

(I)

or a salt thereof, wherein:

R₁ is selected from the group consisting of $C_{5-30}$ alkyl, $C_{5-20}$ alkenyl, and —R"M'R';

R₂ and R₃ are independently selected from the group consisting of $C_{1-14}$ alkyl and $C_{2-14}$ alkenyl;

R₄ is —(CH₂)ₙQ, where Q is —OR, and each n is independently selected from 1, 2, 3, 4, and 5;

each R₅ is H;

each R₆ is H;

M and M' are independently selected from —C(O)O— and —OC(O)—;

R₇ is H;

R is H;

R' is H;

R" is selected from the group consisting of $C_{3-14}$ alkyl and $C_{3-14}$ alkenyl; and m is selected from 5, 6, 7, 8, 9, 10, 11, 12, and 13.

2. The method of claim 1, wherein the compound of Formula (I) is Compound 25:

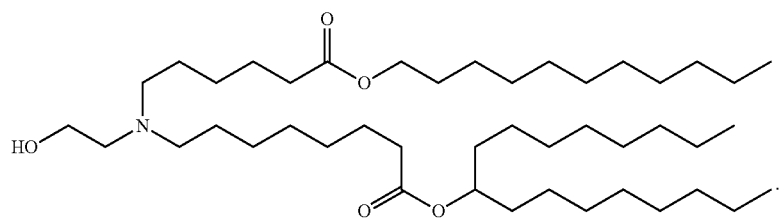

(Compound 25)

3. The method of claim 1, wherein the LNP comprises 20-60 mol % cationic lipid, 5-25 mol % neutral lipid, 25-55 mol % sterol, and 0.5-15 mol % PEG-modified lipid, wherein the LNP comprises 0.5 mol % to 5 mol % PEG-modified lipid.

4. The method of claim 1, wherein the HA antigen is an H10 HA antigen.

5. The method of claim 4, wherein the H10 HA antigen comprises an amino acid sequence with at least 80% sequence identity to the amino acid sequence of SEQ ID NO: 4.

6. The method of claim 4, wherein the HA antigen is an H10N8 HA antigen.

7. The method of claim 1, wherein the antigen-specific immune response comprises a B cell response.

8. The method of claim 1, wherein the antigen-specific immune response comprises a T cell response.

9. The method of claim 1, further comprising administering a booster dose of the composition to the human subject.

10. The method of claim 1, wherein the method of producing an antigen-specific immune response involves a single administration of the composition, and wherein the protective immune response is produced with the single administration.

* * * * *